US007826977B2

(12) United States Patent
Garty et al.

(10) Patent No.: US 7,826,977 B2
(45) Date of Patent: Nov. 2, 2010

(54) SYSTEMS AND METHODS FOR HIGH-SPEED IMAGE SCANNING

(75) Inventors: Guy Garty, Dobbs Ferry, NY (US); Gerhard Randers-Pehrson, Ossining, NY (US); David J. Brenner, New York, NY (US); Oleksandra V. Lyulko, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 391 days.

(21) Appl. No.: 11/895,470

(22) Filed: Aug. 24, 2007

(65) Prior Publication Data

US 2008/0228404 A1 Sep. 18, 2008

Related U.S. Application Data

(60) Provisional application No. 60/840,245, filed on Aug. 25, 2006, provisional application No. 60/942,090, filed on Jun. 5, 2007, provisional application No. 60/954,499, filed on Aug. 7, 2007.

(51) Int. Cl.
*G01N 33/00* (2006.01)

(52) U.S. Cl. .................. 702/19; 250/459.1; 250/461.1; 250/504 R; 250/491.1

(58) Field of Classification Search .................. 702/19, 702/21–22, 27–28, 31; 356/317–318, 417; 250/458.1, 459.1, 461.1, 461.2, 491.1, 504 R
See application file for complete search history.

(56) References Cited

U.S. PATENT DOCUMENTS

| | | | | |
|---|---|---|---|---|
| 4,626,244 | A | 12/1986 | Reinicke | |
| 5,572,598 | A | 11/1996 | Wihl et al. | |
| 5,747,813 | A | 5/1998 | Norton et al. | |
| 6,496,267 | B1 * | 12/2002 | Takaoka | 356/497 |

(Continued)

OTHER PUBLICATIONS

Abramsson-Zetterberg L., et al. (2000). Human cytogenetic biomonitoring using flow-cytometric analysis of micronuclei in transferrin-positive immature peripheral blood reticulocytes. Environ Mol Mutagen; 36:22-31.

(Continued)

*Primary Examiner*—Hal D Wachsman
*Assistant Examiner*—Mary C O'Malley
(74) *Attorney, Agent, or Firm*—Sonnenschein Nath & Rosenthal LLP

(57) ABSTRACT

Systems and methods for high-speed image scanning are disclosed herein One aspect of the invention is directed to a method for high speed image scanning. The method for high speed image scanning includes adjusting an object using a positioning element; directing a portion of an image of the object toward a sensor by positioning a first mirror relative to the object, and by positioning a second mirror relative to the object and the first mirror; controlling the positioning element, the position of the first mirror and the position of the second mirror using a processor; and detecting the portion of the image of the object using the sensor positioned relative to the first mirror and the second mirror. In accord with this method, the first mirror directs the portion of the image of the object in a first direction and the second mirror directs the portion of the image of the object in a second direction.

75 Claims, 38 Drawing Sheets

U.S. PATENT DOCUMENTS

| | | | | |
|---|---|---|---|---|
| 6,974,938 | B1 | 12/2005 | Leblans et al. | |
| 6,980,294 | B2 * | 12/2005 | Namba et al. | 356/318 |
| 2003/0030741 | A1 | 2/2003 | Ohta | |
| 2003/0142398 | A1 | 7/2003 | Leblans | |
| 2004/0143461 | A1 | 7/2004 | Watkins | |
| 2005/0043894 | A1 | 2/2005 | Fernandez | |
| 2005/0043984 | A1 | 2/2005 | Hodgson | |
| 2005/0191047 | A1 | 9/2005 | Toji | |
| 2005/0247874 | A1 * | 11/2005 | Ando et al. | 250/306 |
| 2007/0036039 | A1 * | 2/2007 | Kawahara et al. | 369/13.01 |

OTHER PUBLICATIONS

Anderson, R. C., et al. (2000). A miniature integrated device for automated multistep genetic assays. Nucleic Acids Research; 28(12): e60.

Becker, H., et al. (1998). Planar quartz chips with submicron channels for two-dimensional capillary electrophoresis applications. Journal of Micromechanics and Microengineering 8(1): 24-28.

Boumsellek, S., et al. (2001). Trade-offs in miniature quadrupole designs. J. Am. Soc. Mass Spectrom.; 12, 633-640.

Burge, M. R., et al. (1998). Use of a laser skin perforator for determination of capillary blood glucose yields reliable results and high patient acceptability. Diabetes Care; 21:871-3.

Burns, M. A., et al. (1998). An integrated nanoliter DNA analysis device. Science 282(5388): 484-487.

Burns, T.F., et al. (2003). Microarray analysis of p53 target gene expression patterns in the spleen and thymus in response to ionizing radiation. Cancer Biol Ther, 2, 431-443.

Caspermeyer, J., (2005). Biodesign Institute joins fight against 'dirty bombs'. Inside ASU Magazine, Sep. 30, 2005.

Chalmers, J. J., et al. (1998). Flow through, immunomagnetic cell separation. Biotechnology Progress 14(1): 141-148.

Cheng, J., et al. (1998). Sample preparation in microstructured devices. Microsystem Technology in Chemistry and Life Science. 194: 215-231.

Chou, C.F., et al. (2002). Electrodeless Dielectrophoretic Trapping and Separation of Cells. Micro Total Analysis Systems 2002, Nara, Japan.

Chou, C.F., et al. (2003). Electrodeless dielectrophoresis for micro total analysis systems. Engineering in Medicine and Biology Magazine (IEEE). 22(6): 62-67.

Chou, S. Y., et al. (1995). Imprint of Sub-25 Nm Vias and Trenches in Polymers. Applied Physics Letters 67(21): 3114-3116.

Chou, S. Y., et al. (1996). Imprint lithography with 25-nanometer resolution. Science 272(5258): 85-87.

Dertinger, S. D., et al. (2002). Enumeration of micronucleated CD71-positive human reticulocytes with a single-laser flow cytometer. Mutat Res; 515:3-14.

Dertinger, S. D., et al. (2004). Three color labeling method for flow cytometric measurement of cytogenetic damage in rodent and human blood. Environ Mol Mutagen; 44:427-35.

Eiceman, G.A., et al. (2002). Micro-machined planar field asymmetric ion mobility spectrometer as a gas chromatographic detector. Analyst, 127, 466-471.

Fodor, S. P. A., et al. (1991). Light-Directed, Spatially Addressable Parallel Chemical Synthesis. Science 251(4995): 767-773.

Follador, M.J., et al. (2004). Detection of cocaine and cocaethylene in sweat by solid-phase microextraction and gas chromatography/mass spectrometry. J Chromatogr B Analyt Technol Biomed Life Sci, 811, 37-40.

Fornace, A. J., Jr., et al. (1999). The complexity of radiation stress responses: analysis by informatics and functional genomics approaches. Gene Expression, 7, 387-400.

Fortina, P., et al. (2000). Simple two-color array-based approach for mutation detection. European Journal of Human Genetics 8(11): 884-894.

Fortina, P., et al. (2001). DOP-PCR Amplification of Whole Genomic DNA and Microchip-Based Capillary Electrophoresis. Capillary Electrophoresis of Nucleic Acids, vol. 2, Humana Press, p. 211-219.

Garty, G., (2006). Advances in high-throughput biodosimetry. Presentation at the 2006 Micro-Workshop on Nanodosimetry, Nes-Ziona, Israel, Dec. 1-4, 2006.

Garty, G., et al. (2007). Development of an ultrahigh-throughput robotically based biodosimetry workstation using in situ assays. Abstract accepted for poster presentation at the $13^{th}$ International Congress of Radiation Research, San Francisco, California.

Garty, G., et al. (2007). Interfacing a high-throughput robotic biodosimetry workstation with emergency response personnel. Abstract submitted to the 2nd Annual Interagency Workshop Using Environmental Data during Emergencies: From Field Data Collection to Risk Communication, sponsored by the New York City Department of Health and Mental Hygiene.

Garvey, K., et al. (1999). Blood lancing systems for skin puncture. Prof Nurse; 14:643-8, 50-1.

Grace, M. B., et al. (2003). Development and assessment of a quantitative reverse transcription-PCR assay for simultaneous measurement of four amplicons. Clin Chem; 49:1467-75.

Harrison, D. J., et al. (1992). Capillary Electrophoresis and Sample Injection Systems Integrated on a Planar Glass Chip. Analytical Chemistry 64(17): 1926-1932.

Harrison, D. J., et al. (1993). Micromachining a Miniaturized Capillary Electrophoresis-Based Chemical-Analysis System on a Chip. Science 261(5123): 895-897.

Hayata, I., et al., (1992). Robot system for preparing lymphocyte chromosome. J. Radiation Research, 33(Supplement): p. 231-241.

Hook, G.L., et al. (2003). Detection of VX contamination in soil through solid-phase microextraction sampling and gas chromatography/mass spectrometry of the VX degradation product bis(diisopropylaminoethyl)disulfide. J Chromatogr A, 992, 1-9.

Hook, G.L., et al. (2004). Dynamic solid phase microextraction for sampling of airborne sarin with gas chromatography-mass spectrometry for rapid field detection and quantification. J Sep Sci, 27, 1017-1022.

Huang, Z., et al. (1999). A new closed-form kinematics of the generalized 3-DOF spherical parallel manipulator. Robotica; 17:475-85.

Jiang, G. F., et al. (2000). mRNA isolation in a microfluidic device for eventual integration of cDNA library construction. Analyst 125(12): 2176-2179.

Joung, J., et al. (2000). Micro Pumps Based on Alternating High Gradient Magnetic Fields. IEEE Trans. on Magnetics 36: 2012.

Kachel, V., et al., (2006). High-throughput isolation of ultra-pure plasmid DNA by a robotic system. BMC Biotechnology, 6(9).

Kimm, G.L., et al. (2002). Application of headspace solid-phase microextraction and gas chromatography-mass spectrometry for detection of the chemical warfare agent bis(2chloroethyl) sulfide in soil. J Chromatogr A, 971, 185-191.

Kopp, M., et al. (1998). Chemical amplification: Continuous-Flow PCR on a chip. Science 280: 1046-1048.

Kricka, L. J., et al. (2002). Fabrication of plastic microchips by hot embossing. Lab on a Chip 2(1): 1-4.

Kronstrand, R., et al. (2004). Screening for drugs of abuse in hair with ion spray LC-MS-MS. Forensic Sci Int, 145, 183-190.

Kumar, R., et al. (2003). Preliminary experiments in robot/human cooperative microinjection. Proceedings of the Oct. 2003 IEEE/RSJ Int'l. Conference on Intelligent Robots and Systems. Las Vegas, NV, p. 3186-91.

Lagally, E. T., et al. (2001). Single-molecule DNA amplification and analysis in an integrated microfluidic device. Analytical Chemistry 73(3): 565-570.

Langlois, R. G., et al. (1990). An improved flow cytometric assay for somatic mutations at the glycophorin A locus in humans. Cytometry; 11:513-21.

Lenigk, R., et al. (2002). Plastic biochannel hybridization devices: a new concept for microfluidic DNA arrays. Analytical Biochemistry 311(1): 40-49.

Liu, R. H., et al. (2001). Highly Parallel Integrated Microfluidic Biochannel Arrays. Technical Digest of the 14th International Conference on Micro Electro Mechanical Systems, Interlaken, Switzerland.

Liu, R. H., et al. (2004). Self-contained, fully integrated biochip for sample preparation, polymerase chain reaction amplification, and DNA microarray detection. Anal Chem; 76:1824-31.

Livingston, G.K., et al., (1997). Radiobiological evaluation of immigrants from the vicinity of Chernobyl. International Journal of Radiation Biology, 72: p. 703-713.
Loinaz, M., (1999). Video cameras: CMOS technology provides on-chip processing. Sensor Review; 19:19-26.
Long, X., et al. (2004). Effective automatic recognition of cultured cells in bright field images using Fisher's linear discriminant preprocessing. In Proceedings of IMECE04: 2004 ASME International Mechanical Engineering Congress. Anaheim, California.
Long, X., et al. (2005). A new preprocessing approach for cell recognition. IEEE Transactions on Information Technology in Biomedicine, vol. 9, No. 3; p. 407-12.
Long, X., et al. (2006). Automatic detection of unstained viable cells in bright field images using a support vector machine with an improved training procedure. Computers in Biology and Medicine; 36, p. 339-62.
Lots, J. F., et al. (2001). A 2-D visual servoing for underwater vehicle station keeping. Proceedings of the 2001 IEEE Conference on Robotics and Automation. Seoul, Korea; p. 2767-72.
Lozano, A., et al. (2003). Pattern analysis of cell micronuclei images to evaluate their use as indicators of cell damage. Engineering in Medicine and Biology Society, 2003. Proceedings of the 25th Annual International Conference of the IEEE. vol. 1. Cancun, Mexico: IEEE; p. 731-4.
Lu, C.-J., et al. (2003). Functionally integrated MEMS micro gas chromatograph subsystem. 7th International Conference on Miniaturized Chemical and Biochemical Analysis Systems, 411-415.
Lyulko, O. V., et al. (2007). Fully-automated rapid in situ cellular imaging for a high-throughput biodosimetry workstation. Abstract accepted for poster presentation at the 13$^{th}$ International Congress of Radiation Research, San Francisco, California, Jul. 8-12, 2007.
Majid, M. Z., et al. (2000). Workspace analysis of a six-DOF, three-PPSR parallel manipulator. International Journal of Advanced Manufacturing Technology; 17:441-9.
Manginell, R.P., et al. (2003). Monolithically-integrated MicroChemLab for gas-phase chemical analysis. 7th International Conference on Miniaturized Chemical and Biochemical Analysis Systems.
Manz, A., et al. (1992). Planar Chips Technology for Miniaturization and Integration of Separation Techniques into Monitoring Systems—Capillary Electrophoresis on a Chip. Journal of Chromatography 593(1-2): 253-258.
Meldrum, D.R., et al., (2005). Sample Preparation in Glass Capillaries for High-Throughput Biochemical Analyses, in International Conference on Automation Science and Engineering. Edmonton, Canada.
Mezouar, Y., et al. (2002). Visual servoed micropositioning for protein manipulation. In Proceedings 2002 IEEE/RSJ International Conference on Intelligent Robots and Systems : IROS 2002 , Sep. 30-Oct. 4, 2002, EPFL, Lausanne, Switzerland. Piscataway, New Jersey: IEEE; p. 1766-77.
Miller, R.A., et al. (2001). A MEMS radio-frequency ion mobility spectrometer for chemical vapor detection. Sensors and Actuators A, 91, 301-312.
Mitchell, C. R., et al. (2004). Stable intrachromosomal biomarkers of past exposure to densely ionizing radiation in several chromosomes of exposed individuals. Radiat Res; 162:257-63.
Nusse, M., et al. (1997). Flow cytometric analysis of micronuclei in cell cultures and human lymphocytes: advantages and disadvantages. Mutat Res; 392:109-15.
Offer, T., et al. (2004). A simple assay for frequency of chromosome breaks and loss (micronuclei) by flow cytometry of human reticulocytes. Faseb J.; p. 485-87.
Parton, J. W., et al. (1996). Validation of an automated image analysis micronucleus scoring system. Mutat Res; 370:65-73.
Patterson, A. D., et al. (2007). Metabolomics as a tool for understanding the cellular stress response of TK6 cells following ionizing radiation exposure. Abstract accepted for presentation at the 13$^{th}$ International Congress of Radiation Research, San Francisco, California.
Pellmar, T. C., et al. (2005). Priority list of research areas for radiological nuclear threat countermeasures. Radiat Res; 163:115-23.
Prasanna, P. G., et al. (2005). Premature chromosome condensation in human resting peripheral blood lymphocytes for chromosome aberration analysis using specific whole-chromosome DNA hybridization probes. Methods Mol Biol; 291:49-57.
Prasanna, P.G.S., et al., (2005). Cytogenetic Biodosimetry for Radiation Disasters: Recent Advances. Technical Report. (AFRRI CD 05-2). Armed Forces Radiobiology Research Institute.
Randers-Pehrson, G., et al. (2001). The Columbia University single-ion microbeam. Radiat Res; 156:210-4.
Romanyukha, A. A., et al. (2005). Spectrum file size optimization for EPR tooth dosimetry. Appl Radiat Isot; 62:197-200.
Rosenthal, P., et al. (2003). Calibration and validation of a quality assurance system for 90Sr/90Y radiation source trains. Phys Med Biol; 48:573-85.
Schunck, C., et al. (2004). New developments in automated cytogenetic imaging: unattended scoring of dicentric chromosomes, micronuclei, single cell gel electrophoresis, and fluorescence signals. Cytogenet Genome Res; 104:383-9.
Shi, Y. N., et al. (1999). Radial capillary array electrophoresis microplate and scanner for high-performance nucleic acid analysis. Analytical Chemistry 71(23): 5354-5361.
Shortt, B. J., et al. (2005). Miniaturized system of a gas chromatograph coupled with a Paul ion trap mass spectrometer. J Mass Spectrom, 40, 36-42.
Silwood, C. J., et al. (1999). 1HNMR analysis of microbial-derived organic acids in primary root carious lesions and saliva. NMR Biomed, 12, 345-356.
Skelley, A. M., et al. (2005). Development and evaluation of a microdevice for amino acid biomarker detection and analysis on Mars. Proc Natl Acad Sci U S A, 102, 1041-1046.
Smolewski, P., et al. (2001). Micronuclei assay by laser scanning cytometry. Cytometry; 45:19-26.
Soldatova, L. N., et al., (2006). An ontology for a robot scientist. Bioinformatics, 22(14): p. 464-471.
Styles, J. A., et al. (2001). Automation of mouse micronucleus genotoxicity assay by laser scanning cytometry. Cytometry; 44:153-5.
Taylor, M. T., et al. (2001). Fully Automated Sample Preparation for Pathogen Detection Performed in a Microfluidic Cassette. Micro Total Analysis Systems: 670-672.
Thierens, H., et al. (1991). Biological dosimetry using the micronucleus assay for lymphocytes: interindividual differences in dose response. Health Phys; 61:623-30.
Tian, W.-C., et al. (2003). Microfabricated preconcentrator-focuser for a microscale gas chromatograph. J Microelectromech Sys, 12, 264-272.
Titenko-Holland, N., et al. (1994). Measurement and characterization of micronuclei in exfoliated human cells by fluorescence in situ hybridization with a centromeric probe. Mutat Res; 312:39-50.
Tyburski, J. B., et al. (2007). Radiation metabolomics permits discovery of mouse urinary biomarkers for gamma radiation exposure. Abstract accepted for presentation at the 13$^{th}$ International Congress of Radiation Research, San Francisco, California.
Umek, R. M., et al. (2001). Electronic detection of nucleic acids—A versatile platform for molecular diagnostics. Journal of Molecular Diagnostics 3(2): 74-84.
Urbanczyk-Wochniak, E., et al. (2003). Parallel analysis of transcript and metabolic profiles: a new approach in systems biology. EMBO Rep, 4, 989-993.
Varga, D., et al. (2004). An automated scoring procedure for the micronucleus test by image analysis. Mutagenesis; 19:391-7.
Verhaegen, F., et al. (1994). Scoring of radiation induced micronuclei in cytokinesis-blocked human lymphocytes by automated image analysis. Cytometry; 17:119-27.
Vral, A., et al. (1994). The in vitro cytokinesis-block micronucleus assay: a detailed description of an improved slide preparation technique for the automated detection of micronuclei in human lymphocytes. Mutagenesis; 9:439-43.
Wang, J., et al. (2004). Optimizing RNA extraction yield from whole blood for microarray gene expression analysis. Clinical Biochemistry 37: 741-744.
Ward, M. D., et al. (2002). Metal-Polymer Hybrid Microchannels for Microfluidic High Gradient Separations. European Cells and Materials, vol. 3, Suppl 2, p. 123-125.

Waters, L. C., et al. (1998). Microchip device for cell lysis, multiplex PCR amplification, and electrophoretic sizing. Analytical Chemistry 70(1): 158-162.

Wilding, P., et al. (1994). Manipulation and Flow of Biological-Fluids in Straight Channels Micromachined in Silicon. Clinical Chemistry 40(1): 43-47.

Wilding, P., et al. (1998). Integrated cell isolation and polymerase chain reaction analysis using silicon microfilter chambers. Analytical Biochemistry 257(2): 95-100.

Wilson, I. D., et al. (2005). HPLC-MS-based methods for the study of metabonomics. J Chromatogr B Analyt Technol Biomed Life Sci, 817, 67-76.

Woolley, A. T., et al. (1994). Ultra-High-Speed DNA Fragment Separations Using Microfabricated Capillary Array Electrophoresis Chips. Proceedings of the National Academy of Sciences of the United States of America 91(24): 11348-11352.

Woolley, A. T., et al. (1996). Functional integration of PCR amplification and capillary electrophoresis in a microfabricated DNA analysis device. Analytical Chemistry 68(23): 4081-4086.

Yang, J. N., et al. (2002). High sensitivity PCR assay in plastic micro reactors. Lab on a Chip 2(4): 179-187.

Yao, Y. L., (1991). Transient lateral motion of robots in cylindrical part mating. Robotics and Computer Integrated Manufacturing; 8:103-11.

Yao, Y. L., et al. (1993). Maximum allowable load of flexible manipulators for a given dynamic trajectory. Robotics and Computer-Integrated Manufacturing; 10:301-9.

Yao, Y. L., et al. (1995). Recursive calibration of industrial manipulators by adaptive filtering. Journal of Engineering for Industry-Transactions of the ASME; 117:406-11.

Yao, Y. L., et al. (1999). Model based motion planning of robot assembly of non-cylindrical parts. International Journal of Advanced Manufacturing Technology; 15:683-91.

Yu, H., et al. (2000). A Miniaturized and Integrated Plastic Thermal Chemical Reactor for Genetic Analysis. uTAS 2000, The Netherlands, Kluwer Academic Publishers.

Yuen, P. K., et al. (2001). Microchip module for blood sample preparation and nucleic acid amplification reactions. Genome Research 11(3): 405-412.

Department of Homeland Security, Technology assessment and roadmap for the emergency radiation dose assessment program ERDAP, http://www3.niaid.nih.gov/research/topics/radnuc/PDF/TechAssessment.pdf, Jun. 2005.

International Search Report issued on Feb. 25, 2008, in related application PCT/US07/76825.

International Search Report issued on Sep. 12, 2008, in related application PCT/US07/18931.

International Search Report issued on Sep. 26, 2008, in related application PCT/US07/76802.

Office Acion in the related U.S. Appl. No. 11/895,360, issued May 5, 2010.

* cited by examiner a)

b)

A

B

Linear Barcode (Code 128) of 10 mm length on PVC capillaries.

| Overview of the robotic instrument (breadboard stage) | Close up view of the robotic pipette arm micromanipulator | Rear view of the breadboard-stage robot liquid handling subsystem |
| --- | --- | --- |

SYSTEMS AND METHODS FOR HIGH-SPEED IMAGE SCANNING

CROSS-REFERENCE TO RELATED APPLICATIONS

This application claims priority from U.S. Provisional Application Ser. No. 60/840,245 filed on Aug. 25, 2006; U.S. Provisional Application Ser. No. 60/942,090 filed Jun. 5, 2007; and U.S. Provisional Application Ser. No. 60/954,499 filed Aug. 7, 2007, each of which is incorporated herein by reference in its entirety.

STATEMENT REGARDING FEDERALLY SPONSORED RESEARCH OR DEVELOPMENT

This invention was made in part with Government support under Department of Health and Human Services Grant U19A1067773-01. The Government has certain rights in the invention.

FIELD

The present application generally relates to systems, devices, and methods for minimally-invasive, high-throughput radiation biodosimetry using commonly available biological samples.

BACKGROUND

The Homeland Security Council recently established an interagency working group (Pellmar T C, Rockwell S. and the Radiological/Nuclear Threat Countermeasures Working Group: Priority list of research areas for radiological nuclear threat countermeasures. Radiat Res 2005; 163:115-23) to assess and prioritize the nation's needs in terms of a response to a terrorist attack using radiological or nuclear devices. Biodosimetry assay automation, biomarkers and devices for biodosimetry, and training in radiation sciences were among the areas of research identified as top or high priorities.

Products for high throughput minimally-invasive biodosimetry are clearly needed. After a large-scale radiological event, there will be a major need to assess, within a few days, the radiation doses received by tens or hundreds of thousands of individuals.

SUMMARY

Systems and methods for high-speed image scanning are disclosed herein One aspect of the invention is directed to a method for high speed image scanning. The method for high speed image scanning includes adjusting an object using a positioning element; directing a portion of an image of the object toward a sensor by positioning a first mirror relative to the object, and by positioning a second mirror relative to the object and the first mirror; controlling the positioning element, the position of the first mirror and the position of the second mirror using a processor; and detecting the portion of the image of the object using the sensor positioned relative to the first mirror and the second mirror. In accord with this method, the first mirror directs the portion of the image of the object in a first direction and the second mirror directs the portion of the image of the object in a second direction.

In various embodiments, the first mirror and the second mirror are galvanometric mirrors. In various embodiments, the sensor is a CMOS sensor. In other embodiments, the sensor is a charge coupled device. In various embodiments, the first mirror and the second mirror are located between an objective lens and a tube lens. In various embodiments, the positioning element is a linear actuator. In other embodiments, the positioning element is a stepper motor. In various embodiments, the object is glued onto a substrate. In other embodiments, the object is laminated onto a substrate.

In various embodiments, the method for high speed image scanning further includes dividing the object into a plurality of fields of view and/or dividing each of the plurality of fields of view into a plurality of high magnification views.

In various embodiments, the object is a biological sample. In various embodiments, the method for high speed image scanning further includes adding microspheres having a predetermined diameter to the biological sample; illuminating the microspheres such that they emit a wavelength different than the wavelength emitted by the biological sample; imaging the microspheres; and adjusting the position of the imaging element to bring the biological sample into focus. In various embodiments, the microspheres have a diameter greater than about 0.6 micrometers. In some configurations, the microspheres have a diameter of about 10 micrometers. In various embodiments, the microspheres have a diameter greater than the diameter of a filter substrate located adjacent to the biological sample. In various embodiments, the microspheres are fluorescent and the fluorescence of the microspheres is different than the fluorescence used to image the sample. In some configurations, the color of the microspheres have an excitation wavelength of about 625 nm and an emission spectrum of about 645 nm. In various embodiments, the microspheres are illuminated using a lamp. In various embodiments, the microspheres are illuminated using a laser. In various embodiments, the microspheres are detected using a CMOS sensor. In various embodiments, the microspheres are detected using a charge coupled device.

In various embodiments, the method for high speed image scanning further includes positioning at least a portion of an imaging element using a piezo nano-positioner. In various embodiments, the imaging element is a magnifying objective lens. In various embodiments, the imaging element is a magnifying objective lens and a tube lens.

In various embodiments, the method for high speed image scanning further includes positioning a dichroic mirror in the path of the image of the sample to allow focusing on the microspheres or imaging of the sample. In various embodiments, the microspheres are fluorescent.

In various embodiments, the sensor is a first sensor and the method for high speed image scanning further includes directing the image of the object toward at least one of the first sensor and a second sensor. In various embodiments, the image of the object is directed along a first optical path to the first sensor and along a second optical path to the second sensor. In various embodiments, the image of the object is directed toward at least one of the first sensor and the second sensor using a dichroic mirror. In various embodiments, the method for high speed image scanning further includes magnifying a first image along the first optical path to a first level of magnification and magnifying a second image along the second optical path to a second level of magnification. In various embodiments, the method for high speed image scanning further includes directing a plurality of images of the object to the first sensor. In various embodiments, the method for high speed image scanning further includes analyzing the plurality of images. In various embodiments, at least one of the plurality of images is analyzed using cluster analysis.

In various embodiments, the method for high speed image scanning further includes analyzing the results of a analysis; comparing the results of the cluster analysis to a threshold; and directing an image of the object to a second sensor when the results of the cluster analysis exceed the threshold. In various embodiments, the second sensor is a 3 CMOS color sensor array.

In various embodiments, the method for high speed image scanning further includes illuminating the object using a light source. In various embodiments, the light source is an argon ion laser. In various embodiments, the light source is an LED. In various embodiments, the light source is a lamp. In various embodiments, the method for high speed image scanning further includes illuminating the object for a first instance using a first light source and illuminating the object for a second instance using a second light source. In various embodiments, the first light source is an LED and the second light source is an argon ion laser.

Another aspect of the invention is directed to an apparatus for high speed image scanning. The apparatus for high speed image scanning includes an imaging element; positioning element; a first mirror; a second mirror; and a processor. In accord with the apparatus, the positioning element controllable in an x direction and in a y direction, and the positioning element is coupled to an object. The positioning element can thus adjust the position of the object. Also in accord with the apparatus, the first mirror is positioned relative to the object; and the second mirror is positioned relative to the object and the first mirror. The first mirror directs at least one image of the object in the x direction toward the second mirror, and the second mirror directs the at least one image of the object in the y direction toward a sensor. Also in accord with the apparatus, the processor is coupled to the positioning element, the first mirror, and the second mirror. The processor thereby controls the positioning element, the position of the first mirror, and the position of the second mirror.

In various embodiments, the first mirror and the second mirror are galvanometric mirrors. In various embodiments, the sensor is a CMOS sensor. In various embodiments, the sensor is a charge coupled device.

In various embodiments, the apparatus further includes an objective lens and a tube lens and wherein the first mirror and the second mirror are located between an objective lens and a tube lens. In various embodiments, the apparatus further includes an imaging element. In various embodiments, a portion of the imaging element is a magnifying objective lens. In various embodiments, the positioning element is a linear actuator. In various embodiments, the positioning element is a stepper motor. In various embodiments, the first mirror and the second mirror are adjusted to provide images of the object from a plurality of fields of view. In various embodiments, the first mirror and the second mirror are adjusted to provide a plurality of high magnification images of the object from each of the plurality of fields of view.

In various embodiments, the object is a sample in a well in an array. In various embodiments, the apparatus further includes a plurality of microspheres having a predetermined diameter; wherein the microspheres are added to the sample; and a light source. In accord with these embodiments, the light source illuminates the microspheres such that the microspheres emit a wavelength different than the wavelength emitted by the sample; and the sensor detects the images of the microspheres and the positioning element adjusts the position of the imaging element to bring the sample into focus. In various embodiments, the microspheres have a diameter greater than about 0.6 micrometers. In some configurations, the microspheres have a diameter of about 10 micrometers. In various embodiments, the microspheres have a diameter greater than the diameter of a filter substrate included in the well. In various embodiments, the microspheres have a diameter similar to the diameter of the object to be imaged. In various embodiments, the microspheres have a fluorescence and the fluorescence is different than the fluorescent used to image the sample. In some configurations, the microspheres have an excitation wavelength of about 625 nm and an emission spectrum of about 645 nm. In various embodiments, the microspheres are illuminated using a lamp. In various embodiments, the microspheres are illuminated using a laser. In various embodiments, the microspheres are illuminated using a diode. In various embodiments, the microspheres are detected using a CMOS sensor. In various embodiments, the microspheres are detected using a charge coupled device. In various embodiments, the position of at least a portion of the imaging element is adjusted using a piezo nano-positioner.

In various embodiments, the imaging element is a magnifying objective lens. In various embodiments, the apparatus further includes a dichroic mirror, wherein the dichroic mirror is positioned in the path of the image of the sample to allow focusing on the microspheres. In various embodiments, the apparatus further includes a dichroic mirror, wherein the dichroic mirror is positioned in the path of the image of the sample to allow imaging of the sample. In various embodiments, the sensor is a first sensor and the apparatus further includes a second sensor, wherein the first mirror directs an image in the x direction toward the second mirror and the second mirror directs the image in the y direction toward at least one of the first sensor and the second sensor. In various embodiments, the first sensor is positioned along a first optical path and the second sensor is positioned along a second optical path. In various embodiments, the first optical path includes a first level of magnification and the second optical path includes a second level of magnification. In various embodiments, the at least one of the plurality of images is directed to the first sensor.

In various embodiments, the apparatus further includes a software program for analyzing the plurality of images. In various embodiments, the plurality of images is analyzed using cluster analysis. In various embodiments, the results of the cluster analysis are compared to a threshold, and when the results of the cluster analysis exceed the threshold, an image of the object is directed to the second sensor. In various embodiments, the second sensor is a 3 CMOS color sensor array. In various embodiments, the apparatus further includes a light source, wherein the light source illuminates the object. In various embodiments, the light source is an argon ion laser. In various embodiments, the light source is an LED. In various embodiments, the light source is a lamp. In various embodiments, the apparatus further includes a first light source and a second light source. In various embodiments, the first light source is an LED and the second light source is an argon ion laser.

Another aspect of the invention is a system for high speed image scanning. The system for high speed image scanning includes an imaging means, a positioning means, a first reflecting means, a second reflecting means, and a processing means. In accord with the system, the imaging means for providing a magnified image of an object. In accord with the system, the positioning means is controllable in an x direction and in a y direction, and is coupled to an object, such that the positioning means adjusts the position of the object. In accord with the system, the first reflecting means is positioned relative to the object, and the second reflecting means is positioned relative to the object and the first reflecting means. In accord with the system, the first reflecting means directs at least one image in the x direction toward the second reflecting means and the second reflecting means directs the at least one image of the object in the y direction toward a sensing means. In accord with the system, the processing means is coupled to the positioning means, the first reflecting means, and the second reflecting means, such that the processing means controls the positioning means, the position of the first reflecting means, and the position of the second reflecting means.

Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION

Figure 1:
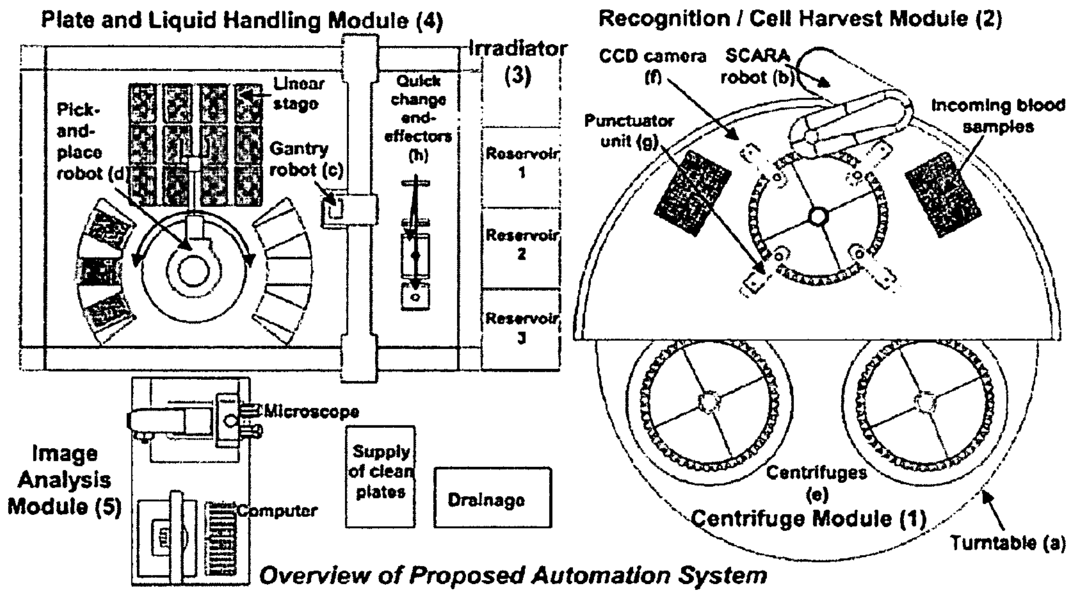
FIG. 1 illustrates a system overview of an embodiment of the invention.

The need for high throughput rapid biodosimetry can be well illustrated by reference to the 1987 radiation incident in Goiânia, Brazil, a city with about the same population as Manhattan. In the first few days after the incident became known, about 130,000 people (roughly 10% of the population) came for screening, of whom 20 required treatment (International Atomic Energy Agency. The Radiological accident in Goiânia. Vienna: International Atomic Energy Agency; 1988). In response to a RDD (radiological dispersal device) event in a US city, one would anticipate a similar scenario. Tens or hundreds of thousands of individuals will need to be screened for radiation exposure within a few days due to demand and the medical necessity to perform radiological triage.

Mass radiological triage will be critical after a large-scale event in order to identify, at an early stage, those individuals who will benefit from medical intervention. In addition, eliminating and reassuring patients who do not need medical intervention will be crucial in a highly resource-limited scenario.

Regarding those who do require medical intervention, the best estimate for the LD50/60 in humans is in the 3.5 to 4.5 Gy range (Anno G H, Young R W, Bloom R M, Mercier J R. Dose response relationships for acute ionizing radiation lethality. Health Phys 2003; 84:565-75), but this value can be roughly doubled through the use of antibiotics, platelet and cytokine treatment (Anno G H, Young R W, Bloom R M, Mercier J R. Dose response relationships for acute ionizing radiation lethality. Health Phys 2003; 84:565-75). Thus, it is crucial that individuals who actually received whole-body doses above a pre-determined threshold value, for example, 0.5, 1.0, 1.1, 1.2, 1.3, 1.4, 1.5, 1.6, 1.7, 1.8, 1.9, or 2.0 Gy are identified and treated. Some individuals who are in this dose range will be clearly identifiable through early nausea, vomiting, and acute fatigue, but not all. For example, worker "C" at the 1999 radiation accident at Tokai-mura received a best-estimate whole-body equivalent dose of more than 3 Gy (Ishigure N, Endo A, Yamaguchi Y, Kawachi K. Calculation of the absorbed dose for the overexposed patients at the JCO criticality accident in Tokai-mura. J Radiat Res (Tokyo) 2001; 42 Suppl:S137-48; Hayata I, Kanda R, Minamihisamatsu M, Furukawa M, Sasaki M S. Cytogenetical dose estimation for 3 severely exposed patients in the JCO criticality accident in Tokai-mura. J Radiat Res (Tokyo) 2001; 42 Suppl:S149-55), was initially almost entirely asymptomatic, yet developed bone marrow failure (Hirama T, Tanosaki S, Kandatsu S, Kuroiwa N, Kamada T, Tsuji H, et al. Initial medical management of patients severely irradiated in the Tokai-mura criticality accident. Br J Radiol 2003; 76:246-53). Thus, accurate biodosimetry is crucial in this dose range.

At higher doses, e.g., between 5 and 12 Gy, there is also a critical need for biodosimetry. This is because there is only a quite narrow dose window (approximately 7-10 Gy) in which bone-marrow transplantation is a useful option (below 7 Gy, survival rates are good solely with medication, while above 10 Gy patients will generally have lethal gastrointestinal damage) (Hall E J. Radiobiology for the radiologist. 5th ed. Philadelphia: Lippincott, Williams & Wilkins; 2000). Thus, it is important to ascertain, through biodosimetry, whether a patient's dose is within this dose window, such that a bone-marrow transplant is a useful option.

It should be noted that the dose estimates discussed above are for adults. Children are likely to be more sensitive to radiation than adults in terms of their LD50. Fred SS, Smith WW. Radiation sensitivity and proliferative recovery of hemopoietic stem cells in weanling as compared to adult mice. Radiat Res 1967; 32:314-26; Reincke U, Mellmann J, Goldmann E. Variations in radioresistance of rats during the period of growth. Int J Radiat Biol Relat Stud Phys Chem Med 1967; 13:137-46; Ward B C, Childress J R, Jessup G L, Jr., Lappenbusch W L. Radiation mortality in the Chinese hamster, *Cricetulus griseus*, in relation to age. Radiat Res 1972; 51:599-607. Thus, it is desirable that biodosimetric information should also be obtainable at lower doses in children.

Embodiments of the invention disclosed herein emphasize extremely high throughput (many thousands of samples per day per machine), in contrast to current technologies which feature at most a few hundred samples per day per machine (Offer T, Ho E, Traber M G, Bruno R S, Kuypers F A, Ames B N. A simple assay for frequency of chromosome breaks and loss (micronuclei) by flow cytometry of human reticulocytes. Faseb J 2004; Styles J A, Clark H, Festing M F, Rew D A. Automation of mouse micronucleus genotoxicity assay by laser scanning cytometry. Cytometry 2001; 44: 153-5).

A related issue is that of invasive vs. noninvasive/minimally-invasive biodosimetry. The term "invasive biodosimetry," as used herein, refers to procedures that require a qualified health professional, such as the drawing of peripheral blood through venipuncture. Such a procedure would be a major bottleneck, in that a health professional can, at most, draw blood from 15 to 25 individuals per hour. Accordingly, embodiments of the invention disclosed herein relate to minimally invasive procedures, such as a capillary blood finger or heel stick. Other embodiments relate to non-invasive approaches such as the use of exfoliated cells from a buccal smear (mouthwash), or from urine. Some embodiments relate to completely self-contained readily-deployable biodosimetry kits.

Another issue with regard to biodosimetry is that of inter-individual variability in radiation sensitivity. Specifically, it would be highly desirable to be able to recognize individuals with high radiation sensitivity, a) because they would constitute a high-risk group which might warrant different and/or additional follow-up procedures, and because b) particularly at high doses (>2 Gy) the uncertainty in a biodosimetrically-based dose estimate will predominantly be due to inter-individual differences (Thierens H, Vral A, de Ridder L. Biological dosimetry using the micronucleus assay for lymphocytes: interindividual differences in dose response. Health Phys 1991; 61:623-30). Thus, embodiments of the invention described herein address this issue. In some aspects of this embodiment, each biological sample is split in two, with one of the two split samples being irradiated to a known dose, before being analyzed. This will allow a positive control for each individual, so that the effects of inter-individual variability in radiosensitivity can be taken into account.

Another issue is that of lower-dose biodosimetry, for example, doses of less than 2 Gy, 1.8 Gy, 1.5 Gy, 1.2 Gy, 1 Gy, 0.9 Gy, 08 Gy, 0.7 Gy, 0.6 Gy, 0.5 Gy, 0.4 Gy, 0.3 Gy or 0.1 Gy. While, such doses are typically below life-threatening, it is likely that long-term carcinogenic risk as a result of such doses will be increased. Thus, in the event of a large-scale radiological event, the dosimetric data generated according to the invention disclosed herein could form the basis for long-term epidemiological studies.

Another consideration is the information required. In many situations, for example, an appropriate first level of triage might be a very rapid yes/no answer as to whether a predetermined threshold dose has been exceeded. In other situations, an actual dose estimate is important.

While all the biodosimeters will be calibrated over a wide dose range, some biodosimeters are more appropriate for lower doses, some for higher doses, and some are useful over a very wide range of doses. For example, for an individual who potentially received an extremely high dose, e.g., 10 Gy; a DSB (γ-H2AX) approach would be more informative than a micronuclei approach.

An additional issue is time since exposure. Some biodosimeters, such as micronuclei in lymphocytes, are very stable with time, over a period of many weeks. Some biodosimeters are practical for use only within limited time periods after the radiation incident. For example, the γ-H2AX biodosimeter, which reflects the presence of DNA double strand breaks, will be most useful in the first 36 hours after a radiation event, while micronuclei in blood reticuloctyes will be most useful from about 24 to 60 hours after radiation exposure. These considerations strongly imply that different biodosimetric endpoints may be needed for different situations.

Thus, some embodiments relate to a multi-input and/or multi-endpoint high-throughput product, which can be applied in different situations. In one embodiment, the automated device is useful for both blood lymphocytes and for reticuloctyes, as well as for exfoliated cells from urine or buccal smears, and the device can measure both micronuclei and γ-H2AX foci. In a preferred embodiment, any combination of endpoints can be applied by using different pre-determined sets of instructions in the robotically-based system.

The biomarker should have appropriate specificity, i.e. the measured response should be specific to radiation, as opposed to a more general stress response, or a chemical or biological agent response.

Current systems for performing radiation biodosimetry have limited throughputs of a few hundred samples per day. Offer T, Ho E, Traber M G, Bruno R S, Kuypers F A, Ames B N. A simple assay for frequency of chromosome breaks and loss (micronuclei) by flow cytometry of human reticulocytes. Faseb J 2004; Styles J A, Clark H, Festing M F, Rew D A. Automation of mouse micronucleus genotoxicity assay by laser scanning cytometry. Cytometry 2001; 44:153-5; Smolewski P, Ruan Q, Vellon L, Darzynkiewicz Z. Micronuclei assay by laser scanning cytometry. Cytometry 2001; 45:19-26; Dertinger S D, Chen Y, Miller R K, Brewer K J, Smudzin T, Torous D K, et al. Micronucleated CD71-positive reticulocytes: a blood-based endpoint of cytogenetic damage in humans. Mutat Res 2003; 542:77-87. Accordingly, embodiments of the invention described herein relate to systems, devices and methods for high-throughput, minimally invasive radiation biodosimetry.

Described herein is a high-throughput biodosimetry device that, in some embodiments, uses purpose-built robotics and/or advanced high-speed automated image acquisition and analysis. In preferred embodiments, throughput is at least about 1,000, 2,000, 3,000, 4,000, 5,000, 7,500, 10,000, 12,500, 15,000, 17,500, 20,000, 22,500, 25,000, 27,500, 30,000, 35,000 40,000, 45,000, 50,000, 60,000, 70,000, 75,000, 80,000, 90,000, or 100,000 samples day, compared with current maximal throughputs of a few hundred samples/day. In some embodiments, several endpoints (micronuclei and/or γ-H2AX foci) and/or several tissues (blood lymphocytes, reticuloctyes, and/or exfoliated cells from urine or a buccal smear) can be used. Purpose-built liquid-handling robotics and advanced high-speed automated image acquisition can be used to increase throughput.

Some embodiments relate to a system or device that employs a micronucleus assay in lymphocytes, with such assays being carried out in-situ in multi-well plates. Peripheral blood drawn by venipuncture using a finger or heelstick or a high-throughput laser skin perforator is used. In some embodiments, pre-programmed options in timing, liquid handling, and image analysis, the device are used to measure γ-H2AX foci yields and/or micronucleus yields in reticuloctyes, thereby providing "same-day answer" dose estimates. In some embodiments, pre-programmed options in liquid handling steps are used to measure micronuclei in other readily-accessible tissues, such as exfoliated cells from urine or buccal smears. In preferred embodiments, each biological sample is split in two, with one of the two split samples being irradiated to a known dose before being analyzed. This allows a positive control for each individual, providing an internal calibration account for inter-individual variability in radiosensitivity.

In some embodiments, a system using 96-well plates provides a throughput target of 6,000 samples (3,000 individuals) per 15 hour day. In another embodiment, a system using 384-well plates -provides a throughput target of 30,000 (15,000 individuals) samples per 15 hour day.

Other embodiments relate to a blood handling subsystem that uses either capillary tubes or larger vacutainer tubes. The tubes can be plastic or glass. In a preferred embodiment, the device uses capillary tubes.

Monochrome imaging or color imaging can be used. In some embodiments, a color image can be split into two or more, individually processed, monochrome images using dichroic beamsplitters, for example.

Some embodiments disclosed herein relate to a workstation comprising a blood collection module, an irradiation module, a cell harvesting module, a sample identification and tracking module, a lymphocyte incubation module, a liquid/plate handling robot, an image acquisition/processing system, and optionally, an irradiation module.

In one embodiment, equipment used for the elements of the workstation includes:

VideoScope Gen III High Resolution Intensifier; Photonfocus MV-D1024 series CMOS High Speed Monochrome Digital Camera System; Upstate Technical Equipment Co. Inc., East Syracuse, N.Y.; Matrox Solios XCL Camera Link; Martox, Montreal, QC, Canada: One or more of each of these items can be used for image capture and read out. The image intensifier boosts the image intensity to a level required for fast imaging. CMOS sensors are the fastest imaging device commercially available that also suit embodiments of the invention disclosed herein. The Matrox Solios XCL is used to read and process the image data.

Mirror/Scanner, Scanlab HurryScan II; Scanlab America Naperville, Ill.: The galvanometer scanner system is used as the steering mechanism for the steered-image compound microscope. This optical scanning system benefits the proposed instrumentation with its fast speed, especially when compared to the settling times of bulky mechanical stages. The short switching time improves speed for promoting high throughput.

Nikon, CFI60 20X Objective; Cube Changer; Morrell Instrument Company, Inc., Melville, N.Y.; Mad City, Z-motion 100 micron Piezo Nano Positioner; Mad City, Piezo-Controller; Mad City labs, Madison, Wis.; EXFO X-Cite 120 illumination system, (EXFO America inc, plano TX): This objective lens is the primary lens used for imaging the cell samples. It is a lens with infinity optics, which enables other optical elements (mirror/scanner) to be added into an afocal space, while not distorting the image quality. The piezo nano positioner is used for precision auto-focusing. The illumination source for the microscope in a first embodiment is a high intensity mercury bulb with fiber optic light guide. For multi-component imaging, the cube changer is used to select which wavelength is used for excitation and observation of various fluorochromes.

Daedal X-Y Mechanical Stage With Compumotor Stepper Motor Control, Axis New York, Fairport, N.Y.: This stepper-motor controlled X-Y mechanical stage is designated for coarse motions for the sample arrays being imaged with the microscope. The speed and resolution of this stage is suited for high throughput.

Computer, CyberResearch, Inc., New Haven, Conn.: This computer system is an industrial strength machine with room for numerous expansion cards for image processing. The computer is equipped with one terra byte of storage space and a back-up power supply.

NanoLED —625 nm; NanoLED Controller; HORIBA Jobin Yvon, Inc., Edison, N.J.: This LED light source is used for excitation of the fluorescent beads that are used in the auto-focusing routine on the microscope.

Kendro centrifuge(s); Sorvall rotor(s); accessories; Kendro Laboratory Products, Asheville, N.C.: One or more of each of these items form the core of the centrifuge module. The rotors are custom made to have capacity of 48 vacutainer CPT tubes. With the radiation and control scheme, one rotor load of samples fills a 96-well plate.

Components to construct the turn table and jack mechanism for the centrifuge module cylinder with spline joint, timing wheel and belt, two DC motors with encoders and reduction gears, precision bearings, multi-channel motion control card, amplifiers and power supplies, SDP-SI, New Hyde Park, N.Y., ORMEC Systems Corp. Rochester, N.Y., McMaster-Carr, New Brunswick, N.J.: The turn table and jack mechanism with the centrifuge and rotors above complete the centrifuge module. Additional components including brackets, housing, and supports that are designed and fabricated as needed.

Sony DXC-990 Industrial CCD camera, Schneider XENON 17 mm lens, Mikrotron Inspecta frame grabber, Sony Corporation, Mikrotron GmbH, Germany: These items build part of the visual servoing system for the cell harvest module. One set is sufficient for a device. Additional sets can be added for increased throughput.

Components to construct the punctuation unit (DC motor with encoders and reduction gear, precision lead screw and ball-bearing nut, precision rail and carriage, motion control card, amplifier and power supply) (SDP-SI, New Hyde Park, N.Y., ORMEC Systems Corp. Rochester, N.Y., McMaster-Carr, New Brunswick, N.J.) These items complete the visual servoing system for the cell harvest module. Additional components including brackets, housing, and supports are designed and fabricated as needed. Only one set of these items is required, but additional sets can be added for increased throughput.

Adept Cobra i800 SCARA robot and accessories (Adept Technology, Inc., Livermore, Calif.) SCARA (selective compliance assembly robot arm) robots provide excellent pick and place accuracy under very high speed in a simple structure. The Adept robots pioneered the direct-drive (without reduction gears) SCARC robot to bring the accuracy and speed to a new level. This robot is dedicated to interface the centrifuge and cell harvest modules and a special end-effector is fabricated to load and unload vacutainer CPT tubes to and from a centrifuge rotor.

Modified Zymark (now Caliper Life Sciences) Sciclone ALH 3000 including the gantry robot) (Caliper Life Sciences, Hopkinton, Mass.): This liquid handling system meets most of the current needs but a number of modifications are made either by working with the supplier or on site. The width of the system is increased from approximately 800 mm to 1100 mm to accommodate incorporation of a pick-and-place robot and plate stacker within the working envelope of the gantry robot. The two-robot configuration allows task dedication and thus high throughput. The available EZ-swap dispense module (attached to the gantry robot) is modified to enable pneumatically actuated quick change of different end-effector modules. The liquid handling portion of the system is also modified to handle the radiated and control samples.

Allen Bradley (now Rockwell Automation) Programmable Logical Controller (PLC) with accessories; two computers (Rockwell Automation, Inc, Milwaukee, Wis., Dell Computer, Austin, Tex.) The two computers host the motion control cards for the turn table/jack mechanism and the punctuation unit, respectively. The PLC implements the sequential control of the entire operation involving all system components. The PLC interfaces with some components directly such as the Adept SCARA robot, and with others via digital input/out capabilities of their motion control cards residing in the computers.

Center for Radiological Research Radiation seeds 4 mCi; (Bebig, Berlin, Germany): Nine of these radioactive seeds are used as the radiation source in the Strontium-90 irradiator.

Argon-Ion Laser, (Coherhent Inc., Santa Clara, Calif.): This Argon-ion laser is used as a light source for the microscope in one embodiment. It provides a brighter illumination, which is required for fast imaging, and the light quality is improved over a Mercury bulb used in an alternative embodiment.

Laser Optics, (Newport, Irvine, Calif.): Assorted laser optics are used along the light path for the Argon-ion laser. Also an assortment of filters, cubes, and mirrors are incorporated into the steered-image compound microscope.

Robotioc incubator, (Liconic US, Inc, Woburn, Mass.): This incubator is used as an atmosphere for the cell samples while they are being treated and stored prior to the imaging sequence. The robotic incubator is capable of storing a few hundreds of multi-well plates and dispensing individual plates automatically.

Pick-and-place robot, plate stackers and linear stage from Matrix Tango Stacker system (without liquid handling subsystem) (Matrix Technologies, Hudson, N.H.) These items are integrated within the working envelope of the gantry liquid handling robot, working in tandem. The linear stage holds 12 plates which are sufficient. Additional stackers are included to provide total capacity of 300 plates. The pick-and-place robot also interfaces with the microscope for image acquisition.

Sony DXC-990 Industrial CCD camera, Schneider XENON 17 mm lens, Mikrotron Inspecta frame grabber, (Sony Corporation, Mikrotron GmbH, Germany) These items build part of the visual servoing system for the cell harvest module.

Components to construct the punctuation unit (DC motor with encoders and reduction gear, precision lead screw and ball-bearing nut, precision rail and carriage, motion control card, amplifier and power supply) (SDP-SI, New Hyde Park, N.Y., ORMEC Systems Corp. Rochester, N.Y., McMaster-Carr, New Brunswick, N.J.) These items complete the visual servoing system for the cell harvest module. They share a motion control card.

OEM barcode printing and applying components from VCode by Velocity 11, barcode reader, date acquisition and control (DAC) board and monitoring software computer (Velocity 11, Menlo Park, Calif., Symbol Technologies, Holtsville, N.Y., National Instruments, Austin, Tex., Dell Computer, Austin, Tex.) The OEM components are integrated with the plate stackers and pick-and-place robot for barcode label applying on microplates for identification and tracking by the barcode reader. The DAC board has multi-channel analog-to-digital converter which collects the current signals from all the actuators in the entire system to monitor any overshooting as sign of trouble spots. The on-board digital-to-analog converters connect to the actuator circuits for emergency stops. Both barcode card and DAC board reside in a computer.

VideoScope Gen III High Resolution Intensifier; pco. 12 hs 10-bit CMOS High Speed Monochrome Digital Camera System; pco. 2000 14-bit High Performance Monochrome Digital Camera System; Matrox Odyssey Xpro Camera Link; (The Cooke Corporation, Romulus, Mich.): These items are used for image capture and read out for multi-color imaging in one embodiment of the device. The image intensifiers boost the image intensity to a level required for fast imaging. The 14-bit camera is a CCD camera that will acquire the low magnification images. The additional CMOS sensor enables multi-color imaging using two sensors. The Matrox Odyssey Xpro cards are used to read and process the image data.

Color Separation Prism, (Redlake, San Diego, Calif.): This item distributes the optics path in the microscope according to wavelength and will be used for multi-color imaging.

Lasette Laser Lancing Device; Lens Shields (box of 250); (Cell Robotics, Inc., Albuquerque, N. Mex.): This laser lancing device is used for the perforation of skin to draw capillary blood samples. This device eliminates injuries and uses disposable single-use lens shields to prevent cross-contamination.

Three Sorvall rotors with bundled swing bucket; accessories (Kendro Laboratory Products, Asheville, N.C.) The rotors are custom modified to have special swing buckets for capillary tubes. Each bucket can hold multiple capillary tubes.

Additional Adept Cobra i800 SCARA robot and accessories (Adept Technology, Inc., Livermore, Calif.) Together with the SCARA robot it is used for: 1) transferring capillary tubes from centrifuge to the tube feeder and 2) transferring cell plug to the flushing system after tube cutting. The two robots are dedicated to these tasks with custom designed and fabricated end-effectors.

Components to construct the tube feeder (feeding tray, loading unit, monitoring unit, etc.) (Hoppmann Corporation, Elkwood, Va., SDP-SI, New Hyde Park, N.Y., McMaster-Carr, New Brunswick, N.J.) These items build part of the tube feeders for feeding the capillary tubes into the pneumatic transportation systems. Additional components and supports are fabricated as needed on site. Two sets of feeders are needed for a second embodiment of the device: one for samples subject to irradiation, another for control samples. The tube feeders have the ability of feeding multiple transportation systems simultaneously.

Components to construct the pneumatic system for capillary tube transportation (portable compressed air supplier, air dryer and filter, transportation pipe network, valves, regulators, control board, etc.) (Parker Air & Fuel Division, Irvine, Calif., McMaster-Carr, New Brunswick, N.J.) These items build part of the pneumatic transportation system for the centrifuged capillary tubes. Additional components such as fixtures and brackets are fabricated as needed. One set is sufficient for the device, but additional sets can be added to increase throughput.

Sony DXC-990 Industrial CCD camera, Schneider XENON 17 mm lens, Mikrotron Inspecta frame grabber, (Sony Corporation, Mikrotron GmbH, Germany) These items build part of the visual servoing systems for the visual servoed cutting unit and irradiation unit, respectively.

Components to construct the visual servoed irradiation unit (mechanical barrier, motor, rail, carriage, motion control card, etc., irradiation source not included) (SDP-SI, New Hyde Park, N.Y., ORMEC Systems Corp. Rochester, N.Y., McMaster-Carr, New Brunswick, N.J.) These items build part of the visual servoed irradiation unit. Additional components including the irradiation source are fabricated as needed.

Components to construct the visual servoed cutting unit (mechanical barrier, cutting tool, motor, rail, carriage, motion control card, etc.) (SDP-SI, New Hyde Park, N.Y., ORMEC Systems Corp. Rochester, N.Y., McMaster-Carr, New Brunswick, N.J.) These items build part of the visual servoed cutting unit. Additional components and supports are fabricated as needed.

Components to construct the cell plug flushing system (liquid reservoir, motor, slides, etc) (Upchurch Scientific, Inc, Oak Harbor, Wash., SDP-SI, New Hyde Park, N.Y., McMaster-Carr, New Brunswick, N.J.) These items build part of the cell plug flushing system for transferring harvested cells into the microplate. Additional components such as fixtures and brackets are fabricated as needed. Two sets of this flushing system are needed for the second embodiment of the device: one for samples subject to irradiation, another for control samples.

VideoScope Gen III High Resolution Intensifier; pco. 12 hs 10-bit CMOS High Speed Monochrome Digital Camera System; Matrox Odyssey Xpro Camera Link; (The Cooke Corporation, Romulus, Mich.): These items are used for image capture and read out. They provide a third image sensor to further the multi-color imaging capabilities. The image intensifier boosts the image intensity to a level required for fast imaging. The Matrox Odyssey Xpro is used to read and process the image data.

Comprehensive RFID Tagging System, (TAGSYS, Doylestown, Pa.): This system is used as a tracking device for each sample as the sample is acquired from individuals and is then processed for imaging.

Components to construct an additional pneumatic system for capillary tube transportation (portable compressed air supplier, air dryer and filter, transportation pipe network, regulators, valves, control board, etc.) (Parker Air & Fuel Division, Irvine, Calif., McMaster-Carr, New Brunswick, N.J.) These items build part of the second pneumatic transportation system for the centrifuged capillary tubes. Additional components such as fixtures and brackets are fabricated as needed.

Sony DXC-990 Industrial CCD camera, Schneider XENON 17 mm lens, Mikrotron Inspecta frame grabber, (Sony Corporation, Mikrotron GmbH, Germany) These items build part of the visual servoing system for an additional irradiation unit.

Components to construct an additional visual servoed irradiation unit (mechanical barrier, motor, rail, carriage, motion control card, etc., irradiation source not included) (SDP-SI, New Hyde Park, N.Y., ORMEC Systems Corp. Rochester, N.Y., McMaster-Carr, New Brunswick, N.J.) These items build part of the second visual servoed irradiation unit. Additional components including the irradiation source are fabricated as needed.

Components to upgrade the liquid handling system and quick-change end-effectors with μl scale ability and accessories, (Caliper Life Sciences, Hopkinton, Mass.) The liquid handling tasks in the first embodiment of the device are mostly in ml scale. For the second embodiment, the accuracy of the liquid handling system is improved to handle liquid at the μl-level. Both liquid handling end-effectors and liquid moving subsystems are upgraded.

Two Kendro centrifuges; three Sorvall rotors; accessories; (Kendro Laboratory Products, Asheville, N.C.) These items form the core of the centrifuge module. The rotors are custom made to have capacity of 48 vacutainer CPT tubes. With the radiation and control scheme, one rotor load of samples will fill a 96-well plate.

Components to construct the turn table and jack mechanism for the centrifuge module (cylinder with spline joint, timing wheel and belt, two DC motors with encoders and reduction gears, precision bearings, multi-channel motion control card, amplifiers and power supplies) (SDP-SI, New Hyde Park, N.Y., ORMEC Systems Corp. Rochester, N.Y., McMaster-Carr, New Brunswick, N.J.) The turn table and jack mechanism with the centrifuge and rotors above complete the centrifuge module. Additional components including brackets, housing, and supports are fabricated as needed.

Sony DXC-990 Industrial CCD camera, Schneider XENON 17 mm lens, Mikrotron Inspecta frame grabber, (Sony Corporation, Mikrotron GmbH, Germany) These items build part of the visual servoing system for the cell harvest module.

Components to construct the punctuation unit (DC motor with encoders and reduction gear, precision lead screw and ball-bearing nut, precision rail and carriage, motion control card, amplifier and power supply) (SDP-SI, New Hyde Park, N.Y., ORMEC Systems Corp. Rochester, N.Y., McMaster-Carr, New Brunswick, N.J.) These items complete the visual servoing system for the cell harvest module. Additional components including brackets, housing, and supports are fabricated as needed.

Adept Cobra i800 SCARA robot and accessories (Adept Technology, Inc., Livermore, Calif.) SCARA (selective compliance assembly robot arm) robots provide excellent pick and place accuracy under very high speed in a simple structure. The Adept robots pioneered the direct-drive (without reduction gears) SCARC robot to bring the accuracy and speed to a new level. This robot is dedicated to interface the centrifuge and cell harvest modules and a special end-effector is fabricated to load and unload vacutainer CPT tubes to and from a centrifuge rotor.

Modified Zymark (now Caliper Life Sciences) Sciclone ALH 3000 including the gantry robot) (Caliper Life Sciences, Hopkinton, Mass.) This liquid handling system meets most of our needs but a number of modifications are made. The width of the system is increased from approximately 800 mm to 1100 mm to accommodate our configuration incorporating a pick-and-place robot and plate stacker within the working envelope of the gantry robot. The two-robot configuration is designed in favor of task dedication and thus high throughput. Another important modification is the available EZ-swap dispense module (attached at the end of the gantry robot) which is modified to enable pneumatically actuated quick change of different end-effector modules. The liquid handling portion of the system is also modified to handle the radiated and control samples.

Allen Bradley (now Rockwell Automation) Programmable Logical Controller (PLC) with accessories; two computers (Rockwell Automation, Inc, Milwaukee, Wis., Dell Computer, Austin, Tex.) The two computers host the motion control cards for the turn table/jack mechanism and the punctuation unit, respectively. The PLC implements the sequential control of the entire operation involving all system components. The PLC interfaces with some components directly such as the Adept SCARA robot, and with others via digital input/out capabilities of their motion control cards residing in the computers.

Pick-and-place robot, plate stackers and linear stage from Matrix Tango Stacker system (without liquid handling subsystem) (Matrix Technologies, Hudson, N.H.) These items are integrated within the working envelope of the gantry liquid handling robot, working in tandem. The linear stage holds 12 plates which are sufficient. Additional stackers are included to provide total capacity of 300 plates. The pick-and-place robot also interfaces with the microscope for image acquisition.

Sony DXC-990 Industrial CCD camera, Schneider XENON 17 mm lens, Mikrotron Inspecta frame grabber, (Sony Corporation, Mikrotron GmbH, Germany) These items build part of the visual servoing system for the cell harvest module.

Components to construct the punctuation unit (DC motor with encoders and reduction gear, precision lead screw and ball-bearing nut, precision rail and carriage, motion control card, amplifier and power supply) (SDP-SI, New Hyde Park, N.Y., ORMEC Systems Corp. Rochester, N.Y., McMaster-Carr, New Brunswick, N.J.) These items complete the visual servoing system for the cell harvest module.

OEM barcode printing and applying components from VCode by Velocity 11, barcode reader, date acquisition and control (DAC) board and monitoring software computer (Velocity 11, Menlo Park, Calif., Symbol Technologies, Holtsville, N.Y., National Instruments, Austin, Tex., Dell Computer, Austin, Tex.) The OEM components are integrated with the plate stackers and pick-and-place robot for barcode label applying on microplates for identification and tracking by the barcode reader. The DAC board has multi-channel analog-to-digital converter which collects the current signals from all the actuators in the entire system to monitor any overshooting as sign of trouble spots. The on-board digital-to-analog converters connect to the actuator circuits for emergency stops. Both barcode card and DAC board reside in a computer.

Three Sorvall rotors with bundled swing bucket; accessories (Kendro Laboratory Products, Asheville, N.C.) The rotors will be custom modified to have special swing buckets for capillary tubes. Each bucket holds multiple capillary tubes.

Additional Adept Cobra i800 SCARA robot and accessories (Adept Technology, Inc., Livermore, Calif.) Together with the SCARA robot, it functions for the following tasks: 1) transferring capillary tubes from centrifuge to the tube feeder and 2) transferring cell plug to the flushing system after tube cutting. The two robots are dedicated to these tasks with custom designed and fabricated end-effectors.

Components to construct the tube feeder (feeding tray, loading unit, monitoring unit, etc.) (Hoppmann Corporation, Elkwood, Va., SDP-SI, New Hyde Park, N.Y., McMaster-Carr, New Brunswick, N.J.) These items build part of the tube feeders for feeding the capillary tubes into the pneumatic transportation systems. Additional components and supports are fabricated as needed. Two sets of feeders are needed for the second embodiment of the device: one for samples subject to irradiation, another for control samples. The tube feeders are designed to have the ability of feeding multiple transportation systems simultaneously.

Components to construct the pneumatic system for capillary tube transportation (portable compressed air supplier, air dryer and filter, transportation pipe network, valves, regulators, control board, etc.) (Parker Air & Fuel Division, Irvine, Calif., McMaster-Carr, New Brunswick, N.J.) These items build part of the pneumatic transportation system for the centrifuged capillary tubes. Additional components such as fixtures and brackets are fabricated as needed.

Sony DXC-990 Industrial CCD camera, Schneider XENON 17 mm lens, Mikrotron Inspecta frame grabber, (Sony Corporation, Mikrotron GmbH, Germany) These items build part of the visual servoing systems for the visual servoed cutting unit and irradiation unit, respectively.

Components to construct the visual servoed irradiation unit (mechanical barrier, motor, rail, carriage, motion control card, etc., irradiation source not included) (SDP-SI, New Hyde Park, N.Y., ORMEC Systems Corp. Rochester, N.Y., McMaster-Carr, New Brunswick, N.J.) These items build part of the visual servoed irradiation unit. Additional components including the irradiation source are fabricated as needed.

Components to construct the visual servoed cutting unit (mechanical barrier, cutting tool, motor, rail, carriage, motion control card, etc.) (SDP-SI, New Hyde Park, N.Y., ORMEC Systems Corp. Rochester, N.Y., McMaster-Carr, New Brunswick, N.J.) These items build part of the visual servoed cutting unit. Additional components and supports are fabricated as needed.

Components to construct the cell plug flushing system (liquid reservoir, motor, slides, etc) (Upchurch Scientific, Inc, Oak Harbor, Wash., SDP-SI, New Hyde Park, N.Y., McMaster-Carr, New Brunswick, N.J.) These items build part of the cell plug flushing system for transferring harvested cells into the microplate. Additional components such as fixtures and brackets are fabricated as needed. Two sets of this flushing system are needed for the second embodiment: one for samples subject to irradiation, another for control samples.

Components to construct an additional pneumatic system for capillary tube transportation (portable compressed air supplier, air dryer and filter, transportation pipe network, regulators, valves, control board, etc.) (Parker Air & Fuel Division, Irvine, Calif., McMaster-Carr, New Brunswick, N.J.) These items build part of the second pneumatic transportation system for the centrifuged capillary tubes. Additional components such as fixtures and brackets are fabricated as needed.

Sony DXC-990 Industrial CCD camera, Schneider XENON 17 mm lens, Mikrotron Inspecta frame grabber, (Sony Corporation, Mikrotron GmbH, Germany) These items build part of the visual servoing system for an additional irradiation unit.

Components to construct an additional visual servoed irradiation unit (mechanical barrier, motor, rail, carriage, motion control card, etc., irradiation source not included) (SDP-SI, New Hyde Park, N.Y., ORMEC Systems Corp. Rochester, N.Y., McMaster-Carr, New Brunswick, N.J.) These items build part of the second visual servoed irradiation unit. Additional components including the irradiation source are fabricated as needed.

Components to upgrade the liquid handling system and quick-change end-effectors with μl scale ability and accessories, (Caliper Life Sciences, Hopkinton, Mass.) The liquid handling tasks in the first embodiment are mostly in ml scale. For the second embodiment, the accuracy of the liquid handling system is improved to handle liquid at the μl-level. Both liquid handling end-effectors and liquid moving subsystems are upgraded.

Sony DXC-990 Industrial CCD camera, Schneider XENON 17 mm lens, Mikrotron Inspecta frame grabber, (Sony Corporation, Mikrotron GmbH, Germany) These items build part of the visual servoing system for an additional cutting unit.

Components to construct an additional visual servoed cutting unit (mechanical barrier, cutting tool, motor, rail, carriage, motion control card, etc.) (SDP-SI, New Hyde Park, N.Y., ORMEC Systems Corp. Rochester, N.Y., McMaster-Carr, New Brunswick, N.J.) These items build part of the second visual servoed cutting unit. Additional components and supports are fabricated as needed.

Components to construct an additional cell plug flushing system (liquid reservoir, motor, slides, etc.) (Upchurch Scientific, Inc, Oak Harbor, Wash., SDP-SI, New Hyde Park, N.Y., ORMEC Systems Corp. Rochester, N.Y., McMaster-Carr, New Brunswick, N.J.) These items build part of the second cell plug flushing system for transferring harvested cells into the microplate. Additional components such as fixtures and brackets will be designed are fabricated as needed.

Computers (precision work station), (Dell, Inc, Round Rock, Tex.) In order to meet the high throughput requirement, multiple precision work stations with up-to-date configuration are used in image analysis tasks. These workstations implement Linux cluster for parallel computing.

Other useful materials and supplies for using the device include, for example, sterile plastic ware, tissue culture flasks, cell culture media, mitogens, growth supplements, micropipette tips, filtering units, centrifuge tubes, blood and sterile sample collection materials, gloves, masks incubator, gases, laboratory waste disposal containers, liquid nitrogen micropipettors, sterile tips, cell substrate films, glassware, sterile 96 well plates with filtration capacity, vacuum manifolds and vacuum system components, small machine parts, metals and machine shop supplies, electronic components suitable for integration into small devices, microscopy supplies, fluorescent stains, fixatives, optimized Chroma fluorescence filters, calibration kits, small refrigerators, water baths, washing and cleaning supplies.

Stainless steel and aluminum alloy materials are used for fabricating structures and parts for the turn table and jack mechanism, for the cell harvest module, and for the modification of the liquid handling system, machine shop, components to modify the liquid handling system including regulators, pumps, syringes, valves, and tubing, design and simulation software maintenance, and other consumables.

Stainless steel and aluminum alloy materials are used for fabricating structures and parts for the additional three units of visual servoing and punctuation units for the cell harvest module, and for the quick-change end-effector stations, for integrating the OEM barcode components with the plate stackers and pick-and-place robot, machine shop, components to modify the liquid handling system including regulators, pumps, valves, and tubing, design and simulation software maintenance, and other consumables Stainless steel and aluminum alloy materials are used for fabricating structures and parts for the pneumatic transportation system, the visual servoed cutting unit, the visual servoed irradiation unit, the capillary tube feeder, the cell plug flushing system and for the modification of centrifuge rotors.

Components to build the liquid handling unit for cell plug flushing system include regulators, pumps, syringes, valves, and tubing, design and simulation software maintenance, and other commercially available components.

Stainless steel and aluminum alloy materials are used for fabricating structures and parts for the additional set of pneumatic transportation system and additional visual servoed irradiation unit.

Also used are auxiliary components to modify the liquid handling system to adapt to the new end-effectors, design and simulation software maintenance, and other commercially available components.

Stainless steel and aluminum alloy materials are used for fabricating structures and parts for the additional set of visual servoed cutting unit and additional cell plug flushing system.

Also used are auxiliary components to build the liquid handling unit for cell plug flushing system, design and simulation software maintenance, and other commercially available components.

In some embodiments, the automated device described herein includes of 1) a centrifuge module; 2) a cell recognition/harvest module, with a lymphocyte/monocyte pre-screening component, 3) a mini-irradiator module; 4) a plate handling/liquid handling module; 5) an incubator and 6) an image acquisition/processing module.

The advantages and limitations of various known biodosimeters are described in (Amundson S A, Bittner M, Meltzer P, Trent J, Formace A J, Jr. Biological indicators for the identification of ionizing radiation exposure in humans. Expert Rev Mol Diagn 2001; 1:211-9). In choosing the biodosimeters for the embodiments of the invention disclosed herein, criteria considered were 1) whether a reasonable dose range was covered; 2) whether a reasonable range of time-since-exposure was covered; 3) sensitivity and specificity; 4) the extent to which the system has been characterized in the literature for low throughput studies; 5) whether the assay is amenable to high-throughput robotically-based automation; 6) the invasiveness of the assay (at most minimally invasive, ideally non invasive); and 7) whether the selected endpoints could share a common platform.

In light of these considerations, the potential tissues are lymphocytes or reticuloctyes in blood, and exfoliated buccal cells from the cheek or exfoliated bladder cells from urine. Correspondingly, the potential endpoints are micronuclei and γ-H2AX foci. These endpoints satisfy the above criteria and share a common multi-well based in-situ scanning platform. Accordingly, assay protocols have been optimized for application to fully-automated, high-throughput, multi-well in-situ assays, for:

a. micronucleus yields in lymphocytes;

b. γ-H2AX yields in lymphocytes;

c. micronucleus yields in blood reticuloctyes; and/or d. micronucleus yields in exfoliated bladder cells from urine, or exfoliated buccal cells.

System optimization is one using ex-vivo irradiated samples from healthy human volunteers. Calibration and testing is achieved using samples from adult and pediatric patients who were subject to total body irradiation.

Micronuclei in lymphocytes: This is a well-characterized endpoint (M. Fenech and A. A. Morley, Measurement of Micronuclei in Lymphocytes. Mutation Research, 1985. 147 (1-2): p. 29-36; Goans R E, Holloway E C, Berger M E, Ricks R C. Early dose assessment in criticality accidents. Health Phys 2001; 81:446-9; Goans R E, Holloway E C, Berger M E, Ricks R C. Early dose assessment following severe radiation accidents. Health Phys 1997; 72:513-8) for radiation dosimetry, and has been used for peripheral blood (Amundson S A, Bittner M, Meltzer P, Trent J, Formace A J, Jr. Biological indicators for the identification of ionizing radiation exposure in humans. Expert Rev Mol Diagn 2001; 1:211-9; Nakamura N, Miyazawa C, Sawada S, Akiyama M, Awa AA. A close correlation between electron spin resonance (ESR) dosimetry from tooth enamel and cytogenetic dosimetry from lymphocytes of Hiroshima atomic-bomb survivors. Int J Radiat Biol 1998; 73:619-27) and fingerstick capillary blood (Langlois R G, Nisbet B A, Bigbee W L, Ridinger D N, Jensen R H. An improved flow cytometric assay for somatic mutations at the glycophorin A locus in humans. Cytometry 1990; 11:513-21; Prasanna P G, Blakely W F. Premature chromosome condensation in human resting peripheral blood lymphocytes for chromosome aberration analysis using specific whole-chromosome DNA hybridization probes. Methods Mol Biol 2005; 291:49-57). It has good dose coverage (at least 0.5 to 5 Gy), and the biomarker remains stable for many weeks post exposure. A disadvantage is that the lymphocytes need to be cultured, a process which takes ~72 hours; however, as described herein, the process can be made fully automatic. A major advantage of the system is that the radiation specificity of the assay is excellent. Cellular proliferation and the scoring of micronuclei/nucleoplasmic bridges in bi-nucleate cells ensures that what is scored reflects damage to circulating lymphocytes, as opposed to the background level of micronuclei present in mono-nuclear lymphocytes. In addition, the system is amenable to high-throughput automation; in fact, there have been several attempts at partial automation (Hande M P, Azizova T V, Geard C R, Burak L E, Mitchell C R, Khokhryakov V F, et al. Past exposure to densely ionizing radiation leaves a unique permanent signature in the genome. Am J Hum Genet. 2003; 72:1162-70; Golub T R, Slonim D K, Tamayo P, Huard C, Gaasenbeek M, Mesirov J P, et al. Molecular classification of cancer: class discovery and class prediction by gene expression monitoring. Science 1999; 286:531-7; Bittner M, Meltzer P, Chen Y, Jiang Y, Seftor E, Hendrix M, et al. Molecular classification of cutaneous malignant melanoma by gene expression profiling. Nature 2000; 406:536-40), including the commercially available Metafer system (described below; Golub T R, Slonim D K, Tamayo P, Huard C, Gaasenbeek M, Mesirov J P, et al. Molecular classification of cancer: class discovery and class prediction by gene expression monitoring. Science 1999; 286:531-7). However the throughput of such systems is at most a few hundred samples per day, far below what is targeted for high throughput as described herein.

γH2AX foci in lymphocytes: William Bonner and colleagues at the NCI were the first to point out (Amundson S A, Bittner M, Formace A J, Jr. Functional genomics as a window on radiation stress signaling. Oncogene 2003; 22:5828-33) that phosphorylation of the histone H2AX (known as γ-H2AX) occurs at sites of DNA double-strand breaks (DSB). γ-H2AX can be measured with an antibody raised to the phosphorylated C-terminal peptide of H2AX, and can be detected with excellent sensitivity using both flow and in-situ image analysis (Amundson S A, Formace A J, Jr. Monitoring human radiation exposure by gene expression profiling: possibilities and pitfalls. Health Phys 2003; 85:36-42; Formace A J, Jr., Amundson S A, Do K T, Meltzer P, Trent J, Bittner M. Stress-gene induction by low-dose gamma irradiation. Mil Med 2002; 167:13-5). Because ionizing radiation is an efficient inducer of DSB, most the early research on γ-H2AX has been done with ionizing radiation (Amundson S A, Formace A J, Jr. Monitoring human radiation exposure by gene expression profiling: possibilities and pitfalls. Health Phys 2003; 85:36-42; Formace A J, Jr., Amundson S A, Do K T, Meltzer P, Trent J, Bittner M. Stress-gene induction by low-dose gamma irradiation. Mil Med 2002; 167:13-5). The fraction of H2AX that is phosphorylated is proportional to the number of induced DSB, with about 0.03% of the H2AX becoming phosphorylated per DSB. A normal human lymphocyte contains about 6×106H2AX molecules, so about 2000H2AX molecules are phosphorylated per DSB, indicating that the signal is highly amplified (Amundson S A, Bittner M, Formace A J, Jr. Functional genomics as a window on radiation stress signaling. Oncogene 2003; 22:5828-33). The γ-H2AX system well complements the micronucleus system as a radiation biodosimeter (Amundson S A, Formace A J, Jr. Gene expression profiles for monitoring radiation exposure. Radiat Prot Dosimetry 2001; 97: 11-6) because a) cells do not have to be cultured for the assay, b) the high-sensitivity and automation potential of the antibody-based assay, c) the γ-H2AX foci appear with their maximum value within about 30 minutes of irradiation (Amundson S A, Bittner M, Formace A J, Jr. Functional genomics as a window on radiation stress signaling. Oncogene 2003; 22:5828-33), and d) DSB and thus γ-H2AX are formed linearly with dose from very low to extremely high (>10 Gy) doses (Amundson S A, Formace A J, Jr. Monitoring human radiation exposure by gene expression profiling: possibilities and pitfalls. Health Phys 2003; 85:36-42). The disadvantage of the system as a radiation biodosimeter is the decrease of the signal with time after exposure. From the data available to this point, it seems clear that the assay is practical at least up to 24 hours post exposure (Amundson S A, Bittner M, Meltzer P, Trent J, Formace A J, Jr. Induction of gene expression as a monitor of exposure to ionizing radiation. Radiat Res 2001; 156:657-61). Studies for γ-H2AX foci in human lymphocytes are provided in examples below.

Micronuclei in blood reticuloctyes: During the formative stages of red blood cell production, chromosomal damage can manifest in the form of micronuclei. In humans these cells are generally rapidly cleared in the spleen, but an increased yield of micronucleated reticulocytes provides an independent means of assessing radiation exposure over a relatively short (1-3 days) interval post exposure (Ward B C, Childress J R, Jessup G L, Jr., Lappenbusch W L. Radiation mortality in the Chinese hamster, *Cricetulus griseus*, in relation to age. Radiat Res 1972; 51:599-607., Smolewski P, Ruan Q, Vellon L, Darzynkiewicz Z. Micronuclei assay by laser scanning cytometry. Cytometry 2001; 45:19-26., Grace M B, McLeland C B, Gagliardi S J, Smith J M, Jackson W E, 3rd, Blakely W F. Development and assessment of a quantitative reverse transcription-PCR assay for simultaneous measurement of four amplicons. Clin Chem 2003; 49:1467-75; Evans H J, Neary G J, Williamson F S. The relative biological efficiency of single doses of fast neutrons and gamma-rays on *Vicia faba* roots and the effect of oxygen. Part II. Chromosome damage: the production of micronuclei. Int J Radiat Biol 1959; 1:216-29; Fenech M, Holland N, Chang W P, Zeiger E, Bonassi S. The HUman MicroNucleus Project—An international collaborative study on the use of the micronucleus technique for measuring DNA damage in humans. Mutat Res 1999; 428: 271-83; Liu R H, Yang J, Lenigk R, Bonanno J, Grodzinski P. Self-contained, fully integrated biochip for sample preparation, polymerase chain reaction amplification, and DNA microarray detection. Anal Chem 2004; 76:1824-31). The assay reflects damage to cells in the bone marrow, whereas micronuclei in lymphocytes predominantly reflect damage in the peripheral circulation. These reticulocytes do not need to be cultured, as do the lymphocytes, and thus can provide a "same-day biodosimeter". A gradient-based separation technique can be used for the blood samples, whereby the reticulocytes are separated. Accordingly, the reticulocyte assay can share a single sample with the lymphocyte assays, increasing the information potential of a given sample.

Micronuclei in exfoliated buccal or urinary bladder cells: Cells in renewable tissues outlive their usefulness and are discarded and replaced continuously. Following exposure to ionizing radiation during their proliferative pre-differentiation phase, such cells are exfoliated from their epithelial origin and may manifest the consequences of chromosomal damage in the form of micronuclei (Liu R H, Yang J, Lenigk R, Bonanno J, Zenhausern F, Grodzinski P. Fully integrated microfluidic biochips for DNA analysis. Int J Comput Eng Sci 2003; 4:145-50; Rogakou E P, Pilch D R, Orr A H, Ivanova VS, Bonner W M. DNA double-stranded breaks induce histone H2AX phosphorylation on serine 139. J Biol Chem 1998; 273:5858-68). Exfoliated cells from the bladder appear in urine while buccal cells can be collected from the lining of the oral cavity. These exfoliated cells provide an indication of exposure to chromosome damaging agents in the form of enhanced frequencies of micronucleated cells (Pilch D R, Sedelnikova O A, Redon C, Celeste A, Nussenzweig A, Bonner W M. Characteristics of gamma-H2AX foci at DNA double-strand breaks sites. Biochem Cell Biol 2003; 81:123-9; MacPhail S H, Banath J P, Yu T Y, Chu E H, Lambur H, Olive P L. Expression of phosphorylated histone H2AX in cultured cell lines following exposure to X-rays. Int J Radiat Biol 2003; 79:351-8; Wolfram R M, Budinsky A C, Palumbo B, Palumbo R, Sinzinger H. Radioiodine therapy induces dose-dependent in vivo oxidation injury: evidence by increased isoprostane 8-epi-PGF(2 alpha). J Nucl Med 2002; 43:1254-8). Here again these cells are not capable of progressing through the cell-cycle and thus have the potential to provide a "same-day" radiation biodosimeter.

An overview of the automated processing steps begins with loading blood samples into a centrifuge, which will isolate the cell layer (e.g. lymphocyte) of interest. Next, the cells of interest are transferred from the centrifuge to an incubator. In transit, half of each sample receives a prescribed radiation exposure, providing a positive control. Within the incubator, the samples are deposited into wells on multiwell plates. A series of automated liquid processing steps follow, before the cells are passed on to an imaging stage. Samples are imaged with a unique steered-image compound microscope specifically designed for high throughput, through the use of fast sensors and by minimizing mechanical stage motions. High speed image analysis routines analyze the images for various indicators of radiation exposure.

In some embodiments, the device also analyzes other tissues, such as buccal cells and exfoliated bladder cells from urine.

Five basic Modules are summarized below, and illustrated in FIG. 1. It is noted that specific details of the Modules may vary in different embodiments. The Modules include: a centrifuge module 1, a cell recognition/harvest module 2, with a lymphocyte/monocyte pre-screening system; a mini-irradiator module 3; a plate handling/liquid handling module 4; and. an image acquisition/processing module 5.

The centrifuge module 1 and cell recognition/harvest module 2 are each served by a turntable-based transport system 6 and an SCARA robot 7. Modules 3-5 are served by a gantry robot 8 and a pick-and-place robot 9. Samples are separated in one or more centrifuges 10 which are mounted on the turntable-based transport system 6. Preferably, multiple centrifuges 10 operating on the turntable-based transport system 6 allow multiple batches of blood samples to simultaneously undergo centrifugation, while at the same time, a processed batch is conveniently harvested, removed, and replaced by new blood samples.

When a centrifuge 10 stops, the rotor (not shown) is lifted into the cell recognition/harvest module 2. Two or more parallel CCD camera systems 11 precisely determine the position and thickness of the separated lymphocyte (or other cell type) layer. In the embodiment illustrated in FIG. 1, four parallel CCD cameras 11 are shown. The thickness of the lymphocyte (or other cell type) layer acts as a pre-screening device to immediately identify individuals who received extremely high doses.

Next, guided by the CCD cameras 11, a visual servoed punctuator unit 12 precisely harvests the lymphocytes (or other cells). Half of the sample is then passed through the mini-irradiator module 3, the other half is not, and the two samples are deposited in adjacent wells in a multi-well plate inside the plate handling/liquid handling module 4. Here, three quickchange end effectors 13 are designed to perform various liquid handling steps in the wells, before the cell samples proceed to the image acquisition/processing module 5.

Certain differences between a first embodiment and a second embodiment of the devices are dictated by the available blood sample volume, and the target throughput. In the second embodiment of the device, cell samples will be transported to the wells (one via the irradiator, the other not) while still in their capillary tubes, at which point the tubes will be cut, the unwanted segments discarded, and the desired cells flushed into appropriate wells.

Figure 2:
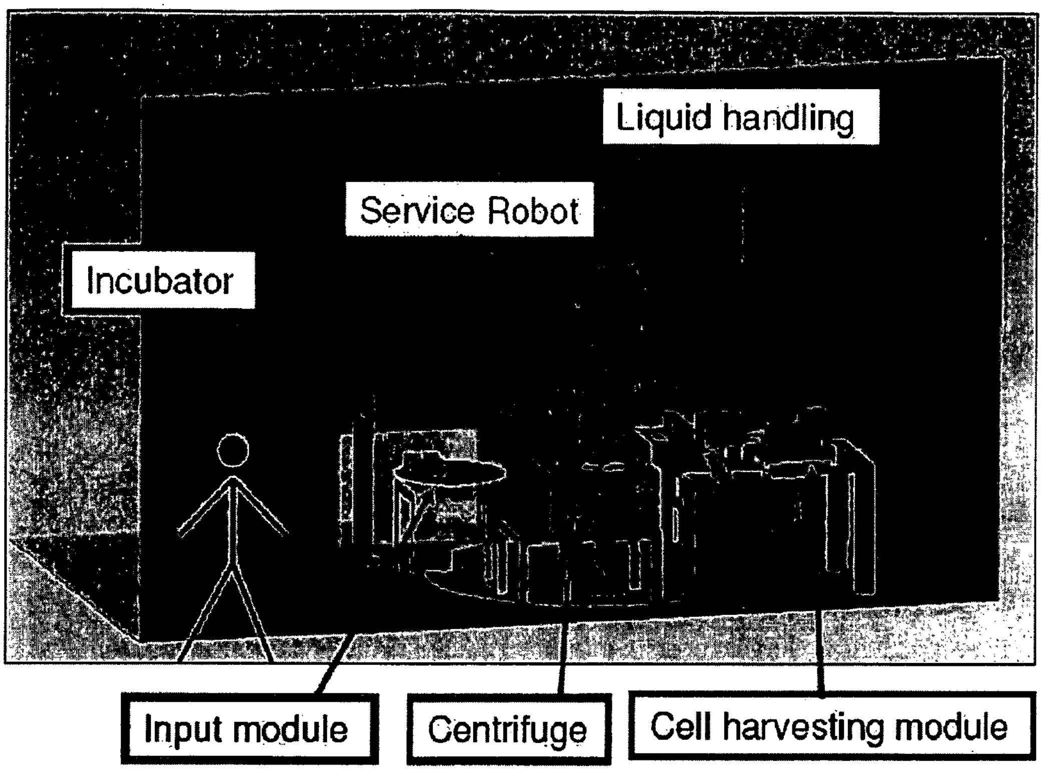
FIG. 2. illustrates a biodosimetry workstation in accordance with one embodiment of the invention.
Figure 3:
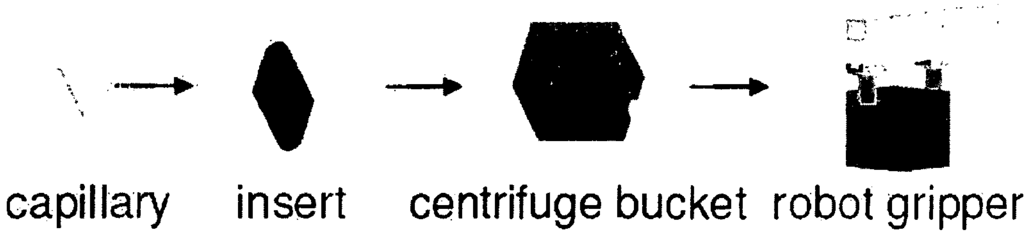
FIG. 3 depicts the sample hierarchy in accordance with an embodiment of the invention.

In one embodiment, illustrated in FIGS. 2 and 3, the system is designed to process blood samples collected into bar-coded plastic capillary tubes 31 at the emergency site using a finger or heel stick. The capillaries are then transported in inserts 32 to the biodosimetry workstation (FIG. 2). After having been filled with inserts, centrifuge bucket 33 is loaded into the automation system by the operator 21 through a safety barrier 22. At this point the bucket 33 is handled by a robot gripper, 34 of service robot 23, as illustrated. Samples follow an unmanned series of operations that automate multiple biological assays in order to assess the radiation exposure. In some embodiments, a first assay is effective during the first 1-2 days, post irradiation, and a second assay is effective at longer times.

Figure 4:
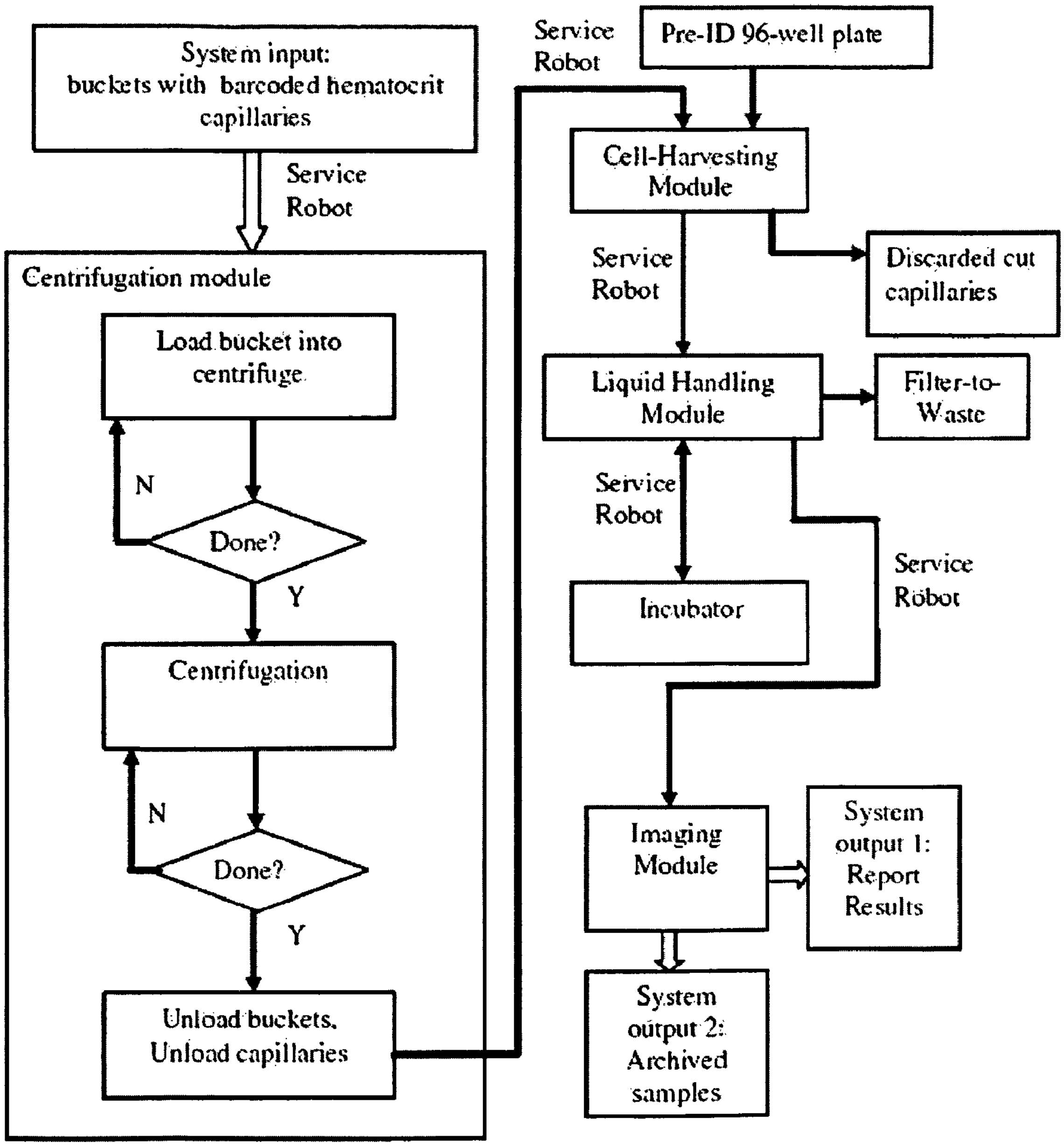
FIG. 4 depicts a process flow diagram in accordance with an embodiment of the invention.
Figure 5:
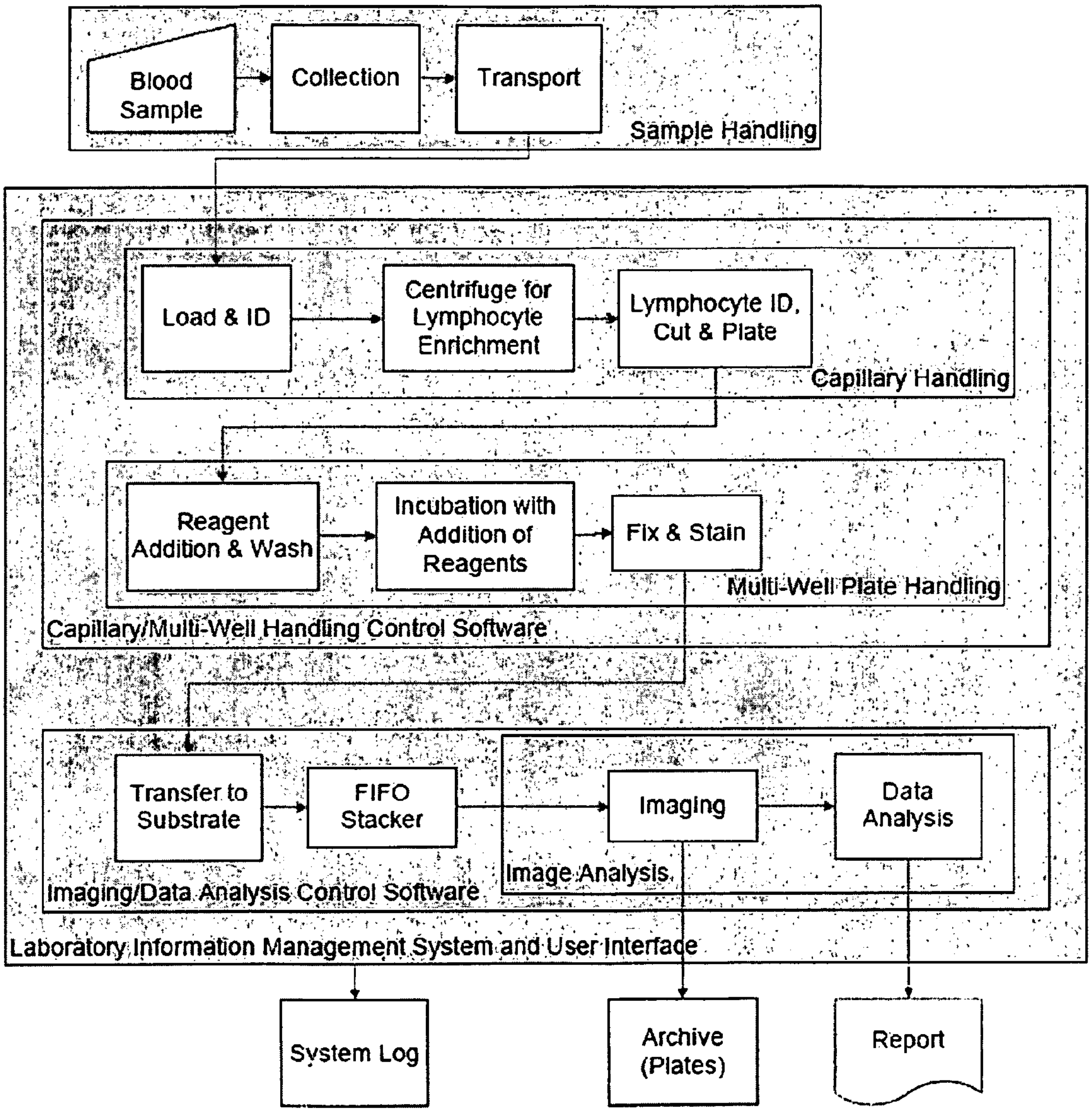
FIG. 5. shows a flow chart of a biodosimetry workstation in accordance with an embodiment of the invention.
Figure 6:
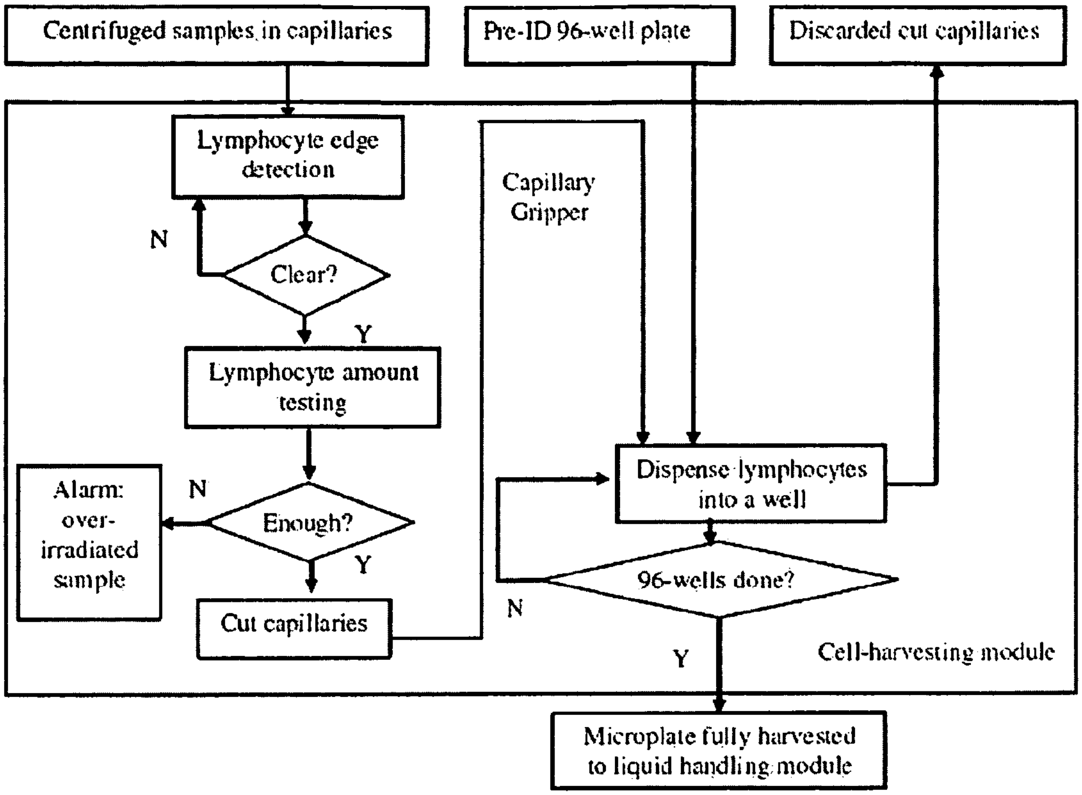
FIG. 6 shows a flow chart of a cell harvesting module in accordance with an embodiment of the invention.

In some embodiments, blood samples enter the automation system via an input module 24. The service robot 23 moves the centrifuge bucket(s) 33 from the input module 24 to the centrifuge 25. Referring now to FIG. 4, the centrifuge bucket is loaded into the centrifuge at step 41. After separation of white blood cells (WBC) and red blood cells (RBC), the centrifuged samples are unloaded 41 and transferred 42 to the cell-harvesting module 26 by the service robot 23 using the robot gripper 34. Using a capillary gripper (not shown) that prevents the lymphocyte band from being disrupted, each capillary 31 is removed from the insert 32 and the samples are then identified one by one using a barcode-reader (not shown). Upon completion of the identification, the capillary 31 is imaged 44 by a CCD system in order to detect the separation layer between RBC and the rest of the sample. Then a laser system is triggered to cut the capillary thus separating the sample into two parts one of which is discarded 43, namely the one with RBC. However, before performing the cut, the sample is imaged by the CCD system also for outputting an early assessment of radiation exposure. Referring now to FIG. 6, the thickness of the lymphocyte band is measured 61 and an alarm signal is given 62 in output if the value is low.

Figure 7:
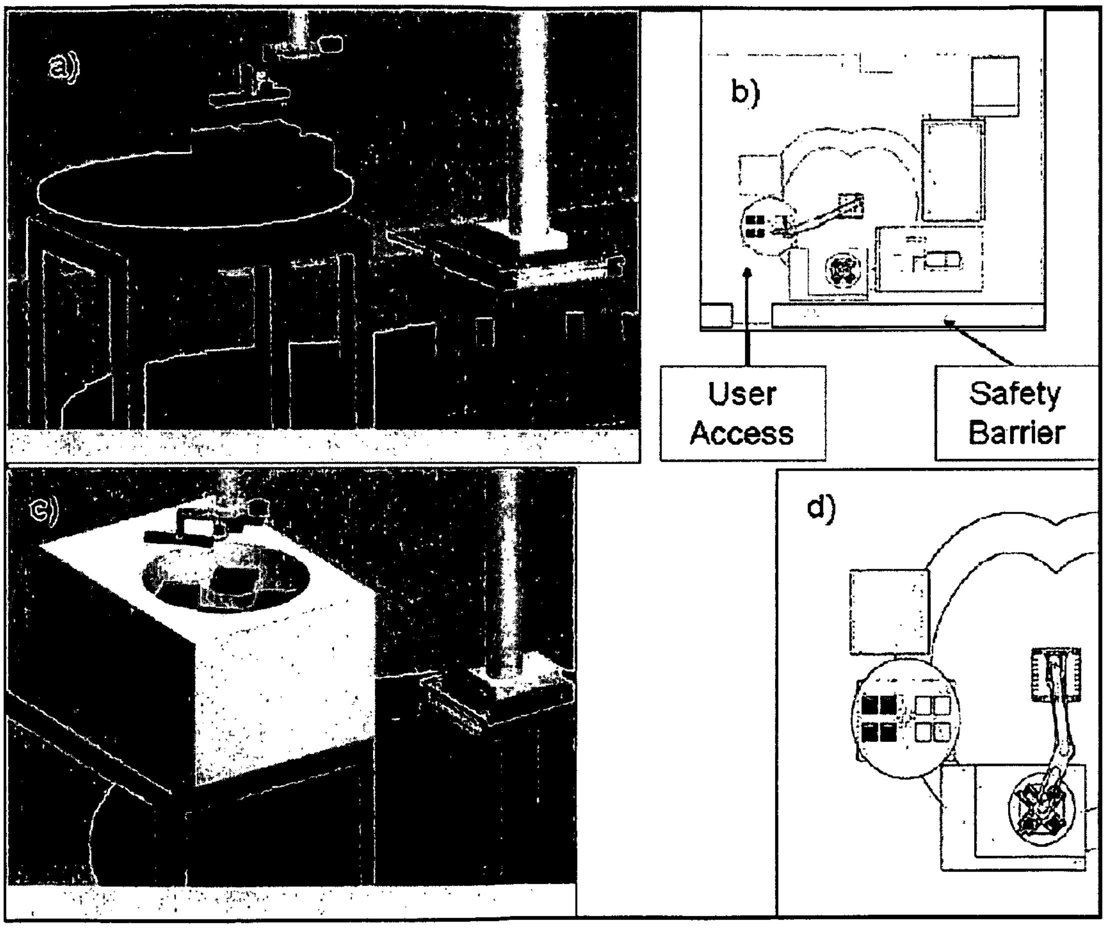
FIG. 7 illustrates an embodiment of an input module and centrifuge module in accordance with an embodiment of the invention.

One embodiment of an input module 24 is shown in FIG. 7. The input module 24, in this embodiment, can handle four centrifuge buckets 33 at the pick location of the service robot 23.

In this embodiment, four centrifuge buckets are filled with three inserts, each carrying 44 capillaries, for a total batch of 528 capillaries per centrifugation cycle. When the centrifugation ends, the service robot 23 transfers the empty centrifuge buckets back onto a stage 71 of the input module 24 after capillaries have been transferred to the cell-harvesting module. The stage 71 is also responsible for simultaneously i) moving the used centrifuge buckets (without capillaries) out of the system and ii) introducing a new set of centrifuge buckets (filled with capillaries) by performing a 180° rotation. This ensures continuity of the input to the automatic system. The input module 24 serves as a point of interface with the human user 21 who is separated by the automation system by a safety barrier 72.

Figure 8:
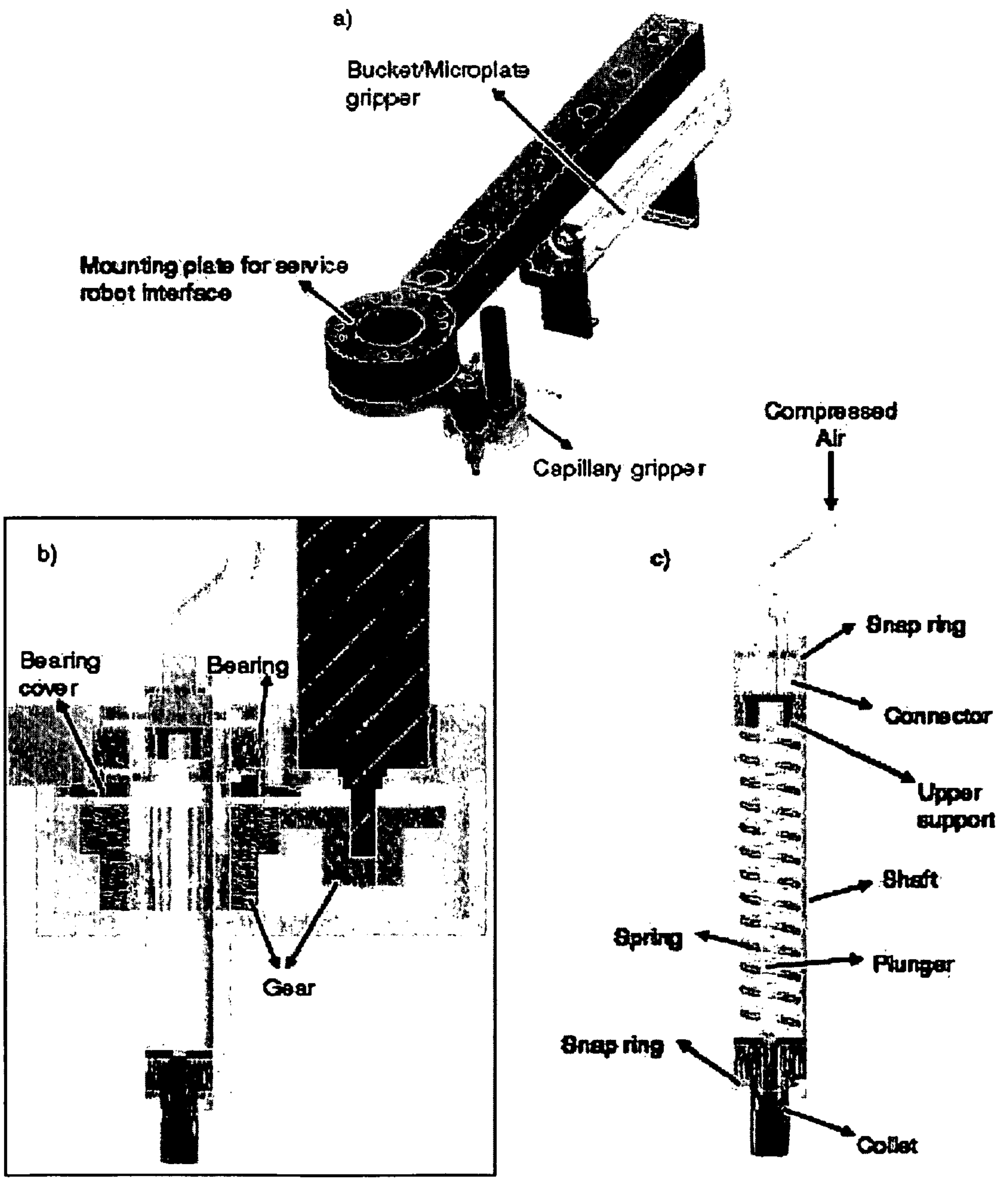
FIG. 8 depicts features of a service robot manipulating arm in accordance with an embodiment of the invention.

The service robot (for example, model RS80 SCARA from Staubli) is responsible for moving the centrifuge buckets 33, one by one, from the input stage 71 to the centrifuge module 1. As shown in FIG. 8*a*, the arm 81 of the service robot 23 can be fitted with a custom-made link endowed with two custom grippers: a capillary gripper 82 and a gripper 83 for handling of buckets and microplates. The capillary gripper 82, as shown in FIGS. 8*b* and 8*c* can be composed of a passive spring-plunger-collet unit 84 and of an active gear-motor-shaft unit 85. The former is preferably adapted to grip the capillary 31 without the use of any motor. The latter is responsible for the rotation of the capillary 31 during cutting in order to guarantee an even distribution of the power, thus minimizing thermal effects and contamination generated by the laser-based cutting.

In one embodiment, the bucket/microplate gripper 83 is composed of a pneumatically-actuated two-jaw unit and two miniature self-contained photoelectric sensors (not shown), for example two 06 38F from Banner Engineering Corp. Each jaw is composed of two sections: one for gripping the bucket 33 and one for gripping a microplate. In a preferred embodiment, the former is a custom-made jaw that seats into the side slots of the bucket when grip takes place. The latter is a rubber-padded jaw that grips microplates.

The centrifuge 25 is equipped with an electromechanical clutch that locks the centrifuge rotor in place after it stops rotating. Optical sensors (not shown) detect the centrifuge rotor arm in order to provide a reference to the bucket/microplate gripper 83 when loading bucket 33 in centrifuge 25. The gripper 81 is preferably modular and lightweight.

In one embodiment, the gripper 81 employs a hollow structure allowing for the passage of both pneumatic and electrical lines. The link length can be easily changed without having to change the mechanical interface with service robot 23. The two grippers, capillary gripper 82 and bucket/microplate gripper 83, can be mounted independently on a flange of service robot 23. When a capillary 31 is gripped, the collet 85 slides onto the capillary 31. In one embodiment a built-in linear actuator of the service robot 23 performs this operation as a vertical move. The gripping operation ends when the capillary 31 comes into contact with the tip of the plunger 86. The plunger 86 prevents loss of lymphocytes after capillary 31 is cut. The plunger 31 is also provided with air-conductive channels that allow dispensing positive pressure, for example, compressed air 87, for transferring lymphocytes into the microplate well after the capillary 31 has been cut, i.e. after RBC have been removed.

After centrifugation, centrifuge buckets 33 are transferred to the cell-harvesting module 26 by the service robot 23 using the bucket gripper 83. The cell-harvesting module 26 obtains the lymphocytes from centrifuged blood samples.

Figure 9:
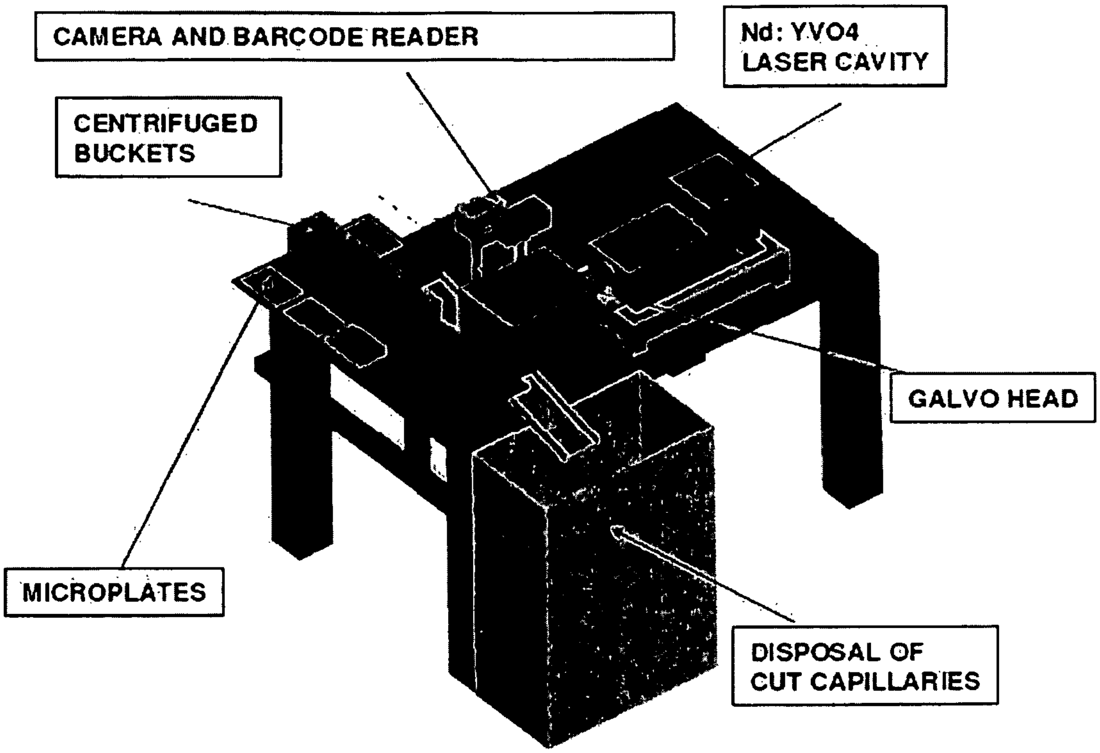
FIG. 9 depicts features of a cell harvesting module in accordance with an embodiment of the invention.
Figure 10:
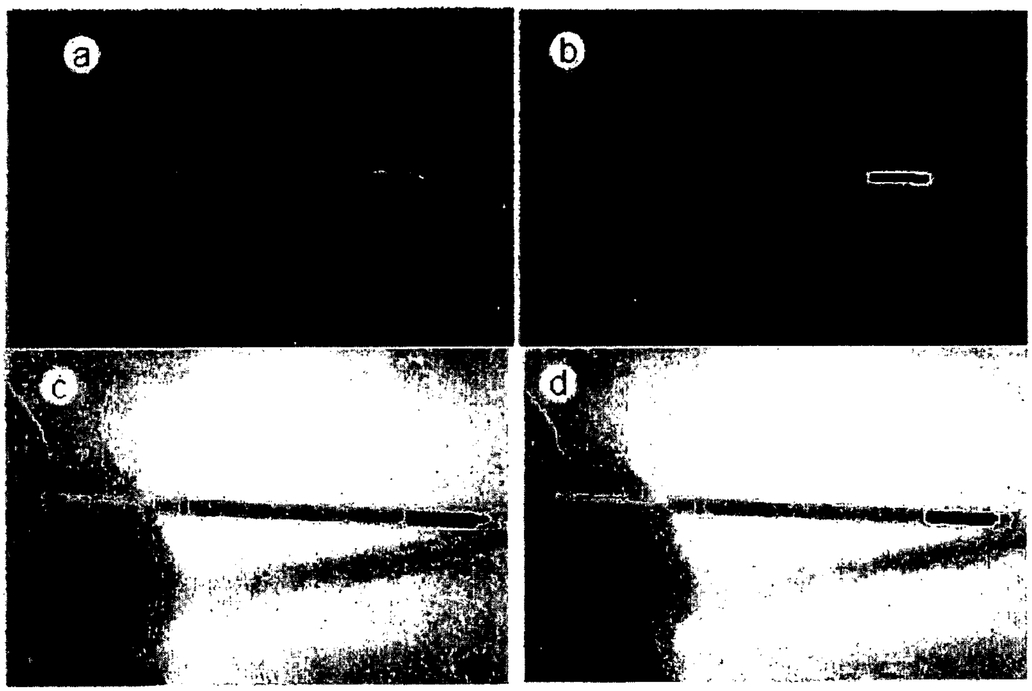
FIG. 10 illustrates image segmentation of a capillary as provided in an embodiment of the invention.
Figure 11:
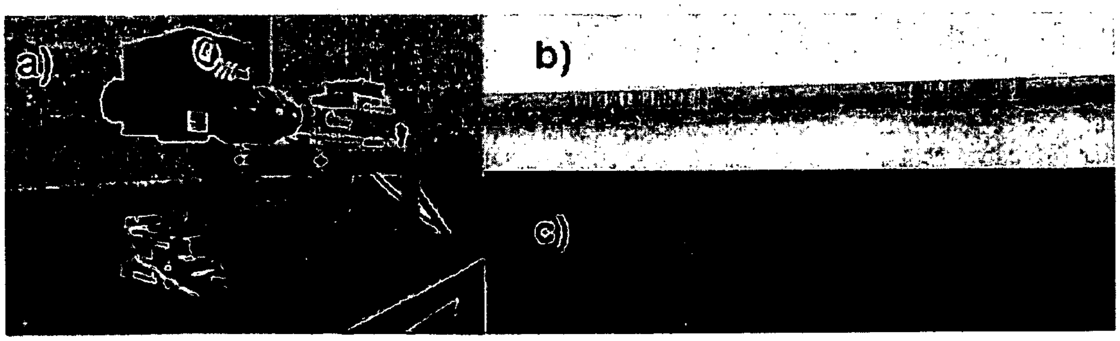
FIG. 11 depicts a laser system a in accordance with an embodiment of the invention.

In the embodiment illustrated in FIG. 9, the cell-harvesting module consists of a laser system with a galvo head 91, a barcode reader 92, for example, a Hawkeye 1525 from RVSI, an image sensor 93, and a holder for microplates and centrifuge buckets. The image sensor 93 provides for image segmentation of a capillary 31, (image segmentation of a capillary is illustrated in illustrated in FIG. 10), and a custom-made holder for microplates 94 and centrifuge buckets 33. In one embodiment, the laser system is an Osprey UV laser system from Quantronix. In some embodiments, the image sensor can be a CCD camera, such as a SONY XCL-U1000 or a CS3970CL from Toshiba-Teli, and the like. In some embodiments, the holder can host three stacks of twenty-one microplates 94, four centrifuge buckets 33, a microplate reference location, where the wells can be filled with lymphocytes, and a gravity-based capillary disposal unit 95.

Figure 12:
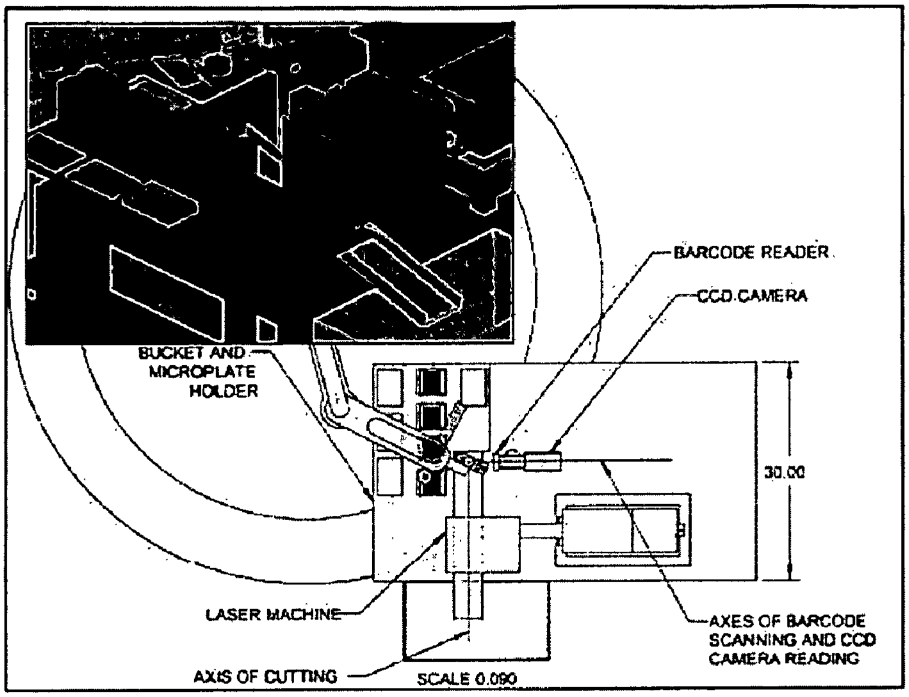
FIG. 12 illustrates further details of the cell harvesting module in accordance with an embodiment of the invention.
Figure 13:
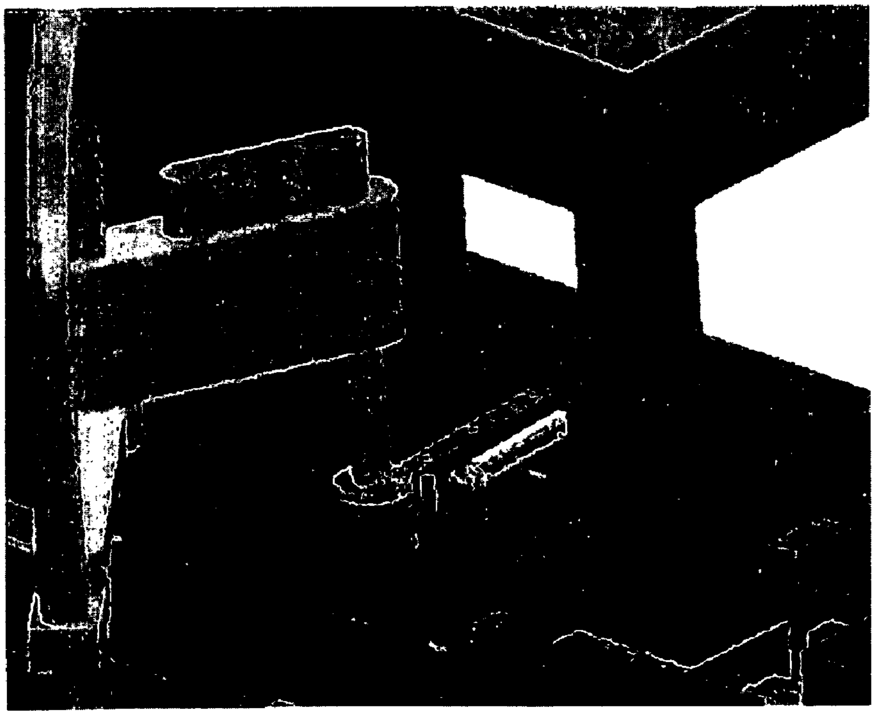
FIG. 13 illustrates a method of loading a liquid handling module in accordance with an embodiment of the invention.

The barcode reader 92 identifies the capillary 31 immediately before imaging by the image sensor 93. (In one embodiment, the capillaries 31 have been registered at the collection site.) The barcode reader 92 allows tracking of each sample after it has been transferred to a pre-id microplate. In one embodiment, shown in FIG. 12, the holder 121 supports i) three microplate stacks 122, each made of 21 microplates 94, ii) four centrifuge buckets 33, iii) a microplate reference location 123, where the wells are filled with lymphocytes, and iv) a gravity-based disposal unit 95.

The inputs to the cell harvesting module are centrifuged capillaries 31 in buckets 33 and sterile automation-compliant microplates 94. The outputs of the module are cut capillaries, which are disposed, and microplates 94 containing lymphocytes transferred from capillaries. In some embodiments, two software-outputs are the data associated with the barcode-based identification of the capillaries and the lymphocyte thickness estimation.

In one embodiment, the operation of the cell harvesting module is as follows: The bucket/microplate gripper 83 transfers a multi-well microplate 94 from a stack 122 to the reference location 123. The capillary gripper 82 is then deployed to service each capillary 31. The capillary 31 is moved in the field of view of the barcode reader 92 for identification. After reading, a vertical move is performed by the service robot 23 and the capillary 31 is moved in the field of view of an image sensor 93 for detection of the separation band between RBC and the rest of the sample. Upon detection of the band, a laser performs a cut while the capillary 31 is rotated by the rotary stage of the capillary gripper 82. In some embodiments, an estimation of the lymphocyte band thickness is also performed during imaging using the same machine vision system.

Upon cutting the capillary, the RBC-containing portion is disposed into a disposal unit 95 by means of gravity. In one embodiment, the cut capillary, containing lymphocytes and plasma, is moved above the well of the microplate in the reference location where lymphocytes are dispensed using the capillary gripper 82. The cut capillary is then disposed into a disposal container 95. During this operation, the service robot 23 moves downward while the collet 85 moves upward until the inner wall of the collet 85 is in contact with the outer surface of the capillary 31. When the foregoing contact ends, the capillary falls under gravity. The capillary will then be disposed into a waste container 95. Once a multi-well plate is fully harvested the service robot transfers it to the liquid handling module 27.

Figure 14:
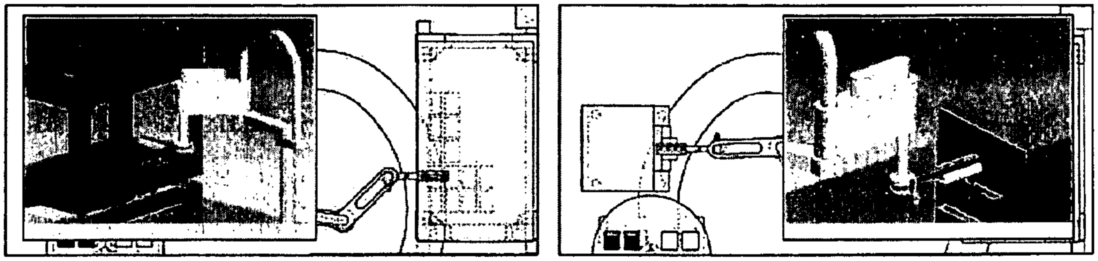
FIG. 14 illustrates a method of transferring a sample from the liquid handling module to a robotic incubator in accordance with an embodiment of the invention.
Figure 15:
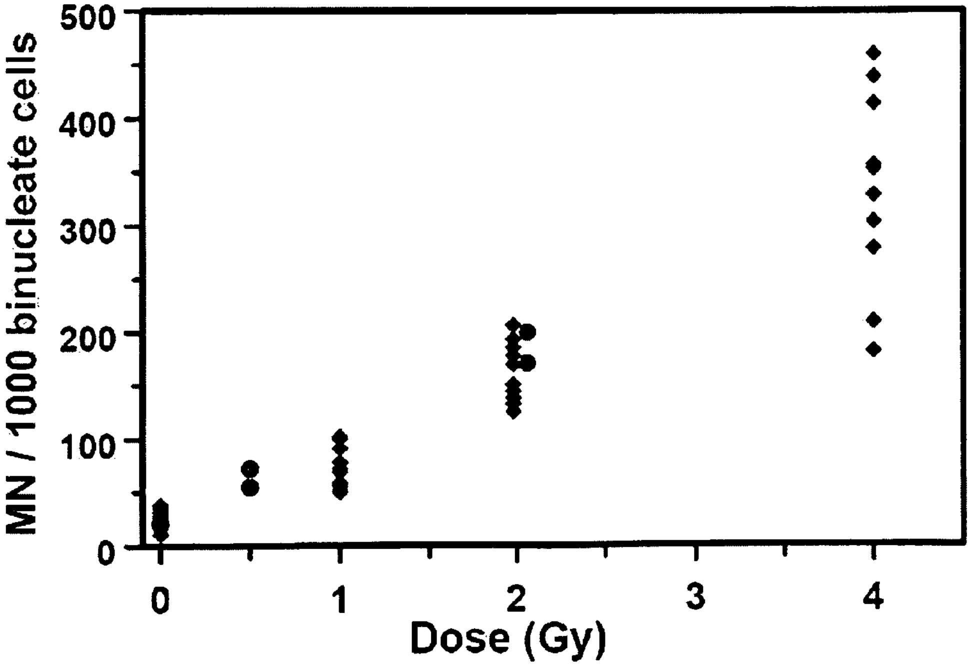
FIG. 15 compares radiation-induced micronucleus yields of conventional methods with yields obtained using systems and methods of the present invention.
Figure 16:
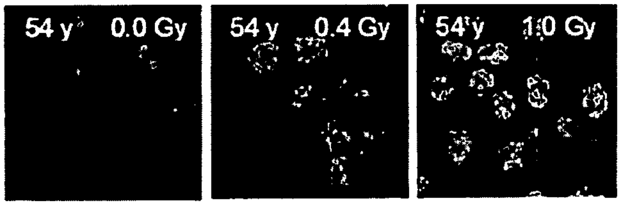
FIG. 16 illustrates results of dose-response studies of radiation induced γ-H2AX foci in peripheral blood lymphocytes.
Figure 16:
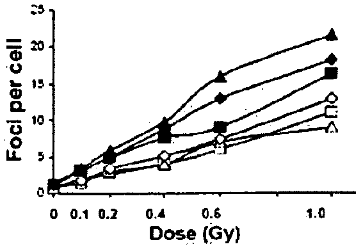

The liquid handling module 27, illustrated in FIGS. 13, 35, 38, and 39 preferably provides for the automation of both micronuclei and γ-H2AX assays for lymphocytes. In some embodiments, this is accomplished by a sequence of washes and reagent addition. In the case of a system designed for a throughput of 6,000 samples per day, using 96-well plates, with an assay duration time of approximately 72 hours, the incubator should be capable of storing at least 189 microplates simultaneously. In one embodiment, a robotic incubator capable of simultaneously hosting 220 microplates is used, namely the Liconic STX220. The system is integrated with the liquid handling module as shown in FIG. 14. For example, while running the micronucleus protocol, the service robot 23 places a microplate 94 in the lower left position on the deck of a liquid handling robot (not shown). After a wash and the addition of culture medium the microplate 94 is transferred to the incubator 28. The microplate 94 is then transferred back to the liquid handling robot for the addition of Cytochalasin-B. The microplate is then transferred into the incubator for the last incubation cycle. After the latter the protocol continues in the liquid handling module. In the case of γ-H2AX protocol, the initial operation consists of moving the microplate to the lower left position of the liquid handling robot. After a wash and the addition of the permealization buffer, the microplate 94 is transferred to a FIFO stacker (not shown) for 20 minutes. The microplate 94 then moves back to the liquid-handling robot where blocking reagents are added. The microplate 94 is then transferred back on to the FIFO stacker for other 30 minutes and then returns to the liquid-handling robot deck. After, the latter the protocol continues on the liquid handling robot.

In one embodiment, a fully-integrated liquid handling module, such as the commercially available Sciclone ALH 3000, is composed of a gantry system, an ultrasonic wash-station, a bulk-dispenser, a positive pressure unit, a filter-to-waste unit, a fixed-cannula array and a microplate gripper. The gantry system moves the microplate gripper, the fixed-cannula array (or the positive pressure unit) and the bulk dispenser at one of the specified microplate locations on the operation deck. The filter-to-waste unit collects the result of the well washes. The ultrasonic wash-station guarantees avoidance of reagent mixing by washing the metallic fixed-cannula array tips before changing reagent. The microplate gripper moves the plates or/and their lids across the deck. The bulk reagent dispenser is capable of continuously dispensing 10-2,500 ml of a single reagent simultaneously in eight wells with a coefficient of variation less than 2-3%.

The fixed-cannula array guarantees the same coefficient of variation and it is capable of dispensing up to 25 μl of a reagent simultaneously in 96 wells. The absence of disposable tips is intentional in the design of the system, as relying on this type of consumables could hamper the use of the disclosed system in an emergency condition. The use of metallic tips makes the system operation independent on the availability of disposable tips.

Centrifuge Module: In a preferred embodiment, separation of human lymphocytes or reticuloctyes is accomplished using the Ficoll Hypaque density-gradient method. Boyum A. Isolation of mononuclear cells and granulocytes from human blood. Isolation of monuclear cells by one centrifugation, and of granulocytes by combining centrifugation and sedimentation at 1 g. Scand J Clin Lab Invest Suppl 1968; 97:77-89. In its standard form, the technique employs a liquid density gradient medium of Ficoll 400 and sodium metrizoate or sodium diatrizoate solution; this standard procedure uses anticoagulated blood, which is diluted with a buffered solution, and then layered onto the medium. This preparation is then centrifuged to isolate mononuclear cells above the medium, and the cells harvested by pipetting from the liquid interface.

For the lymphocyte separation, the assays described herein can function with 50 μl of whole blood. In one embodiment, the blood can be transferred into a tube by capillary action, followed by 50 μl of the lymphocyte separating medium, and centrifuged at a speed of 40 g for 20 minutes at temperatures between 4° C. and 37° C. This yielded a good separation of the lymphocytes in the form of a clearly visible white band of lymphocytes with a count of 2100/μl of blood and about and 80% purity. The lymphocyte separating medium, which may be, for example, Ficoll Hypaque, with a density of 1.114 g/ml, which yielded better counts of lymphocytes and sharper bands upon separation as compared to a separation medium with a lower density (1.077 g/ml).

In one embodiment, the system is designed to use a two-speed configuration protocol, equivalent to an 8-minute centrifugation at 40 g followed by a 3-minute centrifugation at 160 g.

In one embodiment the system is designed to use a centrifugation speed of about 13,000 g and a centrifugation time of 5 minutes.

Figure 19:
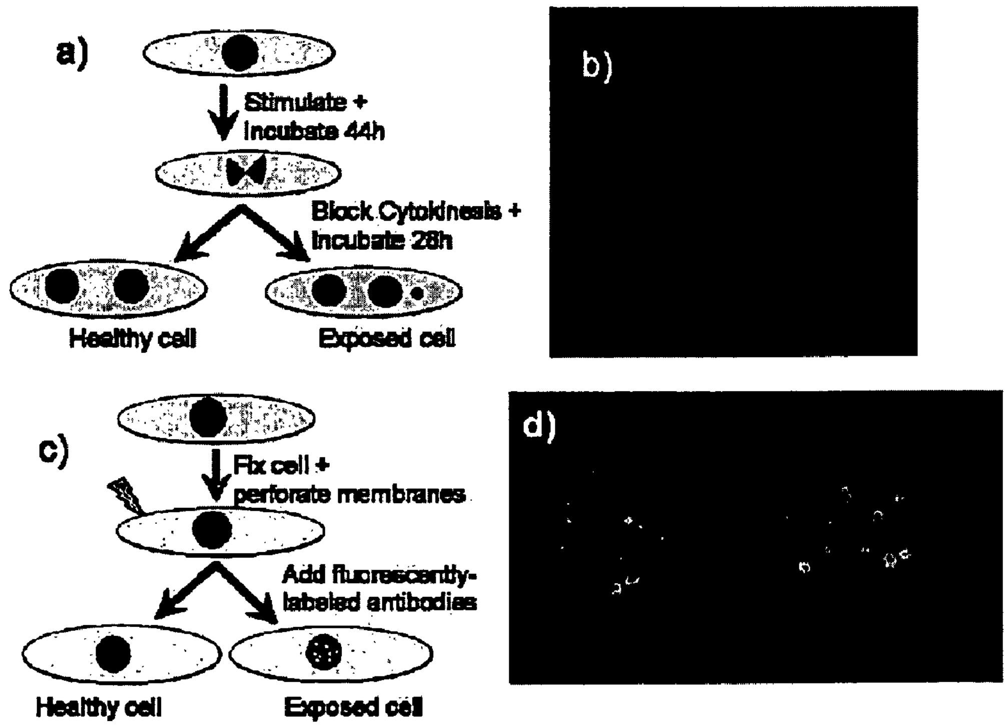
FIG. 19 shows a simplified flow diagram of a micronucleus assay process in accordance with an embodiment of the invention.

In one embodiment, depicted in FIG. 19, peripheral lymphocytes are separated from whole blood and stimulated to induce division. During division, the formation of cellular membrane is blocked resulting in binucleate cells. Chromosomes damaged by ionizing radiation lag in anaphase and will therefore not be included in the daughter nuclei during division, resulting in a small separate "micronucleus", as shown in FIG. 19*b*. The cells are then fixed and stained and can be automatically scored.

A major advantage of the system is that the scoring of micronuclei in bi-nucleate cells ensures that what is scored reflects damage to circulating lymphocytes, as opposed to the background level of micronuclei present in mono-nuclear lymphocytes. Thus the radiation specificity of the assay is excellent. This assay also has good dose coverage (at least 0.5 to 5 Gy), and the biomarker remains stable for months or even years post exposure [Pellmar T C, Rockwell S, and the Radiological/Nuclear Threat Countermeasures Working Group: Priority list of research areas for radiological nuclear threat countermeasures. Radiat Res 2005; 163:115-23]. A downside is that the lymphocytes need to be cultured, a process which takes about 72 hours during which the cells need to be kept at controlled temperature (37° C.), CO2 level (5%) and at high humidity. However, as described herein, the process can be made fully automatic.

Figure 17:
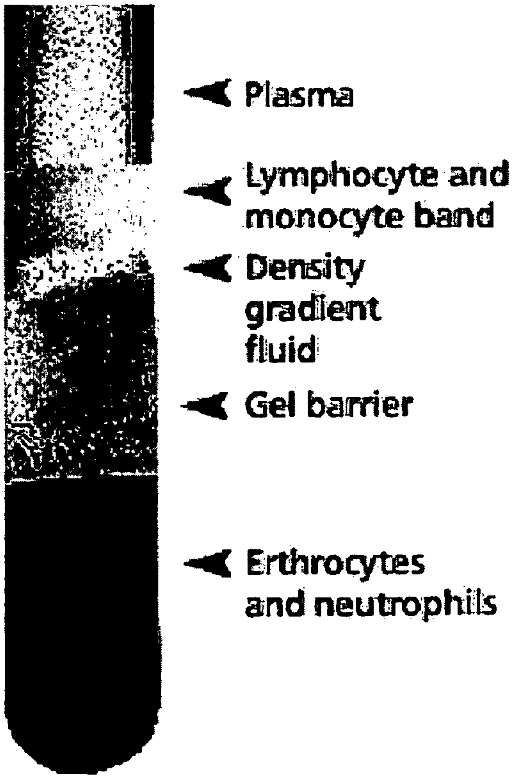
FIG. 17 illustrates a capillary tube for collection of whole blood and separation of mononuclear cells in accordance with an embodiment of the invention.

In an embodiment illustrated in FIG. 17, the procedure is considerably simplified and improved through the introduction of BD Vacutainer CPT tubes, which combine a blood collection tube 170 containing a sodium heparin anticoagulant, with a Ficoll Hypaque density gradient liquid 171 and a polyester gel barrier 172 which separates the two liquids. The blood separation media takes advantage of the lower density of mononuclear cells and of platelets to isolate them from whole blood. The isolation occurs during centrifugation when the gel portion of the media moves to form a barrier under the mononuclear cells and platelets, separating them from the denser blood components below, as shown here. The result is a very convenient, single tube system for the collection of whole blood and the separation of mononuclear cells, and which can be incorporated in a high-throughput robot-based centrifuge module, described below.

Figure 46:
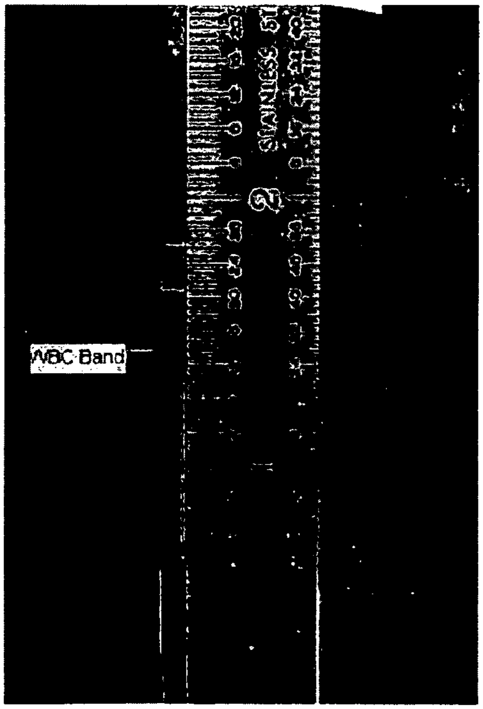
FIG. 46 shows a white cloudy band of lymphocytes separated out from whole blood in a glass Accutube.

In a preferred embodiment, a similar approach is used with capillary tubes instead of vacutainer tubes. Several approaches have been reported for separating blood in capillary tubes, including the quantitative buffy coat approach (Levine R A, Hart A H, Wardlaw S C. Quantitative buffy coat analysis of blood collected from dogs, cats, and horses. J Am Vet Med Assoc 1986; 189:670-3; Wardlaw S C, Levine R A. Quantitative buffy coat analysis. A new laboratory tool functioning as a screening complete blood cell count. Jama 1983; 249:617-20), in which a float is put in the tube to stretch out the linear dimensions of the separated components, and density-gradient enrichment (Choy W N, MacGregor J T. Density-gradient enrichment of newly-formed mouse erythrocytes. Application to the micronucleus test. Mutat Res 1984; 130:159-64; Kudoh E, Komatu T, Nakaji S, Sugawara K, Kumae T. Investigation of a new method for separation of neutrophils from a small volume of human blood. Nippon Eiseigaku Zasshi 1992; 47:650-7). In using automated optics to recognize the different bands (FIG. 46), it has been discovered that a Ficoll Hypaque density gradient liquid approach (as described above, but without the gel barrier), works well with capillary tubes. As discussed below, bands of interest are not drawn off by pipette, but rather the capillary tube is robotically cut at the appropriate location, and the required band simply flushed into the appropriate location in the multi-well plate.

Figure 20:
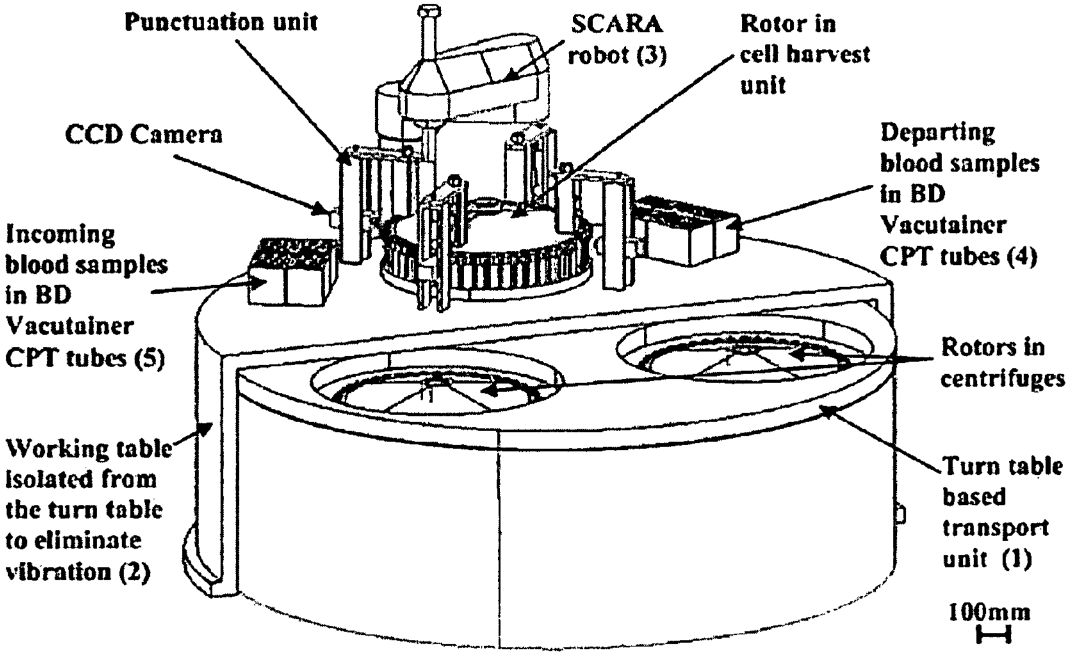
FIG. 20 illustrates an embodiment of a centrifuge module in accordance with an embodiment of the invention.

Multi-Rotor Centrifuge: In some embodiments, in order to achieve the target throughput, three or more centrifuge rotors, each with a holding capacity of 48 tubes, are used, as illustrated in FIG. 20. These centrifuge rotors are operated in a cascading manner to keep two rotors rotating at any given time and the third one for cell harvest and loading/unloading of the tubes. The rotor diameter is preferably about 0.5 meter with each tube in a slotted bucket (the slot enables the visual servoing control of the cell harvest process).

Each rotor in the centrifuge module preferably moves continuously through a three position loop. From a first position, the centrifugation process starts and proceeds for about 12 minutes. In a second position, another 12 minute spin is performed and the rotor stopped. A third position is the cell recognition position (see below). The rotor transporter is provides for movement of the centrifuge rotors 201 between the positions as described above. Preferably a turn-table based transport unit 202 is employed. Thus, a compact, rigid, and light weight device is provided to permit smooth transport of heavy (about 26 kg) centrifuge rotors, eliminate vibration in the cell recognition/harvest module from the large rotating centrifuges, and allow a closed loop feedback for the entire module to monitor the status of the rotors. Preferably it prevents scenarios such as a rotating centrifuge rotor being placed on the cell recognition/harvest module.

Accordingly, some embodiments use a transport system equipped with a turntable. FIG. 20 shows an embodiment of the centrifuge and cell recognition/harvest modules, wherein three rotor positions are arranged on a circle. In one embodiment, a rotary turntable transfer rotors to the next position every 12 minutes—the spin time.

When a rotor finishes its centrifugation process and arrives at the cell harvest position, a jack device, completely isolated from the turn table 202 to eliminate vibration, is used to elevate the rotor 201 to the level where the lymphocyte layer can be conveniently monitored and harvested (see cell recognition/harvest module, below). The jack includes a means of stabilizing the buckets of the centrifuge during cell harvesting. The centrifuge driving motor is used as an indexer during the harvesting stage. For vibration isolation, the cell recognition/harvest module is also placed on a working table that is isolated from the rotary turntable. A pick-and-place robot 204 with three degrees of freedom is used to remove used samples immediately after they are harvested, and reload tubes containing fresh samples into the empty buckets. After the cell harvest and loading/unloading processes are finished, the rotor is transferred again by the turntable to the first centrifuge position and a new batch started.

In one embodiment, the pick-and-place robot 204 comprises a SCARA (Selective Compliance Assembly Robot Arm) robot for the pick-and-place operations required for loading/unloading of the tubes. The degrees of freedom needed for the tube manipulation here are arm rotation, elbow rotation, and the vertical motion for the end-effector which will grasp the tube. SCARA robots represent a widely spread and relatively mature technology. Commercially available SCARA robots include the EPSON B- and E-series, the Intelligent Actuator IX series, the MekA-Nize Robotics MR series, and the IBM 7500 series. Because of their unique "elbow" motions, SCARA robots are ideal for applications which require fast, repeatable and articulate point-to-point movements such as loading/unloading, palletizing/de-palletizing and assembly. The high throughput and high repeatability requirements of the tube manipulation make the SCARA robot an ideal fit for this application.

Cell Recognition/Harvest Module: The automated removal of lymphocytes from the Vacutainer tubes represents a task that, traditionally, is done by experienced personnel using pipetting techniques. The robotic challenge largely arises from the uncertainties that exist during this process. After centrifugation, the whole blood sample is separated into multiple layers, and the position and thickness of the lymphocyte layer separated by the centrifugation process varies. The thickness of the lymphocyte layer of course decreases as the sample is withdrawn. In order to optimize lymphocyte harvesting, and to avoid taking cells from other layers, it is desirable to always keep the needle tip around the middle of the lymphocyte layer. This requires real-time tracking of the harvest tool (a punctuator needle) and the liquid interfaces. Therefore, for each tube, information about position and thickness of the lymphocyte layer needs to be quickly acquired and used as feedback to control the robotic manipulator during the pipetting process. It is natural to use a CCD-based vision sensor here, since it mimics the human sense of vision and allows for non-contact measurement. Visual servoing with better than 100 μm precision is now a well-established robotic control technique, integrating vision in feedback control loops (Georgiev A, Allen K P, Mezouar Y. Microbiotic crystal mounting using computer vision. In 2003 IEEE/RSJ International Conference on Intelligent Robots and Systems: (IROS 2003): proceedings: Oct. 27-31, 2003, Las Vegas, Nev. Piscataway, N.J.: IEEE; 2003. p. 4 v; Mezouar Y, Allen P K. Visual servoed micropositioning for protein manipulation. In Proceedings 2002 IEEE/RSJ International Conference on Intelligent Robots and Systems: IROS 2002, Sep. 30-Oct. 4, 2002, EPFL, Lausanne, Switzerland. Piscataway, N.J.: IEEE; 2002. p. 1766-77; Dewan M, Marayong P, Okamura A M, Hager G D. Vision-based assistance for ophthalmic microsurgery. Medical Image Computing and Computer-Assisted Intervention—Miccai 2004, Pt 2, Proceedings 2004; 3217:49-57; Kumar R, Kapoor A, Taylor R H. Preliminary experiments in robot/human cooperative microinjection. In 2003 IEEE/RSJ International Conference on Intelligent Robots and Systems: (IROS 2003): proceedings: Oct. 27-31, 2003, Las Vegas, Nev. Piscataway, N.J.: IEEE; 2003. p. 4 v; Lots J F, Lane D M, Trucco E, Chaumette F. A 2-D visual servoing for underwater vehicle station keeping. Proceedings of the 2001 IEEE Conference on Robotics and Automation. Seoul, Korea; 2001. p. 2767-72).

Figure 21:
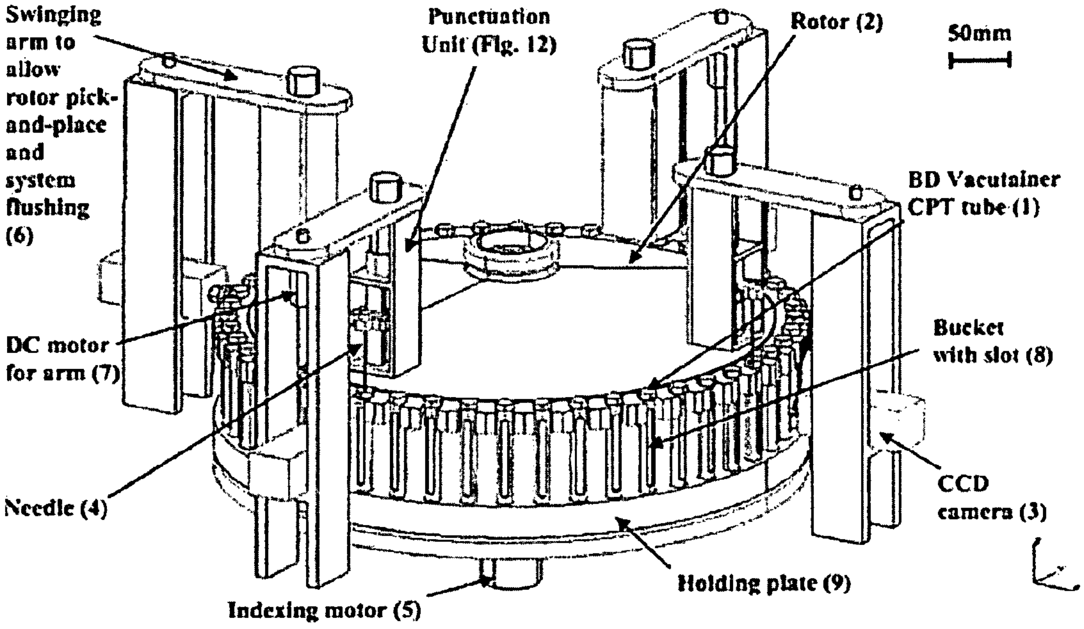
FIG. 21 illustrates further details of the centrifuge module in accordance with an embodiment of the invention.

In some embodiments, to achieve a system throughput of 6,000 samples per day, the cell recognition/harvest module is required to complete the cell transportation from tubes to a 96-well microplate in 12 minutes. FIG. 21 illustrates design features of certain embodiments used to achieve this goal.

In one embodiment, cell harvesting is performed in a Vacutainer tube 170 in the rotor 201 immediately after lifting the rotor from the centrifuge, thereby saving the extra time of taking 170 the tubes out of the rotor 201. Four sets of imaging sensors 211 and punctuating needles 212 are used to harvest cells in parallel, enabling four tubes to be processed simultaneously. After cell harvesting is completed at one position, a rotary indexing motor 213 indexes the rotor to the next position. In this way, the cell transfer speed required for each punctuator unit 214 is dramatically reduced to about 1 tube/min, including the time needed for system cleaning between two indexing positions. With this arrangement, 96 samples can be completed in 12 minutes. System cleaning is done by swinging an arm 215 by 90° using a DC motor 216 and flushing the entire system. When the robot brings in a rotor after centrifuge, the buckets 217 containing Vacutainers rest on a holding plate 218 with conforming dents, to provide better support for punctuating. The plate is indexed with the rotor by the indexing motor 213.

Figure 22:
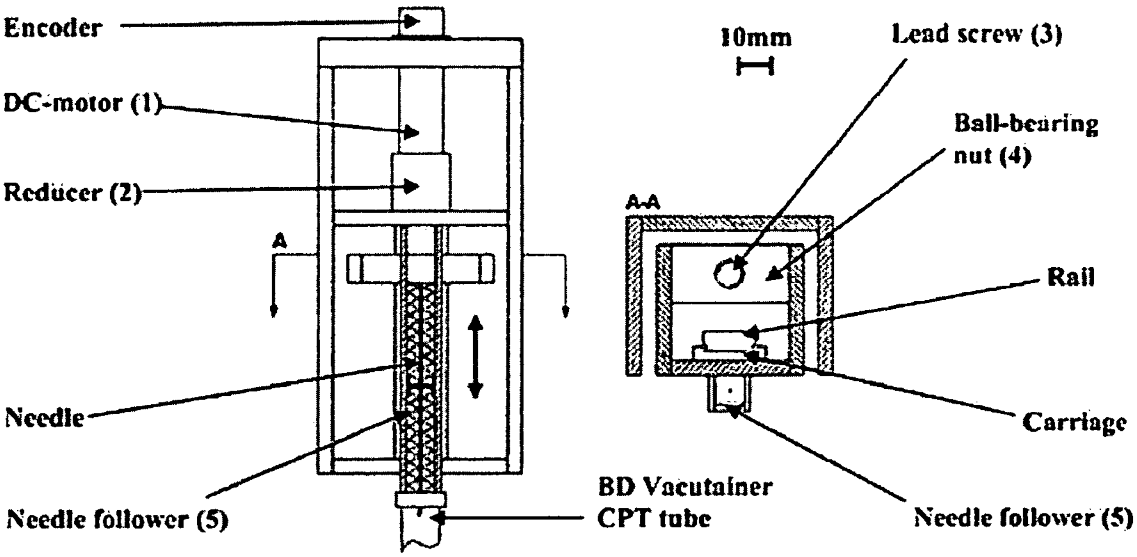
FIG. 22 illustrates details of a punctuation unit in accordance with an embodiment of the invention.

For cell pipetting, a high-strength needle 212 is used to puncture through the rubber lid of the Vacutainer tube 170, and to aspirate the separated lymphocytes under the guidance of the imaging sensor 211. As shown in FIG. 22, a DC motor 221 is used in conjunction with a reducer 222 to supply the driving force. A lead screw 223 and a preloaded ball-bearing nut 224 provide the linear motion needed for the punctuation and precise positioning.

Since the estimated travel is quite long (70 mm) compared to the very small diameter of the needle, a spring loaded follower 225 provides extra support to the needle.

A position-based servoing control (Hutchinson S, Hager G D, Corke P I. A tutorial on visual servo control. Ieee Transactions on Robotics and Automation 1996; 12:651-70; Hashimoto K. Visual servoing: Real time control of robot manipulators based on visual sensory feedback. In World Scientific Series in Robotics and Automated Systems. Vol 7. Singapore: World Scientific Press; 1993) is used, which is based on the computation of a Cartesian error, requiring modeling of the objects and a calibrated camera to obtain unbiased position estimation. Once the model is established, the controller is dramatically simplified. This makes position based control advantageous in applications where the geometric model of the target can be obtained (Weiss L E, Sanderson A C, Neuman C P. Dynamic Sensor-Based Control of Robots with Visual Feedback. Ieee Journal of Robotics and Automation 1987; 3:404-17). In one embodiment, the tube appears in a semi-definite fashion: with the same liquid layers in a fixed order, the only uncertainty is the position and thickness of the layers. Furthermore, the vision sensor is fixed in position, making for easy calibration. Considering the fact that many currently available robots already have an interface for accepting Cartesian velocity or incremental position commands, this structure provides set-point inputs to the joint-level controller of the robot (dynamic look-and-move).

Centrifuge/Band Recognition Modules: In a second embodiment of the device, the samples in their original hematocrit tubes are centrifuged, imaged with the image sensor for band recognition, and transported to the wells (one via the irradiator, the other not) while still in the hematocrit tubes, at which point the tubes are cut, the unwanted segments discarded, and the desired cells flushed into the appropriate well.

The centrifuges used in a second embodiment of the device can be physically much smaller, but spin faster than those used in other embodiments, because the samples are in hematocrit capillaries rather than in Vacutainer tubes. Hematocrit tubes are typically spun at 15,000 g for ~5 minutes in a 24-place rotor. In this configuration the second embodiment of the device uses 5 units, 4 spinning and one being robotically loaded and unloaded, to reach the design throughput.

In a third embodiment the capillaries are spun at high speed (13,000 g) in a rotor of larger capacity (about 100-600 capillaries).

After centrifugation, the sample is picked up and placed in an imaging station where the lymphocyte or other cell-type band is identified as before. One of two samples is then ready to be pushed into the irradiator as described below. Cell harvesting is completed by simply cutting the hematocrit tube to select the desired cells. Unwanted segments are discarded and the desired cells are flushed into the appropriate well.

This system, in which the sample is flushed directly from the hematocrit tube to the well, minimizes cell loss during transport.

Lymphocyte/Monocyte Pre-Screening Component: Optionally, once the bands in the Vacutainer/hematocrit tubes have been recognized by the CCD system, a quick "alarm" is provided should the lymphocyte/monocyte layer be sufficiently small to indicate a very large radiation dose. This is not a biodosimetry system per se, as a time series of lymphocyte counts are required for this purpose (Goans R E, Holloway E C, Berger M E, Ricks R C. Early dose assessment in criticality accidents. Health Phys 2001; 81:446-9; Goans R E, Holloway E C, Berger M E, Ricks R C. Early dose assessment following severe radiation accidents. Health Phys 1997; 72:513-8), but it will provide a rapid alarm of an immediately life threatening situation. For example, after a whole body dose of 5 Gy (which would not necessarily produce major early symptoms for several weeks (Hirama T, Tanosaki S, Kandatsu S, Kuroiwa N, Kamada T, Tsuji H, et al. Initial medical management of patients severely irradiated in the Tokai-mura criticality accident. Br J Radiol 2003; 76:246-53)), one would expect the lymphocyte count to be down by typically an order of magnitude after 4 or 5 days (Baranov A E, Guskova A K, Nadejina N M, Nugis V. Chemobyl experience: biological indicators of exposure to ionizing radiation. Stem Cells 1995; 13 Suppl 1:69-77). Thus, alarm criteria are set, in terms of the width of the separated lymphocyte/monocyte band: Any sample in which the lymphocyte/monocyte band width is smaller than this criterion produces in an immediate alarm, allowing that individual to be identified for potential emergency treatment.

Flow-Through Low-Activity 90Sr/90Y Mini-Irradiator Module: In some embodiments, in order to have a positive control for each individual, so that the effects of inter-individual variability in radiosensitivity are accounted for, a simple, small, low-activity $^{90}Sr/^{90}Y$ beta irradiator is used to irradiate half of each sample with a known dose, e.g., 1.8 Gy, before it is analyzed. This radioactive source was chosen because a) it has a very long half life (28 years), and b) it is primarily a beta emitter, which greatly reduces radiation safety issues, and c) the beta particles from the $^{90}Y$ decay are high energy, with sufficient range to allow uniform dose coverage.

Mini-Irradiator Module: In a first embodiment of the device, the basic design splits the cells from each sample as they are being transferred to 96-well plates. Half the cells from each individual flow in tubing through a small shielded cavity, where they are exposed to the radiation from an array of radioactive seeds arranged around the tube. To achieve the desired throughput, four parallel channels are used for blood flow, passing through a single irradiator.

In some embodiments, a 1.6 mm ID tubing (wall thickness 0.8 mm) is used to transfer the cells to and from the irradiator, at a velocity of 1.7 mm/sec. At the entrance of the irradiator, the tubing has a gradual increase in ID to 2.75 mm (with a wall thickness of 0.4 mm), to slow the cell flow speed through the irradiator by a factor of 3, to prolong the cell exposure time and thus reduce the amount of radioactivity required for the sources. The tube ID is gradually decreased again on exiting the irradiator. As the transit distance within the irradiator is less than 20 mm, this will not have a major effect on throughput.

Given the dose requirement of 1.8 Gy, an estimated four low-activity 4-mCi 90Sr/90Y seeds are evenly distributed around the tubing (the seed axis is 2.5 mm from the tube center) and will produce this dose (Rosenthal P, Weber W, Forster A, Orth O, Kohler B, Seiler F. Calibration and validation of a quality assurance system for 90Sr/90Y radiation source trains. Phys Med Biol 2003; 48:573-85) with a uniformity of better than 90%. These millimeter-sized 4-mCi $^{90}Sr/^{90}Y$ seeds are now in use for intravascular brachytherapy (Id.), and are readily and inexpensively available, from Bebig Isotopes or AEA Technology. An array of nine seeds has been configured which irradiates the blood passing through four tubes, in a 2×2 array. In some embodiments, the irradiator is calibrated using Fricke dosimeter solution.

In terms of radiation safety, at a distance of 10 cm from four 4 mCi seeds, the dose rate is 40 μGy/h with no shielding, entirely from bremsstrahlung (Florkowski T. Shielding for Radioisotope Bremsstrahlung Sources Sr90 Plus Y90. Int J Appl Radiat Isot 1964; 15:579-86). Shielding is accomplished using concentric plastic and lead cylinders, with wall thicknesses of ⅛" and 1" respectively, which diminishes the dose rate to well below radiation safety requirements. Thus, in one embodiment, the external dimension of the cylindrically-shaped irradiator is 75 mm (length)×68 mm (diameter) and it weighs just over 3 kg.

In the second embodiment of the device, all cell irradiations are done in sequence within one irradiator containing five seeds, rather than the four channels employed in the first embodiment of the device. This simplification is possible because of the different physical form of the sample, which is in a thin layer within a previously centrifuged hematocrit capillary moving inside a tube, rather than blood flowing through a tube. Thus, instead of a continuous flow, the target cells in the capillary are brought to the center of the irradiator and remain stationary for a few seconds. This increases the cell residence time close to the radioactive seeds, thus increasing the dose rate, and increasing the throughput. The target cell samples contained in a capillary are rapidly brought to the center of the Sr irradiator by the robotic manipulator. The sample stays at a position where the estimated dose rate is 23 Gy/min for just under 4 seconds to receive a total estimated dose of 1.8 Gy. The capillary tube is then displaced by the incoming sample. At this rate, the irradiator throughput meets a throughput rate of 15,000 individuals/15-hr day. Because only one channel (rather than four) is used here, the external dimensions of the irradiator, including shielding, are slightly smaller than that in a first embodiment of the device.

In some embodiments the irradiator is not present and no inter-individual calibration is done.

Automated Culturing of Lymphocytes: In a first embodiment, the entire assay will be conducted in-situ in multi-well plates. Because lymphocytes do not attach well to surfaces, multi-well plates are used in which the base of each well consists of a Millipore filter. Use of a filter pore size of 0.65 μm, far smaller than the lymphocytes, allows efficient medium removal by aspirating through the filter, whilst ensuring that no cells are lost during the aspiration. For the 96-well based platform, these filter-bottomed plates are commercially available from Millipore and medium removal through the filter works well, without loss of lymphocytes.

In another embodiment the aspiration is replaced by applying positive pressure to the top of the filter, pushing the liquid but not the lymphocytes through.

After the cells are fixed, a final aspiration assures that the lymphocytes will be in an approximate monolayer on the filter substrate, in the correct geometry for imaging. At this point the optimal imaging mode is from the top of the well, rather than from the bottom through the Millipore filters—because of poor optical transmission through the filter substrate. When imaging the cells, the microscope objective must be within a few millimeters of the cells, which can be achieved when imaging through the top by simply removing the walls of the plate. This can be readily accomplished as the walls and filter base are not strongly attached to each other. A robot-friendly automated system for removing the well walls has been configured and tested.

Because the entire micronucleus assay is carried out in-situ in multi-well plates, there are many plate and liquid handling tasks. Unlike the automated centrifuge and cell harvesting steps, automated plate and liquid handling are relatively mature technologies. Commercially available products include the Zymark Allegro/Staccato, the Qiagen BioRobot, Caliper LS Sciclone and the Gilson 925/940 workstations. While some components are appropriate and are adopted here, an entire system from these vendors is not appropriate for the invention described herein for the following reasons: 1) these systems are typically designed with "general purpose" in mind and therefore come with a moderate throughput and price premium and 2) using components from different vendors to form a system typically does not lead to an optimal solution and substantial customer software development is typically required. Our approach is to develop a dedicated system with optimized software to achieve high throughput and accuracy.

Figure 27:
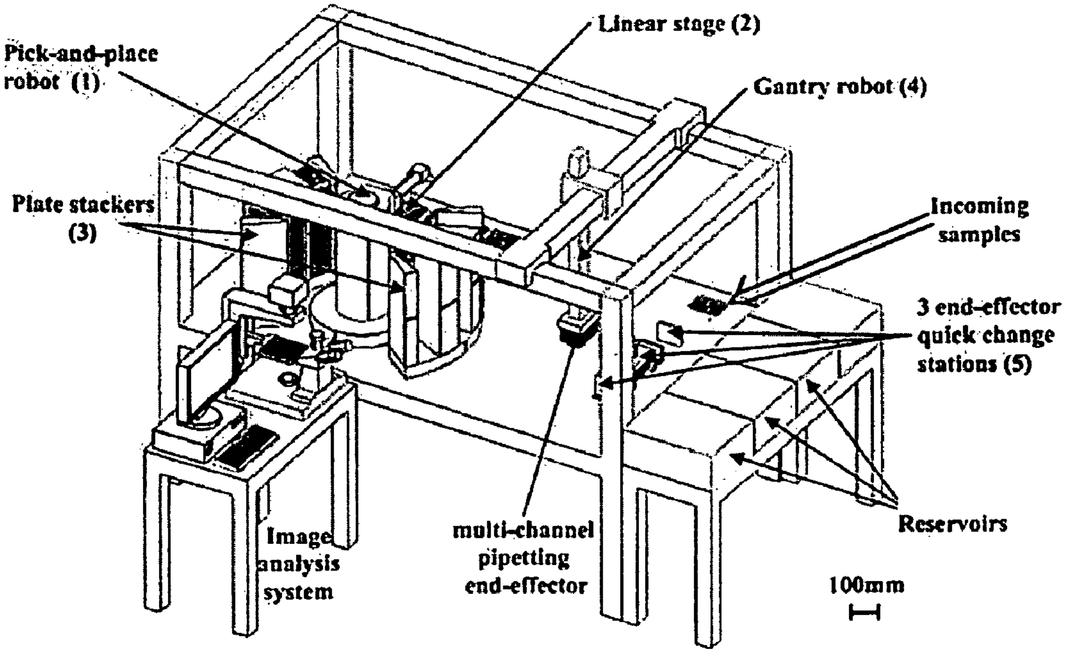
FIG. 27 illustrates a liquid handling module in accordance with an embodiment of the invention.

As illustrated in FIG. 27, tasks to be performed inside the plate and liquid handling module 14 fall broadly into two categories: 1) pick and place tasks associated with plate handling, and 2) various liquid handling tasks. As seen from a conceptual design shown in this schematic, a pick-and-place SCARA robot 271, a linear stage 272 equipped with a vacuum filtration device, and two plate stackers 273 with drainage function are strategically placed to handle all the tasks related to plate handling.

A gantry-type robot 274 is used for liquid handling tasks; this gives a larger working space to allow the robot to shuttle between the plate working area (on the linear stage) and the end-effector (hand) quick-change stations 275. In one embodiment, the robot has multiple degrees of freedom, and the configuration gives excellent positioning accuracy, which is important for multiple channel pipetting and washing.

In an embodiment, all the components are configured using a computer aided design (CAD) package and properly assembled inside the software. The sequence of robotic actions required is animated in the software to ensure no physical and timing crashes, and to facilitate any adjustments or repositioning. The high inertial effect associated with the rotating centrifuge rotor, and also experienced by the robot holding the rotating rotor, is also simulated to determine final details. The CAD systems used includes I-DEAS and ProE, both having strong assembly and animation capability as well as good dynamic simulation capability.

Figure 23:
FIG. 23 illustrates a multi-well plate in accordance with an embodiment of the invention.

As illustrated in FIG. 23, the wet multi-well plate is placed on a plastic substrate which is coated with a thin (~1 micron) layer of non fluorescent water-soluble glue. After drying for 20 minutes, the walls of the multiwell plate can be simply lifted away from the glued filter bases, leaving the filter bases flat, supported by the plastic substrate.

In one embodiment, the adhesive Elvanol (polyvinyl alcohol, which is the standard remoistenable postage-stamp adhesive), is used for this purpose, with no measurable fluorescence, providing a smooth micron thick layer on a plastic substrate. With the well walls removed, the cells on each filter can be imaged with optimal geometry, without imaging through the filter base.

Figure 24:
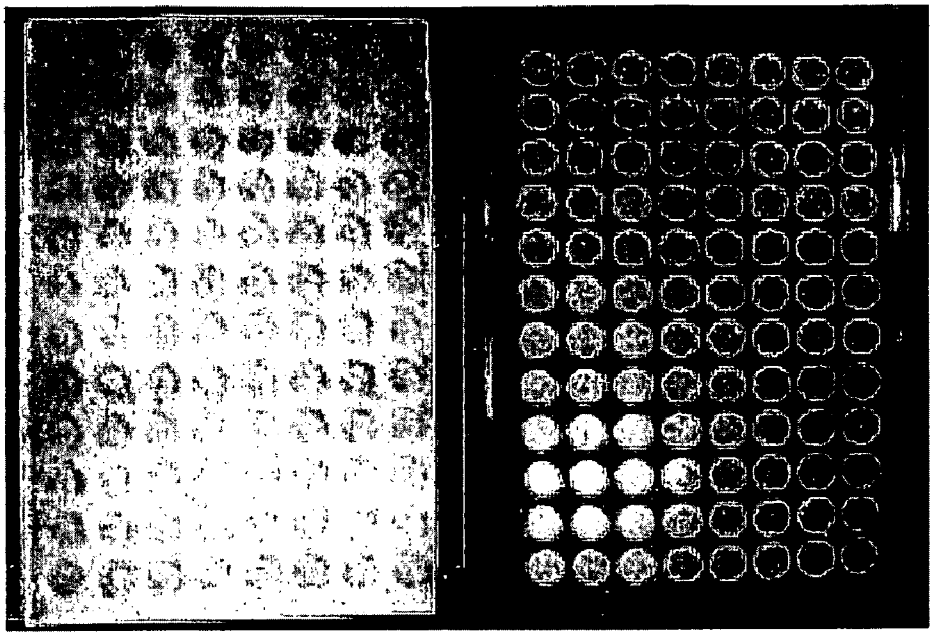
FIG. 24 illustrates filters attached to the multi-well plate in accordance with an embodiment of the invention.

In one embodiment, in the first procedure, sealing and transfer are done by filtering a 10% solution of polyvinyl alcohol (PVA —98% hydrolyzed) through the plate, while it is pressed against the substrate. After this glue has dried, the well walls are removed, leaving the filters attached to the substrate (see FIG. 24 below). To enable efficient filtering the embodiment shown in FIG. 24 uses Porex™ brand sheets as the material for the substrates. In addition, it was determined that precoating the porous sheets with glue prior to filtration improved filter attachment and reduced the time necessary for transfer and drying.

Figure 25:
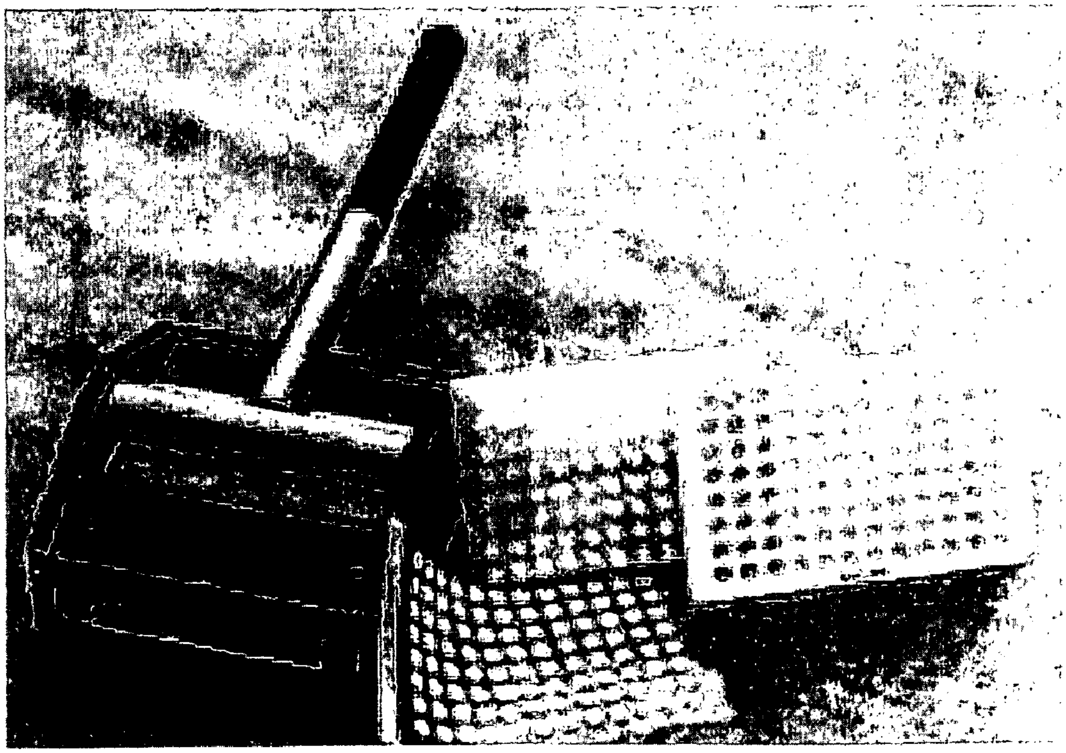
FIG. 25 illustrates a punching mechanism used to detach membranes from the multi-well plate in accordance with an embodiment of the invention.

In another embodiment, ELISA plate sealers (adhesive strips used for covering plates during incubation) are used as substrates. A punching mechanism (for example, MVS Pacific, shown in FIG. 25) is used to detach the membranes from the plates and to keep them intact. The plate sealer with the membranes is then laminated with 3-5 mil laminating film using a heat laminator. Prior to detaching, the membranes are sealed with PVA, as in the first case, to protect the cells.

Figure 26:
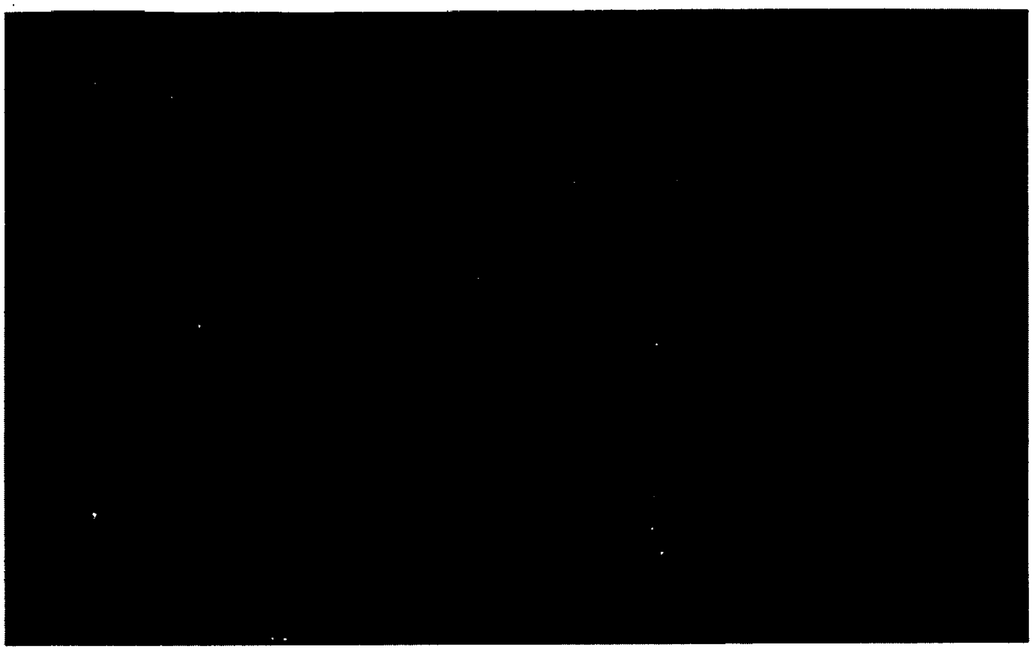
FIG. 26 illustrates a sealed and laminated membrane with fluorescent beads.

It was determined that beads and stains can withstand the high temperatures necessary for lamination and the laminating film does not interfere with the imaging (FIG. 26). In some embodiments, an adhesive substrate is used for transferring membranes. It does not require time for drying which is a factor for a high-throughput system. It does require sealing of the adhesive surface, but this drawback can be eliminated by using lamination. Previously, the quality of membrane transfer was better for Porex™ sheets, but in case of adhesive film it was greatly improved by introducing a punching mechanism.

In a second embodiment of the device, filter-bottomed multi-well plates are used but with an added option to increase throughput by using 384 well plates. In one embodiment, a new configuration for 384-well plates is used which has a) the same overall plate size as standard 96-well plates, b) 384 wells, each with a similar cross sectional area to standard 96-well plates, and c) 0.65 μm pore Millipore filters as the base of each well. For these custom plates, the wells are square in cross sectional area, which allows a higher well area/dish area ratio, and is more compatible with camera-based imaging than standard circular wells. The square wells have 4 mm sides, thus a 16 $mm^2$ cross sectional area (only slightly smaller than the 25 $mm^2$ cross sectional area in standard 96-well plates). As with the commercial 96-well filter-bottomed plates used in the first embodiment, the filters used in the second embodiment of the device are configured to be easily detachable from the walls of the wells.

Figure 28:
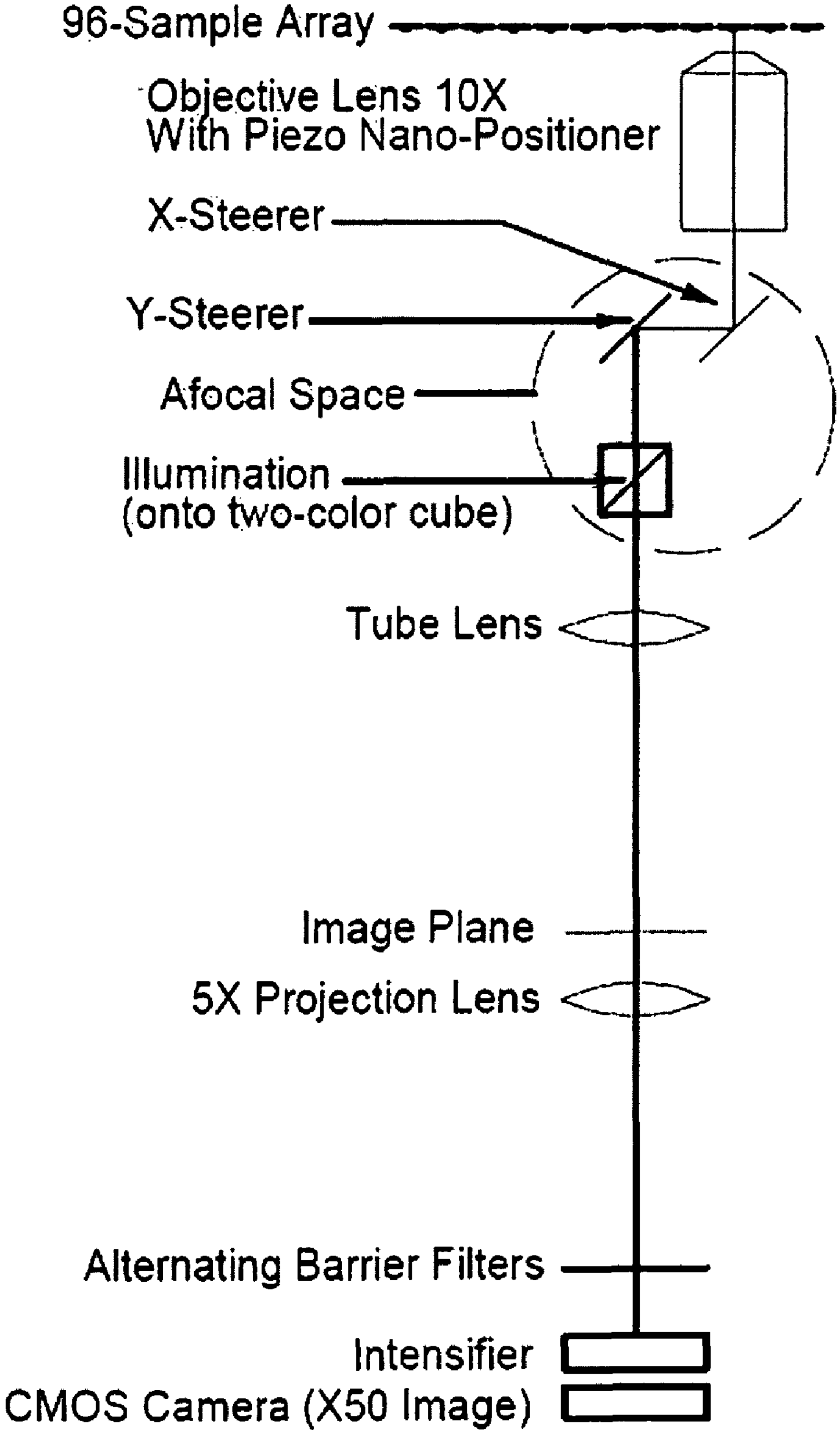
FIG. 28 illustrates a steered-image compound microscope in accordance with an embodiment of the invention.

Acquisition and analysis of microscopic images involves several discrete steps that must be substantially shortened to reach a preliminary goal of 6,000 samples/15 hr day, corresponding to about 10 seconds per well. As shown herein, this goal is achievable using the unique steered-image compound microscope as shown in FIG. 28.

Briefly, two fast galvanometric mirrors, X-steerer 281 and Y-steerer 282 were placed in the afocal space 283 of an infinity corrected microscope to steer different small parts of the view into the camera. This arrangement allows switching from one high-magnification field of view to another in less than a millisecond, compared to tens of milliseconds for the same action using a mechanical stage.

Commercial microscope stages such as the one used by the Metafer system are rather slow (70 mm/sec), this is partially due to the fact that the main bottleneck in those systems is the generalized image acquisition and quasi-offline analysis and partially because of the desire to limit the accelerations experienced by living cells.

Figure 29:
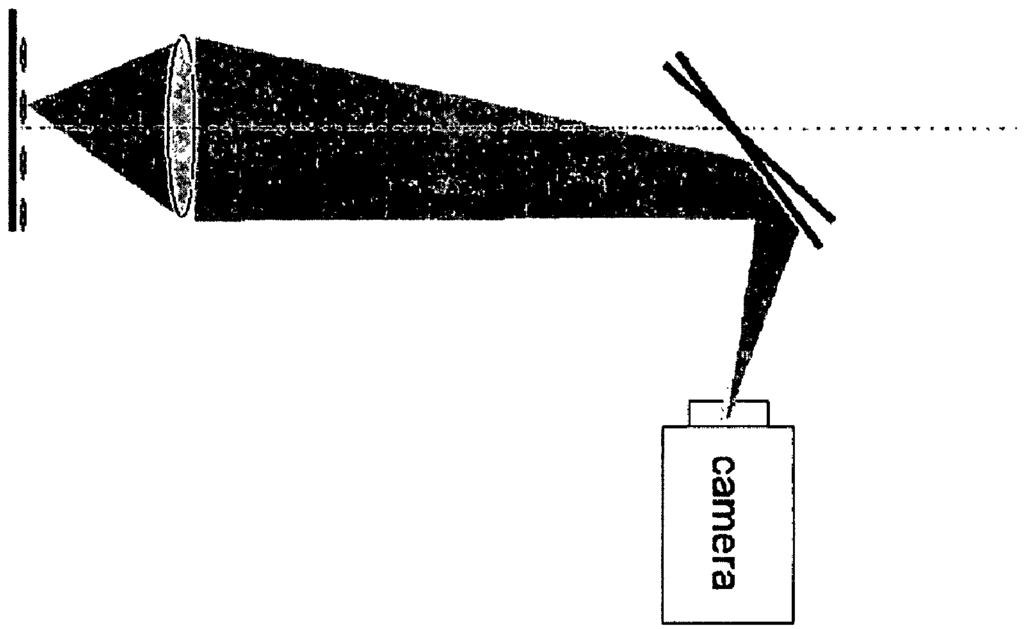
FIG. 29 illustrates the method and results of operating the steered-image compound microscope.
Figure 29:
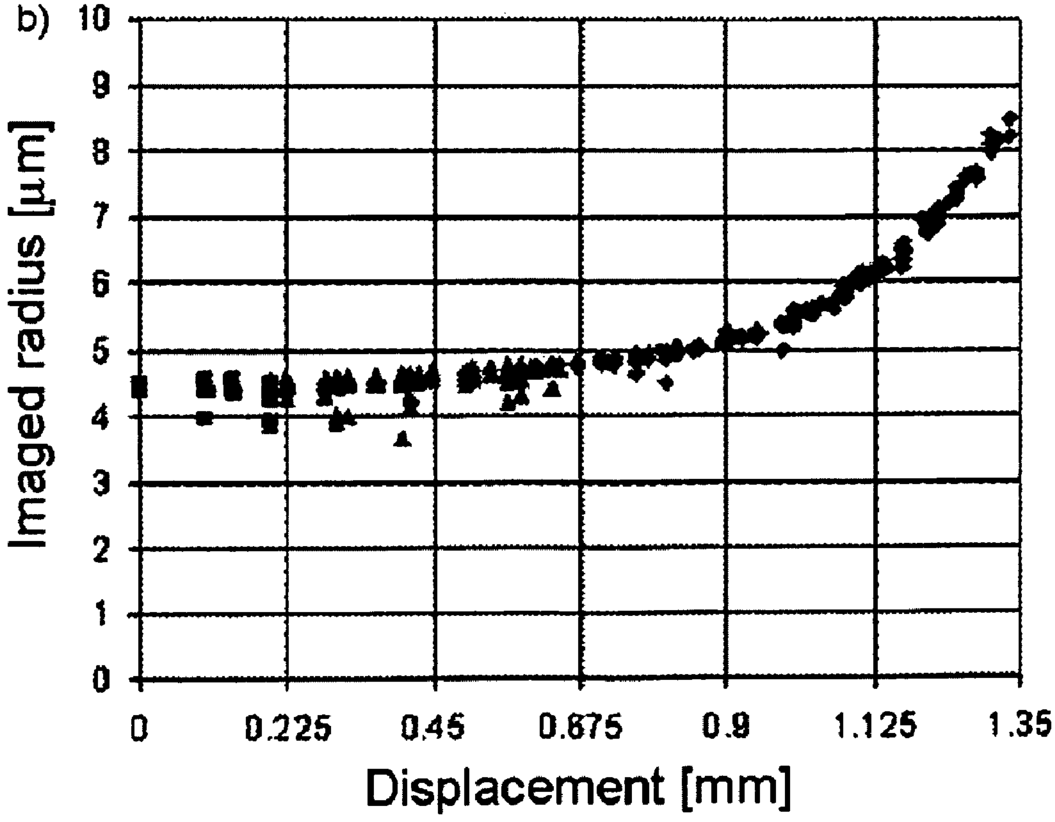

In an embodiment, both requirements are non-existent and a much faster stage is used. As in the microbeam, in one embodiment, the motion of the sample is separated into two components: a slower coarse motion and a rapid fine motion. The coarse motion is performed by a high speed stage (Parker motion) capable of few-g accelerations. This motion is used to move between adjacent samples (9 mm in 50 msec). The fine motion between fields of view within a single sample is performed, not by moving the sample but rather by steering light, using fast galvanometric mirrors as shown in FIG. 29. Typical transit times between adjacent fields of view of the microscope objective were measured at about 100 μsec. Extensive ray-tracing simulations have shown an effective increase of the microscope field of view by a factor of 100 (from 100 μm radius to 1 mm radius), before image degradation becomes noticeable. This was confirmed qualitatively.

Focusing

Figure 30:
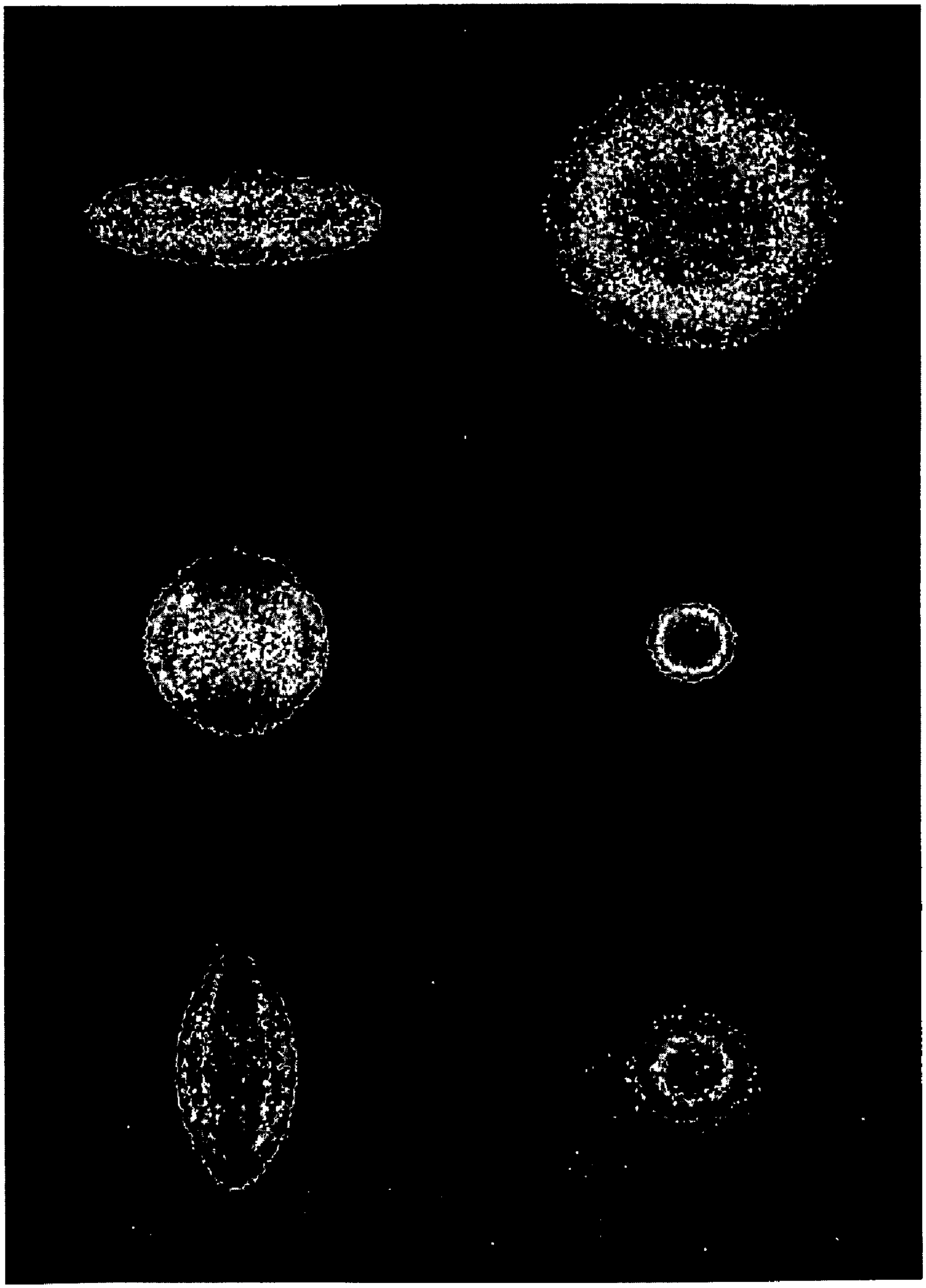
FIG. 30 illustrates simulated images demonstrating the effect of a cylindrical lens in an optical beam path as used in an embodiment of the invention.
Figure 31:
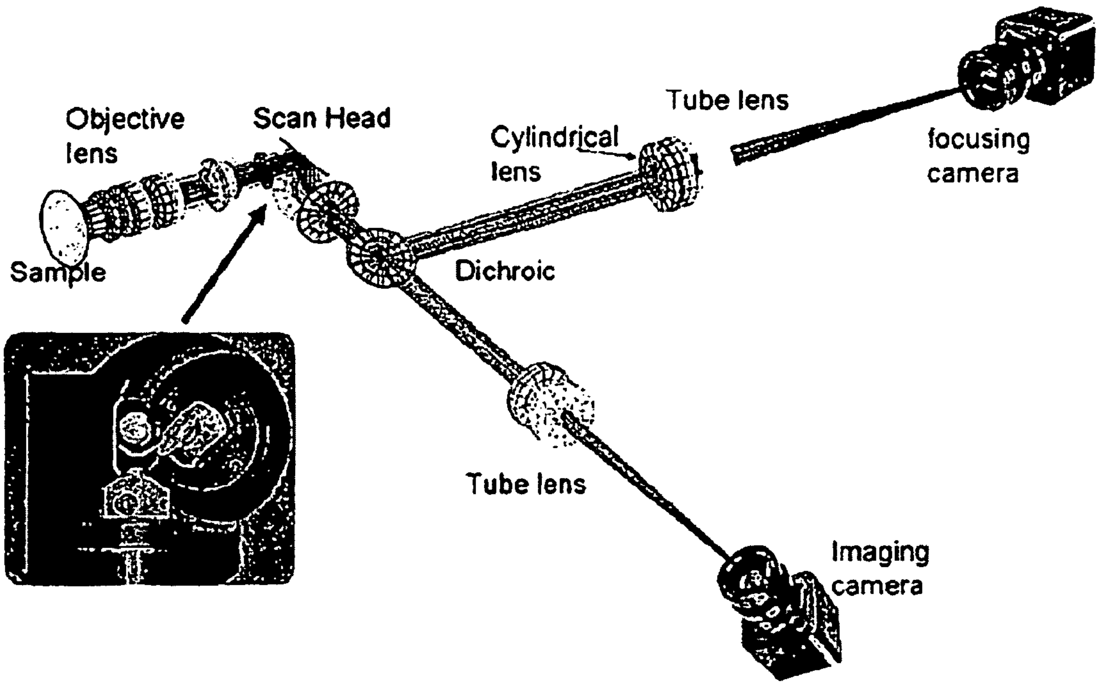
FIG. 31 illustrates use of a dichroic mirror and separate focusing and imaging cameras in accordance with an embodiment of the invention.

A major rate limiting step in automated imaging system is focusing. In order to get good image quality, typically microscope objective lenses have rather small depth of field and are sensitive to the roughness of the sample being imaged. The simple solution to this is to take several images at different object-lens distances, quantify "fuzziness" and search for the best setting. This process is very time consuming and therefore unacceptable. In embodiments of the invention disclosed herein, this concern by placing a weak cylindrical lens in the optics path. As shown in FIG. 30, by using an appropriately selected lens, a circular object will be imaged as circular when in focus and as elliptical when out of focus, the aspect ratio being proportional to the distance from focus. The object-lens distance can then be corrected in one step.

For imaging, one embodiment of the invention disclosed herein utilizes a complementary metal-oxide-semiconductor ("CMOS") camera, which has a much faster readout than the, lower noise, charge-coupled device ("CCD") cameras typically used. The resulting loss in image quality may be significant for "all purpose" imaging systems, but is unimportant in for detection of micronuclei. Analysis of the image is split between the camera and the frame grabber board to decrease the amount of data transferred to the controlling computer, the biggest bottleneck in existing imaging systems. By using a dichroic mirror and two cameras, attached to the same frame grabber board the system simultaneously "sees" the nuclear and cytoplasm and rapidly analyzes their overlap obtaining the number and size of nuclei in each cell.

To observe micronuclei with diameters down to 0.5 μm, the pixel size needs to be ~0.25 μm. Intensified digital cameras are available with 16 μm effective pixel sizes and are well suited for this application. Using ×50 optical magnification allows one to obtain 0.32 μm pixel resolution. A 1.31 Mega pixel camera with this resolution has a 15.36 mm×12.29 mm active area. At ×50 magnification, this yields a field of view with an area of 0.075 mm2. Comparing this to the size of a single well in the plates as described (diameter: 5.74 mm, area: 25.9 mm2), an area ratio is obtained that corresponds to 345 images to completely image one well surface. So the task is to move to and image those 345 locations in 10 seconds.

As a first step in achieving the desired processing rate, cell samples from a 96-well filtration plate are positioned on the imaging platform for viewing using the integrated robotics described above. To position the bottoms of each well under the microscope lens, a fast X-Y mechanical stage is standardly used. If a fast X-Y stage is used for 345 movements, taking about 40 msec per movement, 13.8 seconds per well has already been used, more than the allotted time, just for positioning. This problem is solved by replacing this standard configuration of a 50× objective and mechanical stage motion with a novel steered-image compound microscope. A 10× objective (Nikon CFI60) is used, with a piezo nano-positioner followed by a 5× projection lens to obtain ×50 magnification. Infinity optics allows the placement of X-Y steering mirrors (Scanlab) within the afocal space to guide different parts of the full image down the optic axis to the camera sensor. Switching between images can thus be accomplished in much less than one millisecond, using fast steering mirrors.

For this image acquisition process, the well surface is divided into 13 fields of view through the objective lens; the partitioning consists of a row of two images followed by three rows of three images and capped by a row of two final images. Each of these fields is then divided into 25 additional high-magnification views by the X-Y steering mirrors. The total time for motion using this scheme is less than one second—a major improvement over the 13.8 seconds per well that is needed for mechanical stage based motion.

The second process to be considered is the acquisition and data transfer of the image. Usually a CCD camera is used for microscopy. These devices are chosen for their very low leakage, allowing long exposure times, a factor that is unimportant for the present application. In fact, the physical structure of CCDs does not allow rapid readout. Transferring images faster than about 30 frames per second leads to degraded image quality. An emerging technology that uses CMOS imaging arrays (Loinaz M. Video cameras: CMOS technology provides on-chip processing. Sensor Review 1999; 19:19-26) solves this problem. The structure of CMOS devices allows for fast digitizing and transfer of images to memory. A camera well-suited is the ultra high speed Photon focus model MV-D1024E-160 series 8-bit CMOS camera, which can acquire images and transfer them to a computer at 150 frames per second. Image analysis is done off-line, as discussed below.

Due to inevitable non-uniformities in the imaging substrate, it is necessary to adjust the focus to compensate. There are a number of autofocusing routines used in current machines, which depend on focusing random objects which appear in the image. In order to make the autofocusing more robust, a new approach is used, involving adding 1-μm diameter fluorescent microspheres to the sample surface. With 10,000 beads per well, approximately 30 beads are available per magnified view, which is far fewer beads than there are 0.6 μm pores in the filter substrate, so the beads will not interfere with the ability to drain the well through the pores. The color of the beads is chosen so there is no overlap with the fluorochromes(s) used in the cellular imaging.

In a first embodiment of the device, illumination of the beads is done with a standard mercury lamp. Crimson beads (Molecular Probes Inc) have an excitation wavelength of 625 nm and an emission spectrum with a peak wavelength of 645 nm. A two-color cube allows both wavelengths of the bead emission and the cell stain emission to pass towards the CMOS-imaging sensor. Prior to the sensor, barrier filters are alternately introduced into the optic path to image either the cells (blue light) or to focus on the beads (crimson). During focusing, the CMOS image is binned in 2×2 segments and the images are analyzed to move the objective in to proper focus. 2×2 binned images can be acquired at 2400 images/sec. Twelve (12) images are expected to be acquired to obtain the focus, and the entire focusing process is calculated at about 50 ms, including the settling time of the piezo nano-positioner of the microscope objective; this is done 13 times per well.

In another embodiment of the device the light from the beads is split off from the light from the cell stain using a dichroic mirror. The light from the beads then passes to a separate camera via a cylindrical lens. Using the aspect ratio of the bead image allows obtaining focus after a single image.

Figure 32:
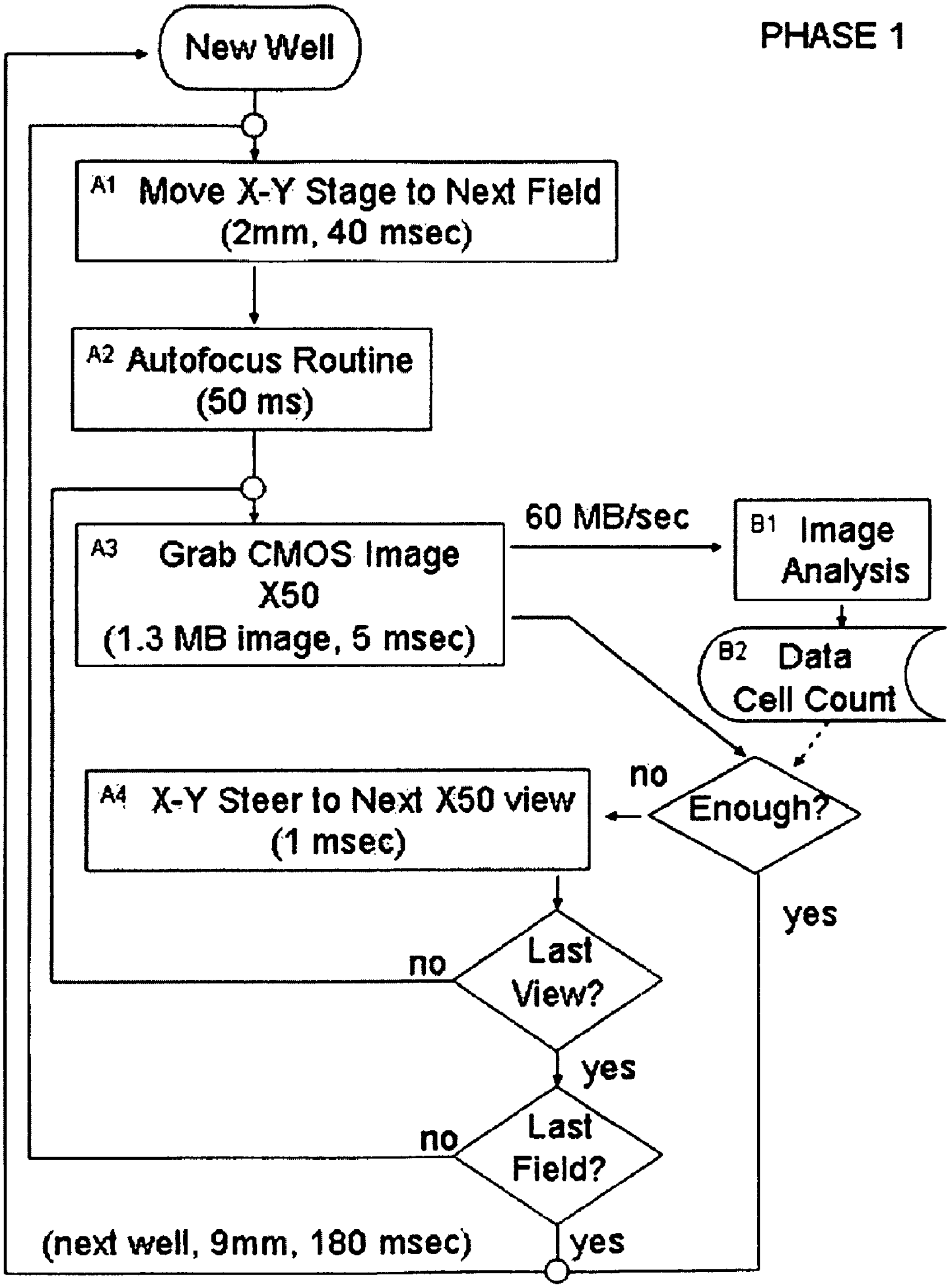
FIG. 32 depicts data flow for an embodiment of the invention.

Data flow factors relevant to the imaging speed are the motion times for the stage and the steering mirrors, as well as the camera exposure and read-out limitations. FIG. 32 depicts the data flow for an embodiment of the invention disclosed herein.

First, considering that the linear speed for the stage is 50 mm/sec, it takes 40 ms for the stage to move the samples to the next field (there is a 2 mm step size to the next field) and an additional 50 ms to focus. Next, it takes 5 ms to grab a CMOS image, using a mercury-arc illuminator, and 0.1 ms for the X-Y steering mirrors to point the next partition of the field to the CMOS sensor, totaling 5.1 ms for this portion of the routine. This sequence continues until each partition has been imaged. Afterwards, it takes 90 ms for the next field to be positioned over the objective lens by the mechanical stage and to be refocused. When 13 fields have been imaged, it takes 180 ms for the X-Y stage to move the next well into position above the objective.

Following a CMOS image grab, the image is transferred at 60 MB/sec, to an asynchronous image analysis computer. This step runs in parallel with the X-Y steerer moving the next ×50 view to the CMOS sensor. In the image analysis section, the images are scanned for cells with predetermined features and any such identified cells will be counted. If enough cells are counted, the X-Y steering loop exits and the mechanical stage moves the next cell well into an initial position for imaging.

The goal for this embodiment of the device is to process 6,000 wells per day and this goal is easily achieved with the proposed monochrome-imaging protocol above. It is possible to acquire color images with the addition of wavelength filters, and at the cost of throughput time. In the second embodiment of the device, color analysis is possible with no loss of throughput.

To summarize, in terms of high-throughput image acquisition, new features are incorporated into the first embodiment of the device. For example, compared to the current state of the art such the Amersham IN Cell 3000 machine. One is the novel steered-image compound microscope approach, and the other is the use of CMOS rather than CCD technology. Together, these two advances give more than an order of magnitude increase in speed compared with known devices. Another embodiment increases image acquisition speed by further developing the "steered image compound microscope" technology introduced in our first embodiment of the device.

Figure 33:
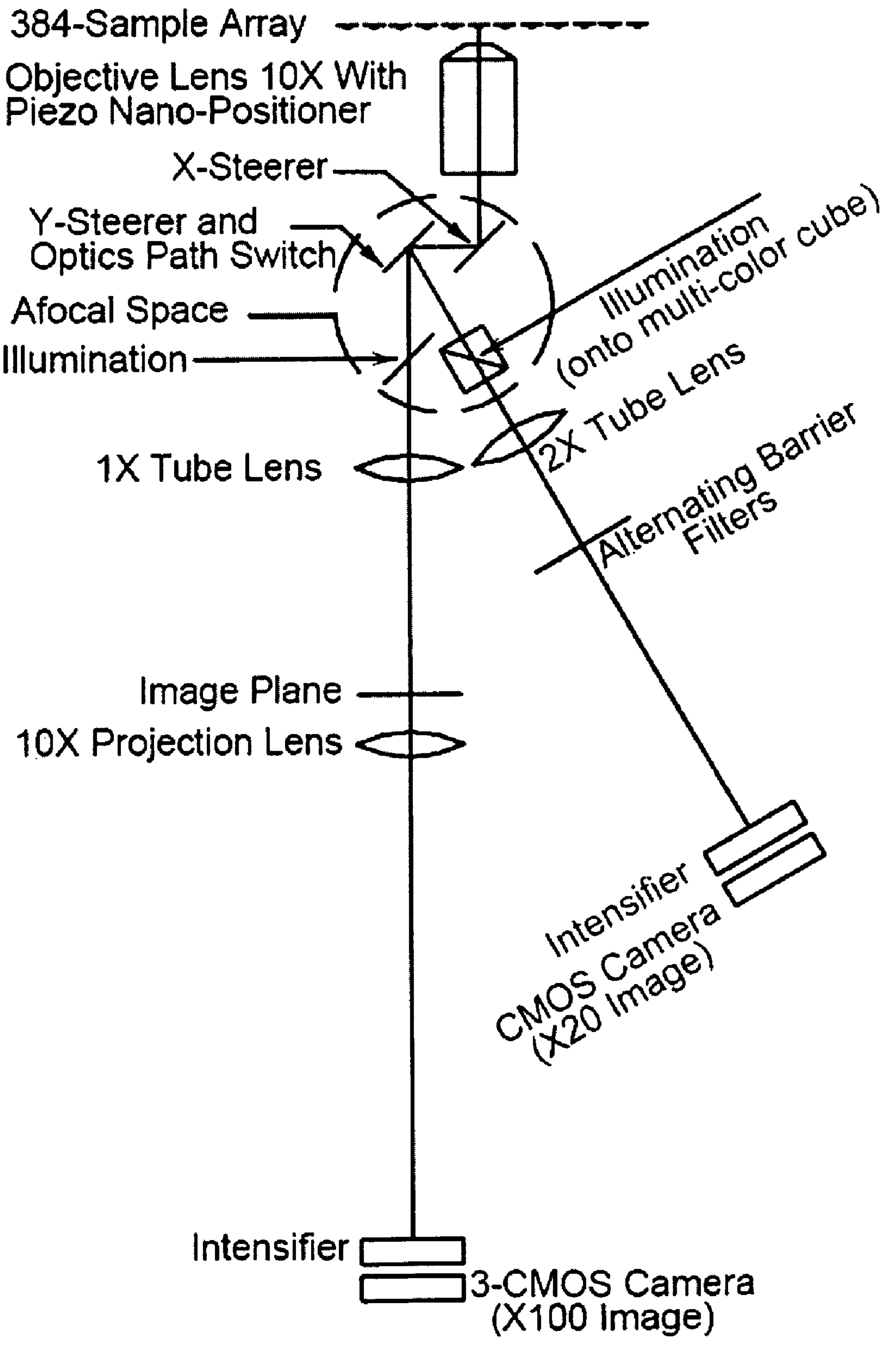
FIG. 33 illustrates a further embodiment of the steered-image compound microscope in accordance with an embodiment of the invention.

Referring to the FIG. 33, note the second optical channel with lower magnification. An image taken in this channel is used as a selector for regions to be observed at high magnification allowing cherry-picking of the most interesting regions.

A limitation of the speed of analysis is that, a priori, the position of the binucleate cells, and so time is spent imaging areas of no interest. The system described herein overcomes this problem by first scanning at low magnification to locate regions of interest to be examined at high magnification after a change of microscope objectives (Randers-Pehrson G, Geard C R, Johnson G, Elliston C D, Brenner D J. The Columbia University single-ion microbeam. Radiat Res 2001; 156:210-4). This approach addresses this limit using an analogous but much faster technique employing a dual optical path imaging system, as shown in the previous schematic. With the 384-well plates described above, there is a square aspect ratio, convenient for imaging. Twenty-four primary images are used to capture the well bottom; four of these images are steered to the ×20 CMOS imager at each stage position. There are 25×100 views within each ×20 view. The primary image is analyzed to find putative binucleate (BN) cells. Using cluster analysis, a threshold density of BN cells within a low-magnification view marks the regions for high-magnification imaging. Imaging only these regions and ignoring regions devoid of binucleate cells is more efficient because the number of images grabbed and processed is significantly reduced. A pair of fast galvanometric mirrors is used to direct the image of only BN cells into the second optical train which now has a 10× projection lens, resulting in a ×100 image at the small area, fast 3-CMOS color array for location of micronuclei. An Argon ion laser significantly enhances the imaging process in the second embodiment of the device by offering a more collimated, higher power light source with multiple excitation lines to illuminate multiple targets, e.g. γ-H2AX and nuclei. The secondary imaging is done at a rate of 500 frames/sec yielding a measurement time of 2 sec/1000 BN cells.

The autofocusing routine for the second embodiment of the device is similar to the one used in the first embodiment of the device except for the illumination. For the second embodiment of the device, a red LED emitting at 625 nm is used, an exact wavelength match for exciting crimson fluorescent beads. Since this bead illuminator is a separate light source from the Argon ion laser used for sample illumination, a fast switching mirror alternates paths, depending on which light source is being used in the lower magnification channel. This light switch is synchronized to the barrier filters discussed above.

Figure 34:
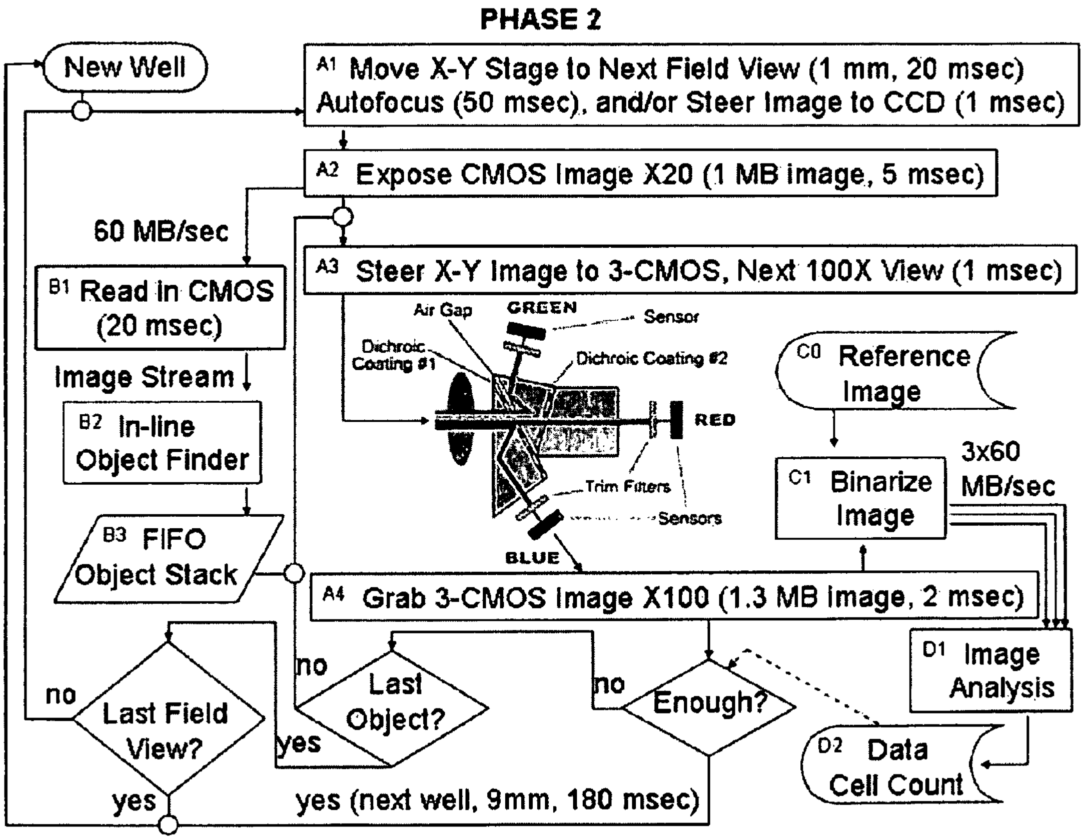
FIG. 34 illustrates system process flows for an embodiment of the invention.
Figure 35:
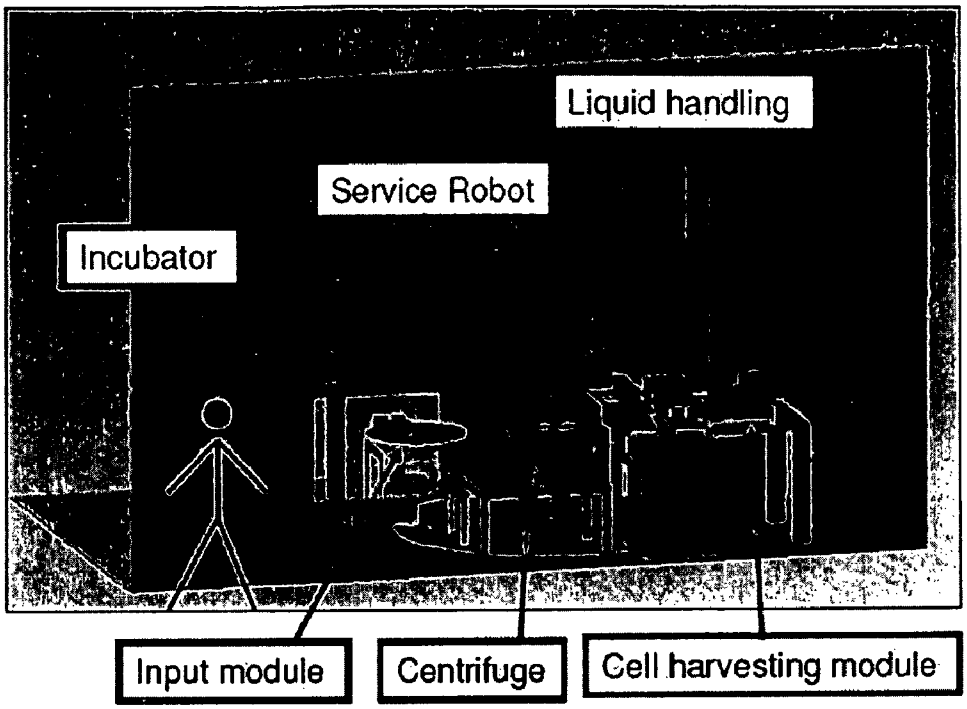
FIG. 35 illustrates an isometric view of an overall system layout in accordance with an embodiment of the invention.
Figure 35:
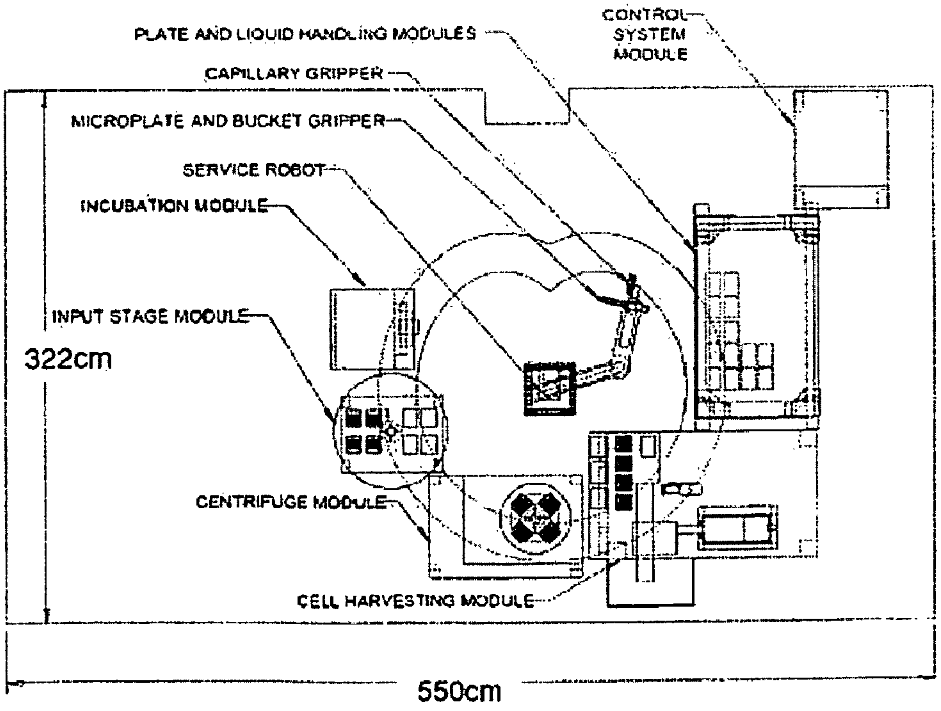

Parallel architecture enables a throughput of at least about 30,000 samples per day, using color imaging. The various parallel processes and the times associated with each are shown in FIG. 34. Some actions are necessarily done in series, namely, stage motion and focusing, acquisition of the low magnification image and acquisition of multiple high magnification images. By selection of hardware and by careful scheduling of stage motions, all other activities are performed in parallel with these. Image analysis occurs in parallel on fast vision processing boards.

In some embodiments, high-magnification, color images are acquired using a color-selecting prism and a fast three CMOS camera array. Each camera is equipped with an on-board binary converter which speeds up the transfer rate by 8×. Also, image information from each camera is read out over three channels, so that this step is not a rate-limiting factor. For each well, a throughput calculation is a summation of the imaging sequence. A throughput of at least about 30,000 wells per day and is readily achievable with this parallel color-imaging protocol.

Image processing needs include rapid identification of micronuclei associated with binucleate lymphocytes, with high sensitivity and specificity. Successful computer image analysis depends on the quality of the image presented for analysis. Demonstrated herein is successful production of very high contrast images of the fixed nuclei and micronuclei using a DNA binding stain such as DAPI or Hoechst 33342. These stains are observed with epifluorescence imaging with UV light. It is important to make sure that the substrates and reagents used do not add any background fluorescence.

The resulting images are highly compatible with binary segmentation and standard blob analysis. Several algorithms have been published in the literature in regard to morphometric features, such as size, aspect ratio, relative distance and concavity depth etc., that can be used for identification of the binucleated cells and micronuclei (Varga D, Johannes T, Jainta S, Schuster S, Schwarz-Boeger U, Kiechle M, et al. An automated scoring procedure for the micronucleus test by image analysis. Mutagenesis 2004; 19:391-7; Lozano A, Marquez J A, Buenfil A E, Gonsebatt M E. Pattern analysis of cell micronuclei images to evaluate their use as indicators of cell damage. Engineering in Medicine and Biology Society, 2003. Proceedings of the 25th Annual International Conference of the IEEE. Vol 1. Cancun, Mexico: IEEE; 2003. p. 731-4; Bocker W, Streffer C, Muller W U, Yu C. Automated scoring of micronuclei in binucleated human lymphocytes. Int J Radiat Biol 1996; 70:529-37; Verhaegen F, Vral A, Seuntjens J, Schipper N R, de Ridder L, Thierens H. Scoring of radiation induced micronuclei in cytokinesis-blocked human lymphocytes by automated image analysis. Cytometry 1994; 17:119-27).

An addition to the traditional image processing approach for defining the identification criteria, which has been used extensively (Long X, Cleveland W L, Yao Y L. Effective automatic recognition of cultured cells in bright field images using Fisher's linear discriminant preprocessing. In Proceedings of IMECE04: 2004 ASME International Mechanical Engineering Congress. Anaheim, Calif.; 2004; Long X, Cleveland W L, Yao Y L. Automatic detection of unstained viable cells in bright field images using a support vector machine with an improved training procedure. Computers in Biology and Medicine 2004:accepted; Long X, Cleveland W L, Yao Y L. A new preprocessing approach for cell recognition. IEEE Transactions on Information Technology in Biomedicine 2004:accepted), is the use of algorithms based on machine learning techniques (Mitchell T M. Machine Learning. New York: McGraw-Hill; 1997). Machine learning techniques are able to capture complex, even nonlinear, relationships in high dimensional feature spaces that are not easily recognized or defined by the human operator. This technique is used to "teach" the image processing system to recognize nucleoplasmic bridges, which are an important adjunct for increasing the specificity of the radiation-induced micronucleus assay (Fenech M, Bonassi S, Turner J, Lando C, Ceppi M, Chang W P, et al. Intra- and inter-laboratory variation in the scoring of micronuclei and nucleoplasmic bridges in binucleated human lymphocytes. Results of an international slide-scoring exercise by the HUMN project. Mutat Res 2003; 534:45-64; Fenech M, Chang W P, Kirsch-Volders M, Holland N, Bonassi S, Zeiger E. HUMN project: detailed description of the scoring criteria for the cytokinesis-block micronucleus assay using isolated human lymphocyte cultures. Mutat Res 2003; 534:65-75, 92).

The classifications defined either explicitly or through a "learning" technique are programmed into the vision processor for rapid operation. For example, the Matrox Odyssey Xpro scalable vision processor board can be used, which is designed for parallel and pipelined processing. Operating at 120 billion operations/sec, this board can easily analyze the 300 images acquired for each well within the ten seconds allotted to achieve the target throughput for a first embodiment of the device. The board also has the high speed image transfer capabilities required. As still faster vision processing boards appear, appropriately upgrading is made, but image processing is not a bottleneck for a first embodiment of the device.

With respect to a second embodiment of the device, there will be fewer images to analyze in the second embodiment, because of the cluster techniques as discussed supra in the image acquisition section, which is an estimated gain by a factor of 2. As discussed above, the second embodiment of the device also triples the speed of the image transfer, by using a full camera link interface. It is also pertinent to note that this device features improved image quality, due to the use of a 100× lens, rather than the 50× lens employed in the first embodiment of the device.

In the second embodiment of the device, image processing is similar to that used with the first embodiment of the device, except that two (or optionally 3) camera images need to be processed, corresponding to different colors. As discussed above, the image processing for the different colors is done in parallel, rather than in series as in the first embodiment of the device. Usually one image is used to produce a mask for the image in the second camera, simplifying the needed calculation. For example, in the micronucleus assay, an image of the cytoplasm stained in one color is used to delimit regions that may contain two nuclei and potentially some micronuclei. Similarly, in the γ-H2AX assay, the Hoechst stained nuclei produces a colored mask to select regions in which to count foci.

With respect to system integration, two levels of control are implemented: 1) control at the level of components and subsystems, and 2) sequential (or logical) event control. Component control is closed loop for most components, with the exception of the liquid handling system, which is open loop. Sequential control is implemented by a Programmable Logical Controller.

Corresponding to the control module, user software is also implemented at two levels: 1) modular component and subsystem software, and 2) global monitoring and coordinating. The key technical strategy is to make the software highly modularized. Modularization of software not only has the advantage of increasing code reusability, minimizing software development, but it also dramatically reduces maintenance costs after commercialization.

System monitoring and failure avoidance strategies are contemplated. The system development described so far has aimed at high reliability. However, because it is also aimed at high-throughput full automation, system monitoring for early fault detection and catastrophic failure avoidance in key components is preferred. The standard approach is by placing sensors at strategic locations in the system to monitor system performance. However, such an approach increases system complexity, maintenance needs, and cost.

Instead, a novel proposed approach is to make the maximal use of the sensing capability already existing in the system components. For instance, the motor current of a rotating centrifuge unit is a good indicator of any jam and breakage of the rotor and/or buckets. In any of these events, the current increases and thus give a sensitive indication for the need of an emergency stop. The motor current of all the actuators including those for centrifuges, punctuator unit, stage at the plate working area, microscope stages, and robotic arms is continuously monitored. For the liquid handling system as well as the pneumatically-actuated end effectors, the liquid pressure and pneumatic pressure are continuously monitored using transducers at strategic locations.

High speed identification and tracking are also preferred for a reliable high throughput system. RFID (radiofrequency ID) labeling and scanning (Want R. RFID. A key to automating everything. Sci Am 2004; 290:56-65), which has a number of practical advantages over barcode systems (Jossi F. Electronic follow-up: bar coding and RFID both lead to significant goals—efficiency and safety. Healthc Inform 2004; 21:31-3), are used in one embodiment. A commercial RFID scanning system is used to tag and track both the individual blood/tissue samples, and each multi-well plate. A commercial RFID database is used to track each sample during the whole process.

In summary, the high throughput product described herein is based on automated assays in situ in multi-well plates. All the minimally-invasive assays that are used (micronuclei in lymphocytes, γ-H2AX foci, micronuclei in blood reticuloctyes, micronuclei in exfoliated bladder or buccal cells) have been chosen because they are a) well established and b) amenable to automation. System optimization can be achieved using ex-vivo irradiated samples from healthy human volunteers. Calibration and testing can be achieved using samples from adult and pediatric patients who were subject to total body irradiation.

In one embodiment, the system described herein comprises only four main modules adapted to accomplish i) sample handling, ii) information logging and iii) imaging: a robotic centrifuge module, a service robot 352, a cell harvesting module 353 and a liquid/plate handling robot 354, and a dedicated image acquisition/processing system. See FIG. 35.

A Selective Compliant Articulated Robot Arm ("SCARA") is preferred to automate the blood sample transfer operations among the modules. To this end the SCARA workspace is augmented by designing an additional link capable to reach safely into the workspace of the liquid/plate handling robot 354 as shown in FIG. 35*b*.

Robotic Centrifugation Module

An overview of the automated processing steps begins with loading blood samples, contained in hematocrit capillaries, which may be made of polyvinyl chloride (PVC), into a centrifuge which will isolate the lymphocytes. A challenge here is to meet the desired throughput and system reliability when handling capillaries.

Figure 36:
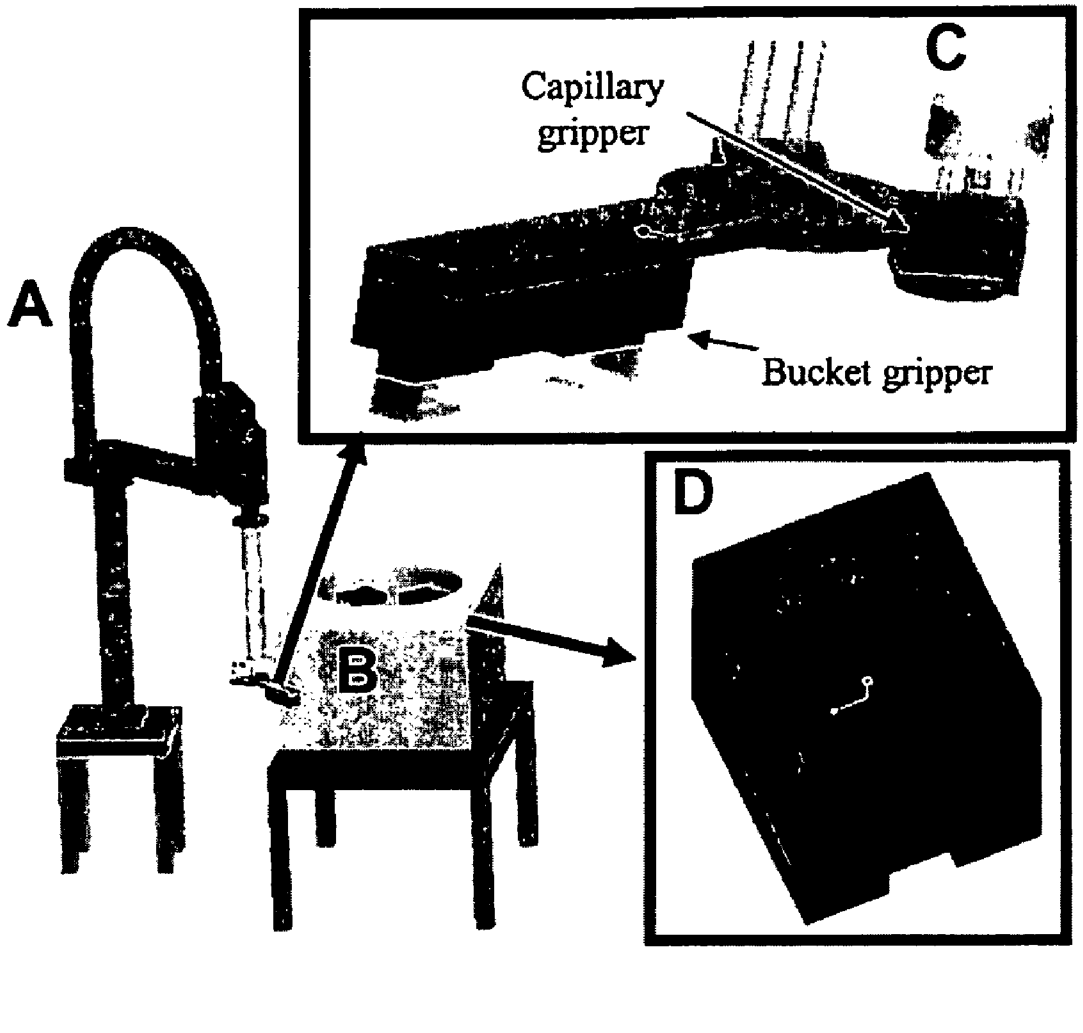
FIG. 36 depicts a multi-purpose robotic gripper used in an embodiment of the invention.

To cope with this problem, as illustrated in FIG. 36, a novel multi-purpose robotic gripper is designed for i) centrifuge-buckets and micro-plates handling and ii) multiple handling of capillaries.

Cell Harvesting Module

After centrifugation the samples are transferred to a band recognition module, where cell harvesting is completed by cutting the hematocrit tube to select the lymphocytes. Plasma and lymphocytes are flushed into the appropriate well. A challenge faced here is the contactless automatic cutting of PVC hematocrit capillaries. To avoid cross-contamination associated with the use of non-disposable mechanical cutting tools, a laser-based cutting system, illustrated in FIG. 37*a* is preferred for cutting capillaries (FIG. 37*b*).

Figure 37:
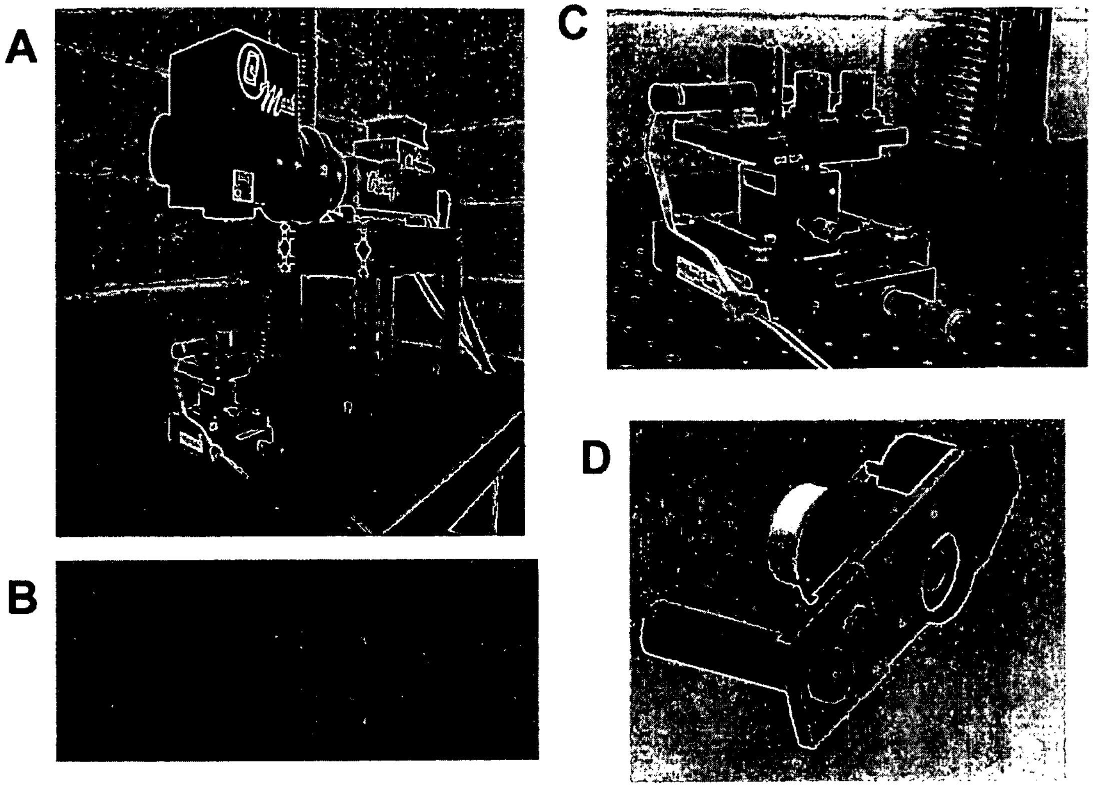
FIG. 37 apparatus for contactless automatic cutting of capillaries in accordance with an embodiment of the invention.

In an embodiment, an automatic rotary stage is designed and implemented to allow for even distribution of the laser-delivered power along the circumference of the cut cross-section, as illustrated in FIG. 37*c*. A collet/solenoid-based gripper is employed for automatic capillary back feed, as illustrated in FIG. 37*d*.

Peripheral Blood and Capillary Blood: In some embodiments, the assays used in the device are blood based. Thus, in one embodiment, peripheral blood drawn by venipuncture is used. In a second embodiment, capillary blood is used in order to increase overall throughput. Currently, the most common source of capillary blood is a disposable lancing device (Fruhstorfer H. Capillary blood sampling: the pain of single-use lancing devices. Eur J Pain 2000; 4:301-5; Garvey K, Batki A D, Thomason H L, Holder R, Thorpe G H. Blood lancing systems for skin puncture. Prof Nurse 1999; 14:643-8, 50-1); however laser skin perforators, such as the FDA-approved Lasette P200 (Cell Robotics Inc), have considerable high-throughput application here, and have high patient acceptability (Burge M R, Costello D J, Peacock S J, Friedman N M. Use of a laser skin perforator for determination of capillary blood glucose yields reliable results and high patient acceptability. Diabetes Care 1998; 21:871-3).

In terms of the volume of capillary blood that will be available, several studies have been made on the volume of blood that can be obtained from disposable automatic capillary lancing devices, while causing minimal pain (Rosenthal P, Weber W, Forster A, Orth O, Kohler B, Seiler F. Calibration and validation of a quality assurance system for 90Sr/90Y radiation source trains. Phys Med Biol 2003; 48:573-85; Florkowski T. Shielding for Radioisotope Bremsstrahlung Sources Sr90 Plus Y90. Int J Appl Radiat Isot 1964; 15:579-86). A recent study picked out the ITC Tenderlett and the Roche AccuChek Safe-T-Pro lancets as being safe, reliable, and causing the least pain (Fruhstorfer H. Capillary blood sampling: the pain of single-use lancing devices. Eur J Pain 2000; 4:301-5); these two devices respectively yielded mean blood volumes of 300 and 200 μl respectively, though with about 10% of the samples yielding less than 50 μl (Fruhstorfer H. Capillary blood sampling: the pain of single-use lancing devices. Eur J Pain 2000; 4:301-5). According to a published study (Burge M R, Costello D J, Peacock S J, Friedman N M. Use of a laser skin perforator for determination of capillary blood glucose yields reliable results and high patient acceptability. Diabetes Care 1998; 21:871-3), the Cell Robotics Lasette P200 laser skin perforator can generate blood volumes of more than 100 μl in 98% of subjects.

Based on these data, an embodiment is configured to require no more then 50 μl of blood per sample, with the expectation that those individuals who produce less than this could be given a repeat fingersticks or laser perforation. For example, two samples per individual are drawn for the lymphocyte-based assays, one being passed through the irradiator in the system to provide a positive control regarding individual radiosensitivity. However, for each assay, lower volumes can be adequate and where so, the lower volumes can and will be used.

In-situ analysis of micronuclei from lymphocytes in multi-well plates: The micronucleus assay has been standardized over many years, as a slide-based non-automated procedure (Fenech M, Bonassi S, Turner J, Lando C, Ceppi M, Chang W P, et al. Intra- and inter-laboratory variation in the scoring of micronuclei and nucleoplasmic bridges in binucleated human lymphocytes. Results of an international slide-scoring exercise by the HUMN project. Mutat Res 2003; 534:45-64; Fenech M, Chang W P, Kirsch-Volders M, Holland N, Bonassi S, Zeiger E. HUMN project: detailed description of the scoring criteria for the cytokinesis-block micronucleus assay using isolated human lymphocyte cultures. Mutat Res 2003; 534:65-75; Fenech M, Holland N, Chang W P, Zeiger E, Bonassi S. The HUman MicroNucleus Project—An international collaborative study on the use of the micronucleus technique for measuring DNA damage in humans. Mutat Res 1999; 428:271-83). To optimize the conditions for a fully-automated multi-well based system, a first embodiment of the device employs peripheral blood in 96-well plates. A second embodiment of the device uses capillary blood from fingersticks, in 384 well plates.

Sources of biological material: In one embodiment, peripheral blood is used, as drawn from multiple healthy volunteers and irradiated ex vivo. Additionally or alternatively, samples are taken from total body irradiation patients. For demonstration of the device, blood samples are taken from such patients from the University of Pittsburgh (adults) and Memorial Sloan Kettering Cancer Center (children).

Blood Separation: As discussed above, in the first embodiment of the device, peripheral blood collection and separation is based on BD Vacutainer CPT tubes. These tubes contain an anticoagulant with a Ficoll Hypaque density fluid and a polyester gel barrier. Centrifugation of these tubes for 25-30 min results in a single-step very clear separation of mononuclear white blood cells from plasma and from erythrocytes and neutrophils. Cells are maintained sterile and lymphocytes are withdrawn from their band of confinement, seen by eye as a highly turbid band, by hypodermic syringe. Multiple aliquots are taken.

Cell Culture: Comparisons are undertaken between standard culture procedures and culture in 96-well plates, prefilled with 250 μl of standard culture medium. The standard cultures are done using ~1 million cells, compared to about ~25,000 cells in the 96-well Millipore filtration plates. Under standard micronucleus assay conditions (Fenech M, Bonassi S, Turner J, Lando C, Ceppi M, Chang W P, et al. Intra- and inter-laboratory variation in the scoring of micronuclei and nucleoplasmic bridges in binucleated human lymphocytes. Results of an international slide-scoring exercise by the HUMN project. Mutat Res 2003; 534:45-64), cytochalasin B are added to cultures at 44 hr post cell cycle initiation. In the interest of shortening the assay, earlier times of addition can be tested, as well as earlier fixation times. Thus, along with the standard 72 hr time of culture stoppage, comparisons down to 56 hr can be made. Wash and dilution steps are minimized.

Cell Processing: Cells in the culture flasks are processed by standard procedures (Fenech M, Holland N, Chang W P, Zeiger E, Bonassi S. The HUman MicroNucleus Project—An international collaborative study on the use of the micronucleus technique for measuring DNA damage in humans. Mutat Res 1999; 428:271-83) to produce microscope slide preparations. However, the number of steps is minimized where possible and preferably all steps are amenable to robotic automation. As discussed elsewhere, 96-well Millipore plates (0.65 μm pores) are used, allowing medium to be drawn off by vacuum filtration, but without loss of lymphocytes. This is followed by a wash step with Hanks balanced salt solution and removal by vacuum filtration, and fixation step using absolute ethanol. The initial filtration steps result in cells settling firmly on the membrane and the fixation step enhances their adherence to the membrane.

Cell staining: Whereas the long established micronucleus assay uses light microscopy and Giemsa stain to discern nuclei and micronuclei, this stain results in unacceptable backgrounds for automated detection. Instead the highly specific DNA binding fluorochrome DAPI (4,6-diamino-2-phenylindole) or Hoechst 33342 is used as the indicator of binucleate cells plus/minus micronuclei. These fluorochromes are routinely used in cytogenetic studies and, in fixed cells, are clearly superior to the commonly-used propidium iodide.

Preparation of Sample For imaging: as Discussed in the description of the plate handling/liquid handling module, there are some issues involved with automated cell handling of lymphocytes, in that they do not attach well to surfaces, and thus it is important to ensure that a) significant numbers of lymphocytes are not lost during any medium removal/washing steps, and b) that the lymphocytes are located in a (near) monolayer during the image-acquisition stage, to ensure optimal imaging. Thus, in some embodiments, commercially-available Millipore 96-well filter plates in which the base of each well is a 0.65 μm pore filter are used. These pores are small enough so that lymphocytes cannot fall through the pores, nor will fluid pass through the filter, except when a small differential pressure (vacuum) is applied, in which case the medium is aspirated through the filters, and the cells will sit in an approximate monolayer directly on the bottom of the well. This solves both the problem of medium removal without losing cells, and of ensuring optimal conditions for the imaging stage. These 96-well sterile plates are available commercially from Millipore, and preliminary studies have indicated that this approach works well.

Imaging: in some embodiments, analysis tools include:

1. A multi-purpose semi-automated slide-based scanning system (Metafer (Schunck C, Johannes T, Varga D, Lorch T, Plesch A. New developments in automated cytogenetic imaging: unattended scoring of dicentric chromosomes, micronuclei, single cell gel electrophoresis, and fluorescence signals. Cytogenet Genome Res 2004; 104:383-9) developed by MetaSystems), which has been used for cytogenetically-based radiation dose estimates in highly exposed Russian nuclear workers (Hande M P, Azizova T V, Geard C R, Burak L E, Mitchell C R, Khokhryakov V F, et al. Past exposure to densely ionizing radiation leaves a unique permanent signature in the genome. Am J Hum Genet. 2003; 72:1162-70; Mitchell C R, Azizova T V, Hande M P, Burak L E, Tsakok J M, Khokhryakov V F, et al. Stable intrachromosomal biomarkers of past exposure to densely ionizing radiation in several chromosomes of exposed individuals. Radiat Res 2004; 162:257-63). This system has also been used for detection of radiation-induced binucleated post-division lymphocytes with and without micronuclei (Schunck C, Johannes T, Varga D, Lorch T, Plesch A. New developments in automated cytogenetic imaging: unattended scoring of dicentric chromosomes, micronuclei, single cell gel electrophoresis, and fluorescence signals. Cytogenet Genome Res 2004; 104:383-9). This system was utilized in the early first part of the instant studies to compare with results obtained in multi-well systems.

2. An Amersham In Cell 3000 Analyzer system, which is the current state of the art for automated high-throughput image analysis of multi-well plates.

3. Breadboard versions of the embodiments of the device.

Deployment of one embodiment includes three stages: breadboard, low-throughput prototype (6,000 samples per day) and high-throughput prototype (30,000 samples/day). In order to develop the breadboard a room was selected in such a way to impose dimensional constraints that would increase system portability. The room was equipped with an RS80 SCARA robot from Staubli, an O-Sprey UV laser system from Quantronix, a Sciclone ALH 3000 liquid handling robot from Caliper Life Sciences, a 5810RA Robotic Centrifuge from Eppendorf and an industrial PC from iBASE technology running RTAI Linux for the low-level control.

Figure 38:
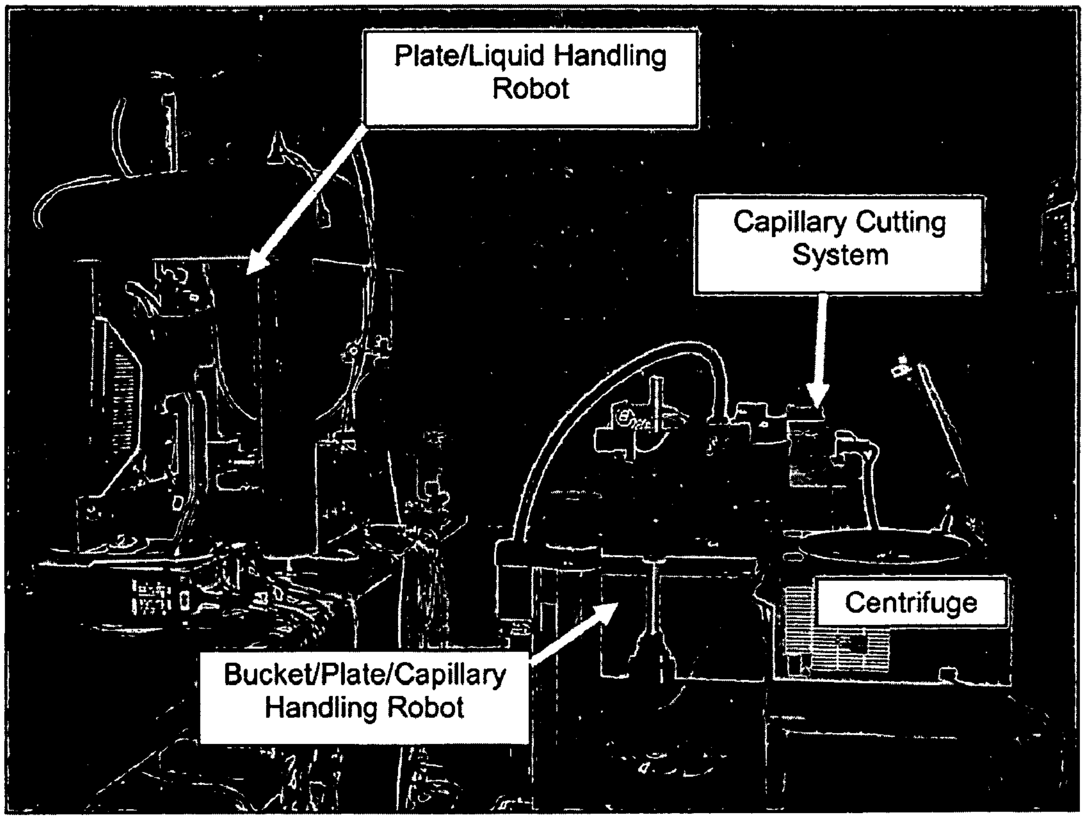
FIG. 38 illustrates an embodiment of a system implementation of the invention.
Figure 39:
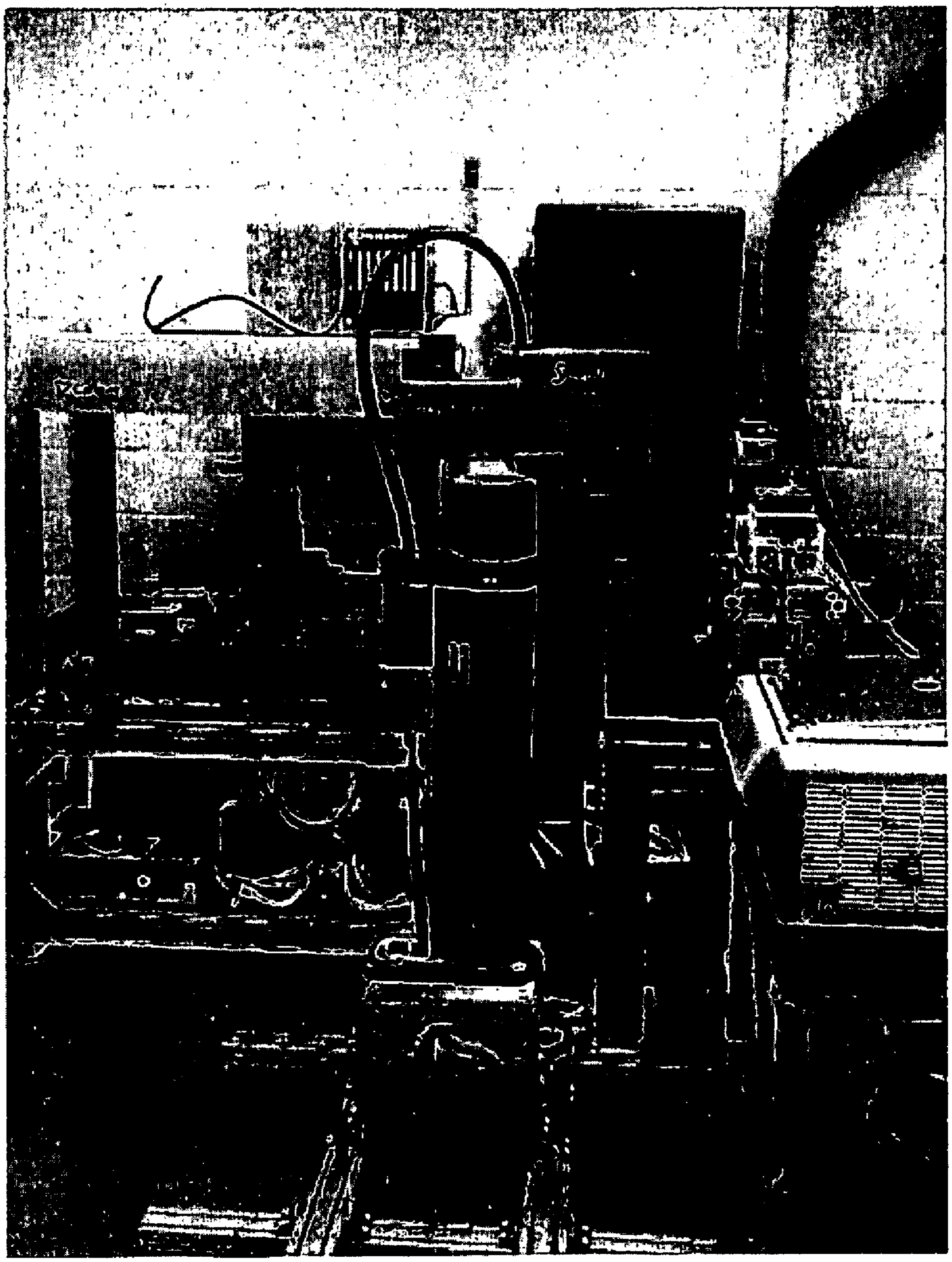
FIG. 39 shows a prototype.

An implementation of the breadboard without the image acquisition/processing module is illustrated in FIG. 38. A ptototype is illustrated in FIG. 39.

Figure 18:
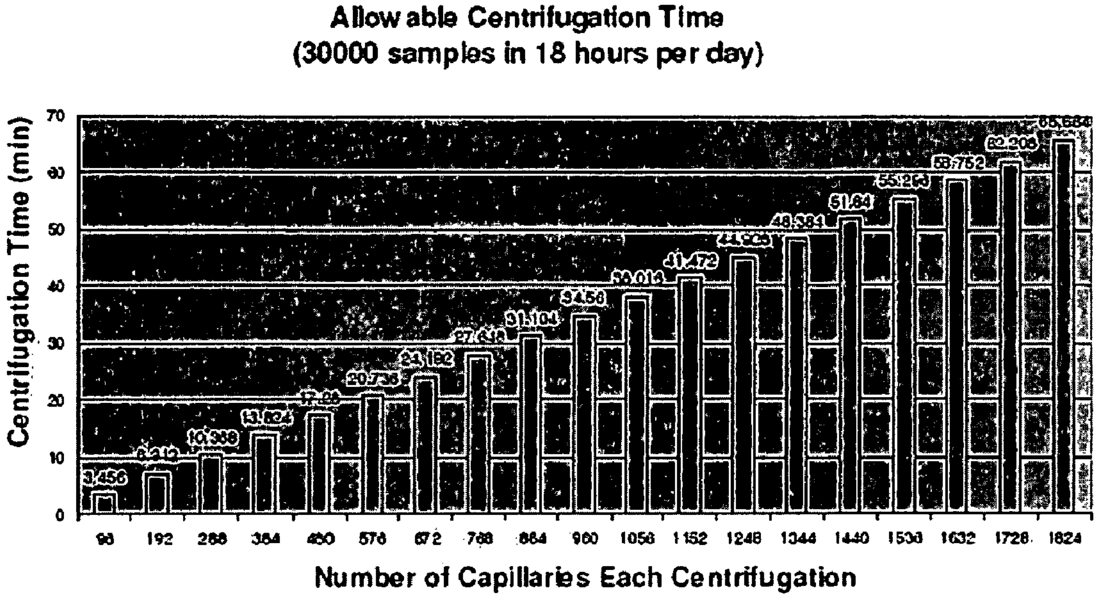
FIG. 18 illustrates a relationship between centrifuge time required as a function of number of capillaries in each centrifuge.

Current automated imaging systems have limited throughput, mostly due to their non-specificity, for example the Metafer system (Metasystems, Germany) can perform rare cell detection, comet assays, metaphase spreads, location of dicentrics, micronucleus scoring and more on 100-200 slides per day. This is about 1% of the desired throughput for a biodosimetry workstation. A need exists for a dedicated high-throughput imaging system for performing the micronucleus assay exclusively, seeking creative solutions for rapid sample manipulation, automated focusing and image acquisition and analysis, using the experience gained from developing the automated microbeam workstation. The throughput of an imaging system according to the present invention is estimated at 5-6 minutes/96-well plate or 20,000-30,000 individual samples/day (FIG. 18).

Multi-well cultures vs. standard cultures. Comparison can be made of micronucleus frequencies in both irradiated and unirradiated lymphocytes, between well-cultured and standard-cultured cells, along with intra- and inter-plate comparisons. Ex-vivo irradiated blood is used from a total of 50 healthy donors. Zero, low (0.5 Gy), medium (2 Gy) and high doses (5 and 10 Gy) are used, with every effort made to undertake the ex-vivo irradiation within a few minutes of the blood being drawn.

After the initial developments to establish optimal handling, culture and observational parameters for multi-well lymphocyte growth and micronucleus detection, attention can turn to blood derived from individuals who have been subjected to total body irradiation (TBI). For these TBI individuals, blood samples are provided as they become available.

Samples are expected from approximately 60 TBI adult patients per year and 12 pediatric patients. All material is coded and the radiation exposures only made known to the investigators after the lymphocyte micronucleus assays have been undertaken in pair wise comparisons for unexposed and exposed samples. To improve the precision of our dose reconstruction, inter-personal sensitivity can be accounted for by using information from a sample exposed to a known dose. The procedure outlined here will be followed consistently for all TBI samples, and after micronuclei frequencies have been determined, the code will be broken and actual exposures compared with experimentally determined exposures.

Micronuclei in Lymphocytes: Use of small volumes of capillary blood in 384-well plates: As discussed above, in the second embodiment of the device capillary blood from a fingerstick is used, rather than peripheral blood from venipuncture. This should increase overall throughput dramatically after a radiation incident. The most common source of capillary blood is a disposable lancing device (Fruhstorfer H. Capillary blood sampling: the pain of single-use lancing devices. Eur J Pain 2000; 4:301-5; Garvey K, Batki A D, Thomason H L, Holder R, Thorpe G H. Blood lancing systems for skin puncture. Prof Nurse 1999; 14:643-8, 50-1), though laser skin perforators, such as the FDA-approved Lasette P200 (Cell Robotics Inc), are well-suited, having high patient acceptability (Burge M R, Costello D J, Peacock S J, Friedman N M. Use of a laser skin perforator for determination of capillary blood glucose yields reliable results and high patient acceptability. Diabetes Care 1998; 21:871-3).

As discussed above, the device should require no more than 50 μl of blood per sample, with the expectation that those individuals who produce less than this could be given a second fingerstick or laser perforation. In fact two groups have investigated a "micromethod" in which 100 μl of whole blood has been used for the micronucleus assay after radiation exposure both in vitro and in vivo (Paillole N, Voisin P. Is micronuclei yield variability a problem for overexposure dose assessment to ionizing radiation? Mutat Res 1998; 413:47-56; Gantenberg H W, Wuttke K, Streffer C, Muller W U. Micronuclei in human lymphocytes irradiated in vitro or in vivo. Radiat Res 1991; 128:276-81); in both cases, essentially identical results were obtained compared with the standard technique. Likewise two groups have reported successful results using a the micronucleus test from a capillary fingerstick (Lee T K, O'Brien K F, Wiley A L, Jr., Means J A, Karlsson U L. Reliability of finger stick capillary blood for the lymphocyte micronucleus assay. Mutagenesis 1997; 12:79-81; Xue K X, Ma G J, Wang S, Zhou P. The in vivo micronucleus test in human capillary blood lymphocytes: methodological studies and effect of ageing. Mutat Res 1992; 278:259-64). Therefore, a 50 μl amount is expected to be sufficient. In fact as discussed below, the second embodiment of the machine has been designed explicitly to avoid losing lymphocytes. Thus, Ficoll Hypaque density fluid can be added to a 75 μl hematocrit tube, which is centrifuged and imaged (see Centrifuge/Band Recognition Module, above). The tube is then robotically transported (with or without a known radiation exposure) to the multi-well plate, the tube is cut off below the lymphocytes layer, and all the remaining cells are washed into the appropriate well. All further cell handling steps take place inside the well, thus providing a system with essentially no loss of lymphocytes.

In term of experimental design, device optimization can proceed as earlier described, with comparisons between the slide-based approach and 96 well approach and subsequently a 384 well based approach. As discussed in detail above, a custom 384-well plate has been designed for use in some embodiments, with the same overall plate size as a standard plate, and with only a slightly smaller well area (16 mm2 vs 25 mm2) than standard 96-well plates.

γ-H2AX foci in lymphocytes can provide a "same-day answer" type biodosimeter. Previous work on γ-H2AX in human lymphocytes, as described herein. shows the high potential of this assay. To optimize the assay for use in the system described herein, the assay was automated, the post-exposure time dependence of the γ-H2AX foci in human lymphocytes was quantified and inter-personal variations of sensitivity for this assay was assessed, in terms of age and smoking status, and intrinsic radiosensitivity.

Briefly, the lymphocyte separation is carried out as described above. In the γ-H2AX assay, lymphocytes are not cultured, but are immediately delivered to multi-well plates where they are processed. Current technique is described in several publications (Rogakou E P, Boon C, Redon C, Bonner W M. Megabase chromatin domains involved in DNA double-strand breaks in vivo. J Cell Biol 1999; 146:905-16; Pilch D R, Sedelnikova O A, Redon C, Celeste A, Nussenzweig A, Bonner W M. Characteristics of gamma-H2AX foci at DNA double-strand breaks sites. Biochem Cell Biol 2003; 81:123-9). The speed of the various processes (cell fixation, processing and generation of antibody fluorochrome signal) can be maximized, so that the device can provide a final dosimetric answer within a few hours of the start of the processing.

Initial studies with ex-vivo irradiated blood will use a number of doses (0, 0.5, 2, 5, 10 Gy), as well as a number of times post exposure (0.5 h, 4 h, 24 h and 36 h) in order to quantify the dose dependent time dependence of the response. Ideally, all 20 dose-time points are covered by blood from each individual, which, based on preliminary studies should be possible. This allows further sub-analysis by age and by smoking status. Subsequently, the blood samples obtained from the TBI patients will allow us to test and refine the system calibration.

Micronuclei in blood reticulocytes, as a same day biodosimeter Just as the γ-H2AX assay provides a rapid biodosimeter useful for post-exposure times between 0 and ~30 h, so the assay for micronuclei in blood reticuloctyes provides a rapid biodosimeter useful for post irradiation times between roughly 24 and 48 hours (Lenarczyk M, Slowikowska M G. The micronucleus assay using peripheral blood reticulocytes from X-ray-exposed mice. Mutat Res 1995; 335:229-34). The assay can be modified as needed to allow full automation, and can be quantified in terms of the post-exposure time dependence of the assay, and the practicality of using ~50 μl of blood, from a capillary fingerstick or laser skin perforator, for the assay.

Mature erythrocytes are anucleate, but chromosomal damage events leading to micronuclei can appear in early reticulocytes after moving into the blood stream from marrow but before passing through the spleen where they are removed. Micronuclei can be detected at low frequency in red blood elements, and these frequencies are enhanced after individual exposure to chromosome damaging agents (Offer T, Ho E, Traber M G, Bruno R S, Kuypers F A, Ames B N. A simple assay for frequency of chromosome breaks and loss (micronuclei) by flow cytometry of human reticulocytes. Faseb J 2004), such as ionizing radiation.

In a first embodiment described here, peripheral blood is separated into its constituents, with the red blood cells separated from serum and white blood cells. In a similar-fashion to that outlined above for mononuclear cells, a sample of red blood cells will be drawn from the lower portion (Pawar V B, Prabhu A. Isolation of large numbers of fully viable human reticulocytes using continuous Percoll density gradient. Clin Lab Sci 1991; 4:360-4) of the Vacutainer tube, and smeared by the wedge technique onto a microscope slide, while the comparison samples will be placed in the well of a 96-well plate. Unlike the micronucleus assay in lymphocytes, no cell handling procedures are required, but rather cells are immediately processed in situ, with rinsing, vacuum filtration and fixation, prior to staining with DAPI. This DNA binding specific fluorochrome renders the micronuclei present in reticulocytes visible as small, bright spherical or near-spherical encapsulated micron-sized objects.

Initial protocols studies can be done using unirradiated blood from healthy human volunteers. Experiments carried out with this assay using ex-vivo irradiated blood from human volunteers will be of limited utility, so studies can be undertaken using reticuloctyes from the total body irradiation (TBI) patients—in fact using the same blood samples from which the lymphocytes will be extracted. For each TBI patient, an assay can performed for micronuclei in reticulocytes at 24, 48, and 72 hours post exposure.

High-throughput automated processing and analysis of micronuclei in exfoliated bladder cells from urine, and exfoliated buccal cells is also contemplated. Urine also contains exfoliated cells shed from the lining of the bladder. Such cells can be collected and can be shown to express enhanced levels of micronuclei following the exposure of an individual to DNA damaging agents (Moore L E, Warner M L, Smith A H, Kalman D, Smith M T. Use of the fluorescent micronucleus assay to detect the genotoxic effects of radiation and arsenic exposure in exfoliated human epithelial cells. Environ Mol Mutagen 1996; 27:176-84; Sarto F, Finotto S, Giacomelli L, Mazzotti D, Tomanin R, Levis A G. The micronucleus assay in exfoliated cells of the human buccal mucosa. Mutagenesis 1987; 2:11-7; Titenko-Holland N, Moore L E, Smith M T. Measurement and characterization of micronuclei in exfoliated human cells by fluorescence in situ hybridization with a centromeric probe. Mutat Res 1994; 312:39-50). Therefore the expression of micronuclei in urothelial cells following exposure to ionizing radiation has the potential to reflect the dose of radiation received. Such exfoliated cells express their micronuclei in the mononucleate state and cannot be further cultured. The intent here is to collect urine from the same group of total body irradiation (TBI) patients providing peripheral blood for the assessment of pre- and post TBI micronucleated lymphocytes. In each case the radiation exposure history of the samples will be blinded at the time of processing.

Prior to these studies being undertaken the protocol for urothelial cell analyses can be established using urine from healthy volunteers. The standard technique for exfoliated urothelial cell assays involves centrifuging the sample, washing and concentrating before placement on a microscope slide and staining with dyes prior to examination by standard light microscopy. This approach is not amenable to high throughput, high speed image analysis, we shall develop a single test tube procedure whereby the sample is placed in a centrifuge tube with an optical quality base. After spinning and removal of the supernatant, we will stain with the DNA specific DAPI fluorochrome prior to examination for the incidence of cells with micronuclei. DAPI provides situations with the least amount of background for subsequent imaging. A robotic handler will place tubes directly onto the imaging system of our Phase I device.

Exfoliated buccal cells from the oral cavity can be collected with a brush or spatula and have also been shown to express micronuclei in humans after exposure to chromosome damaging agents including ionizing radiation (Belien J A, Copper M P, Braakhuis B J, Snow G B, Baak J P. Standardization of counting micronuclei: definition of a protocol to measure genotoxic damage in human exfoliated cells. Carcinogenesis 1995; 16:2395-400; Moore L E, Warner M L, Smith A H, Kalman D, Smith M T. Use of the fluorescent micronucleus assay to detect the genotoxic effects of radiation and arsenic exposure in exfoliated human epithelial cells. Environ Mol Mutagen 1996; 27:176-84; Tolbert P E, Shy C M, Allen J W. Micronuclei and other nuclear anomalies in buccal smears: methods development. Mutat Res 1992; 271: 69-77). They are handled in a similar manner to the urothelial cells, and provide an additional potential indicator of radiation exposure.

In some embodiments, protocols are optimized and the device calibrated using unirradiated samples from healthy human volunteers. For actual testing, the device will use biofluid (urine, blood, saliva, sweat) samples from patients already being exposed to total body irradiation (TBI) as part of their medical therapy, as well as healthy non-irradiated volunteers. For example, samples of blood and urine from irradiated subjects collected elsewhere (e.g. at Pittsburgh and MSKCC) will be processed and constituent parts distributed for measurement and assessment. Micronuclei, γ-H2AX foci, and functional genomics changes in blood samples measured. In addition, blood from anonymized healthy volunteers will be collected and then irradiated ex vivo and processed as above. Blood and urine samples will also be collected from patients undergoing total body irradiation prior to transplantation procedures. 12 cc or 25 cc of blood and 30 cc or 60 cc of urine will be collected. The samples will be sent to Columbia University Medical Center or to Harvard University School of Public Health for testing according to the methods and using the device as described herein. Blood samples a) from healthy volunteers collected at the NCI through the Department of Transfusion Medicine, and b) collected from TBI patients at MSKCC and Pittsburgh, will be also studied for the production of radiation-induced γ-H2AX foci and for metabolomics products.

Blood, urine, saliva and sweat samples (biofluids) will be collected from patients planned to receive total body irradiation. Samples will be collected before and after exposure to radiation. The samples are coded, and the investigators involved in the measurements will know only the radiation dose, the age, gender, and smoking status of the subject from which the sample was taken. The collection of biofluid samples will be collected before and after the subjects received whole-body irradiation. Blood samples will be obtained either by venipuncture, through a lancet fingerstick, or through a laser skin perforator.

Figure 40:
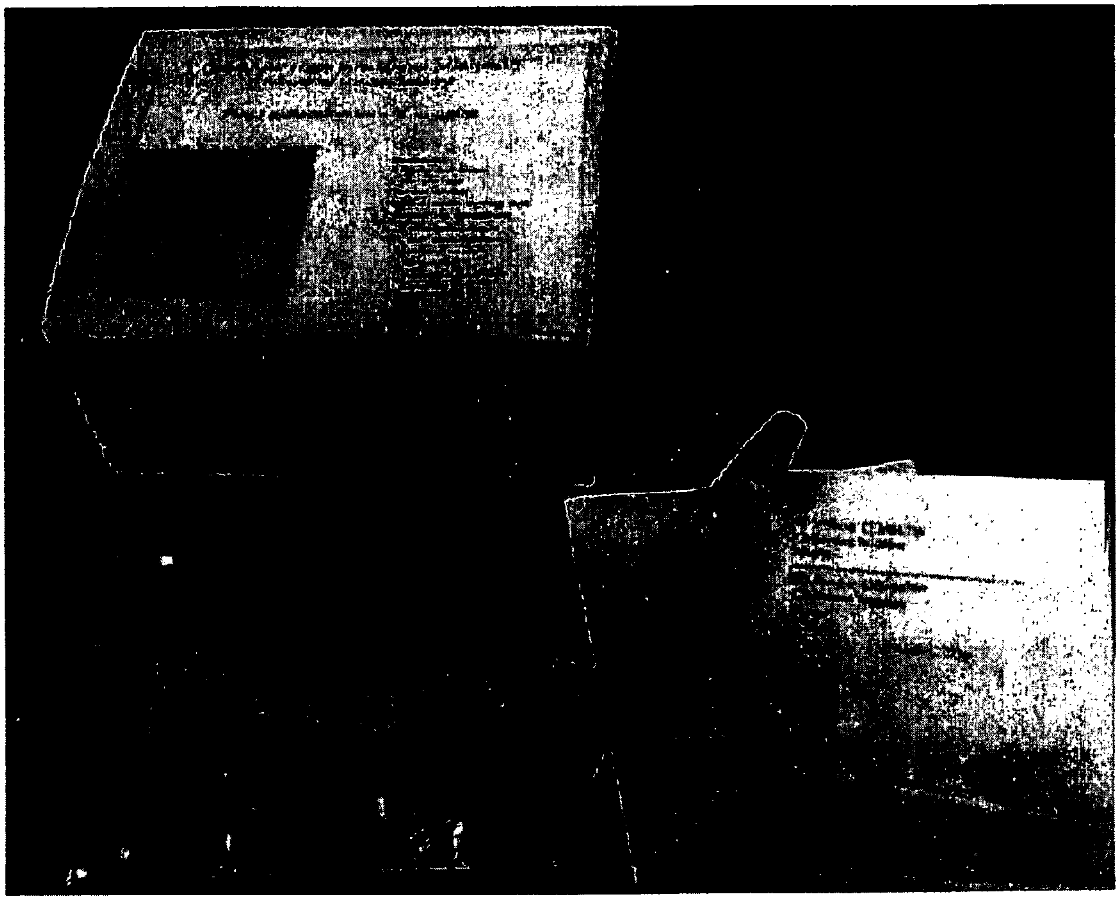
FIG. 40 shows a field collection kit.

A major challenge posed by local public health authorities is the actual sample collection in the field from tens of thousands of individuals. To simplify sample collection, some embodiments relate to a kit (FIG. 40) containing matched bar-coded capillaries and data collection cards, a capillary holder as well as anything else required by the sample collector (gloves, lancets, etc.). The capillary holder has also been designed such that three holders exactly fit in one centrifuge bucket, simplifying the input stage to the biodosimetry workstation. The capillary holder will also be pre loaded with capillary sealing putty and gelled separation medium, to provide a simple collection protocol compatible with the optimal lymphocyte separation requirements (50 μl blood layered on 50 μl separation medium).

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example

Barcoding Capillary Tubes

Figure 41:
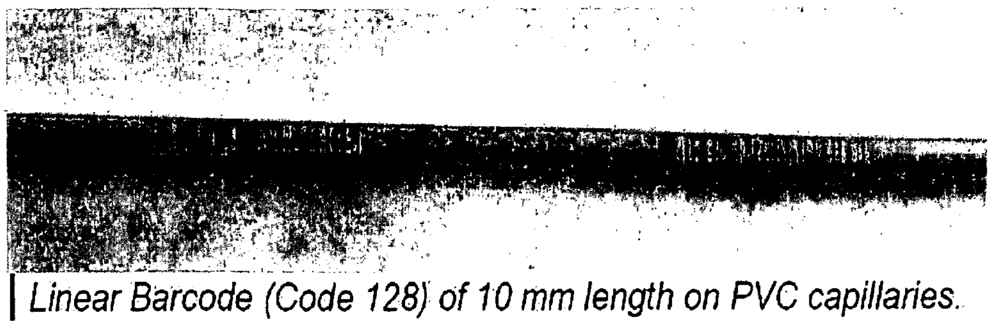
FIG. 41 illustrates a capillary having a laser-etched bar code identifier in accordance with an embodiment of the invention.

One of the major challenges overcome by embodiments of the invention described herein is traceability. A method and system is needed that is operable with tens of thousands of samples per day arriving from multiple collection facilities, and that is able to correlate between the results of each sample and the identifying information of the individual. Unambiguous (and foolproof labeling of small plastic capillary tubes (outer diameter ~2 mm) is a challenge. There are no commercial barcoding or RFID technologies for capillary tubes. One solution is to laser-etch a 10-digit barcode on each capillary, as shown in FIG. 41.

Capillary blood sampling is increasingly used for screening (for example, blood gas analysis) in a hospital setting, as compared with venipuncture. This is because capillary blood sampling is a much easier technique that can be performed by medical technicians, causes less discomfort to the patient, and has a much lower frequency of adverse events. Until now, however, there has not been a practical electronic ID system for capillary tubes due to their small outer diameter (~2 mm), raising the possibility of misidentified samples.

Accordingly, a novel barcode system for capillary tubes was developed based on laser etching of PVC tubes, and the ease of both writing and reading the barcodes has been confirmed. Briefly, 1-D barcodes (encoding ten numeric digits or 1011 samples) were marked on PVC capillary samples using a 350 nm wavelength UV laser system. The code was approximately 10 mm long and 1.5 mm high. The barcode was marked using power of 1 Watt and speed 45 ips. Resolution achieved was 100 μm, and the cycle time was 0.16 seconds. The barcodes were successfully read by a high-resolution stationary scanner.

This will allow the capillary to arrive at the collection center pre-labeled, reducing the chance of error. It has been shown that by using this technique, the capillaries can be reliably labeled and identified using an automated system.

Example

RFID Labels

RFID labels (Philips ICode I smart IC, part SL1 ICS31; 512 bit, 13.56 MHz, 97 pF) were also successfully tested for application to PVC hematocrit capillaries. These can be read by a ACG HF Multi ISO reader with a USB or RS-232 interface. An evaluation kit to test suitability is used. However, the cost (70 cents/piece) and size of the labels (30×7 mm) are less well suited.

Although the transport tubes and well plates can be tagged by bar coding, an RFID solution would be preferable; because the tubes can be identified easily on entry to the system and the archival plates can be located and retrieved. Collision issues can be addressed. Individual wells can be readily identified with alphanumeric indices and do not need individual tagging.

Figure 42:
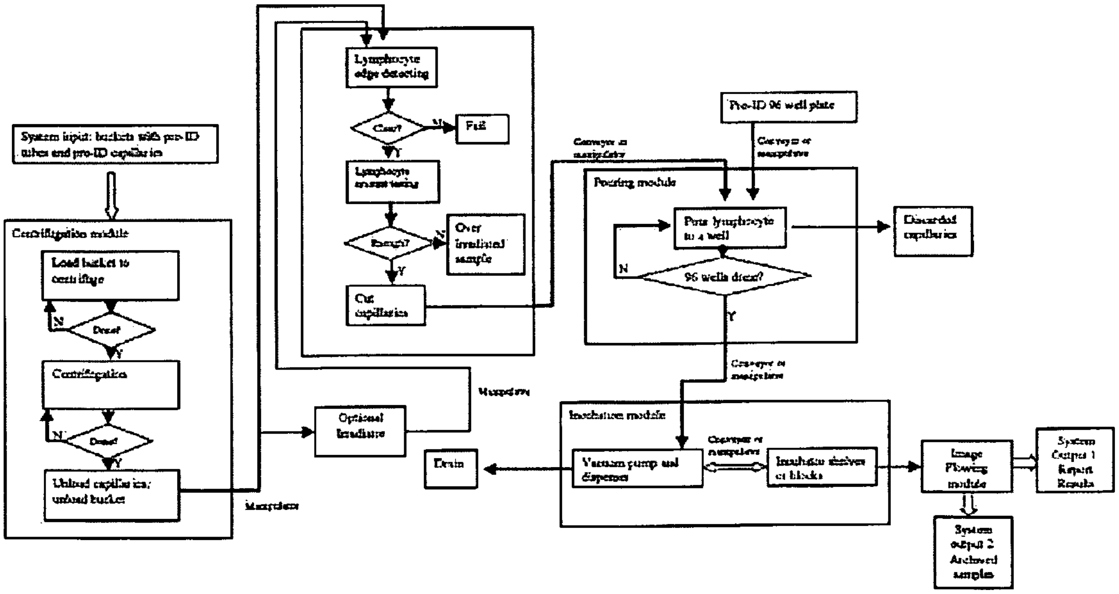
FIG. 42 depicts a flow diagram of an exemplary method of the system.

A diagram showing an embodiment of the method and system described herein is shown in FIG. 42.

Design parameters of some embodiments of the invention disclosed herein are set forth in the following table.

| Design Parameter | Value |
|---|---|
| Centrifuge Module | |
| Relative centrifugation factor (speed) | 0-2000 g |
| Centrifugation time | 5-15 minutes |
| Capillary | |
| Length of Capillary | 75-170 mm |
| Volume of Capillary | 50 μl of blood + up to 50 μl of separation medium |
| Material | Plastic (PVC). |
| Incubation Module | |
| Incubation period for a single sample | 1-3 hours (pre-mitotic) and 1-2.5 days for the micronuclei |
| Assays | micronucleus and pre-mitotic (e.g. γ-H2AX) |
| Throughput | 6,000 samples/15 hr-day (phase 1) 30,000 samples/15 hr-day (phase 2) |
| Microplate | |
| Number of wells | 96-wells (phase 1), 384-wells (phase 2) |
| Footprint | Standard multi-well plate (130 mm × 85 mm) |
| Geometry of well cross-section | Circular (phase 1), square (phase 2) |
| Design | Off-the-shelf (phase 1), custom-made, (phase 2) |
| Filter at the base of each well | 0.6 μm pore from Millipore Corp. |
| Maximum volume capacity of the well | 300 μl (phase 1) |

In other embodiments, the relative centrifugation factor can be up to 15,000 g. In one embodiment, smaller capillaries can used.

Example

Blood Collection Module

In one embodiment, blood collection is performed by finger stick and the blood collected into capillaries. Commercially available glass capillaries from QBC diagnostics were used. These tubes are internally coated with an anticoagulant and a dye which is potentially lethal to lymphocytes.

In one embodiment, plastic capillaries coated with an anticoagulant are used. Capillaries used for the micronucleus assay are also coated with a stimulant to reduce the incubation time. Capillaries used for the pre-mitotic assay are coated with a fixative, as the lymphocytes must be fixed at the time of collection to preserve their original state.

In one embodiment, the cap for these capillaries contains a gelled separation medium to enhance the lymphocyte separation.

Though the expected required sample volume is 50 μl (see below), some embodiments of the system can accommodate capillaries with a capacity of 50-100 μl in order to take into account inclusion of lymphocyte separation medium. The centrifugation parameters and separation method are discussed below.

Each capillary will be uniquely identifiable for correlating the sample with a patient. The identification and tracking of samples is discussed below.

Figure 43:
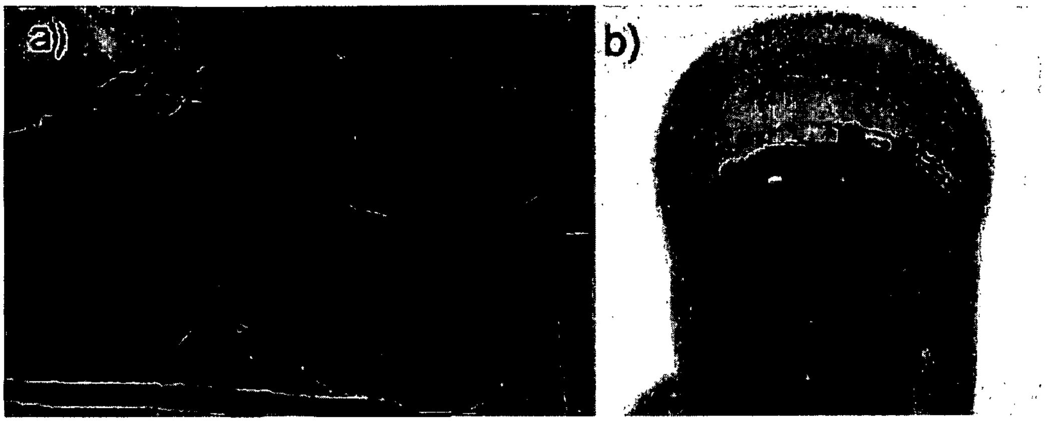
FIG. 43 illustrates dilution tubes modified to accommodate capillaries for shipping and centrifugation in accordance with an embodiment of the invention.

At the collection point the capillaries will be filled with blood, capped (thus adding the separation medium) and placed in a container for shipping to the workstation where it will be dropped as a whole into the centrifuge for lymphocyte separation. For shipping/centrifugation containers 50 ml dilution tubes, modified to accommodate 24 capillaries each, which will be inserted in a traditional centrifuge as illustrated in FIG. 43.

In another embodiment a custom insert containing 44 capillary-sized holes will be used. The holes will be pre loaded with sealing material and gelled separation medium such that inserting the capillary will add the required amount of separation medium and seal the capillary bottom. The insert is designed to fit directly into the centrifuge.

Example

Irradiation Module

In some embodiments, an irradiation module, based on a radioactive source array, is used to normalize the radiation sensitivity of the clients. A new compact x-ray irradiation system which contains no radioactive sources or components was designed specifically for irradiating blood in capillaries.

Briefly, a cylindrical geometry is used with the sample at the center. There will be a small diameter, cylindrical support for the anode material which will be plated on its outside surface. Outside of the anode structure there will be a larger cylinder of quartz glass which will have an electron emitting material on its inner surface. There will be vacuum between these cylinders as well as electrical isolation for the accelerating voltage. The final cylinder, outside of these, will be an aluminum reflector. In the intervening space there will be five UV lamps to induce the necessary electron current.

In order to get uniform exposure in a capillary, the attenuation length should be comparable to the capillary diameter; this dictates the X-ray energy and therefore the anode material. In one embodiment, copper K X-rays, which have an energy of about 10 keV are used. The cross section for production of K X-rays with electrons rises from a threshold equal to their energy and reaching a maximum at three times that, or 30 keV in this case. Because 10 keV X-rays are strongly attenuated by most materials, the anode support will be made of beryllium.

Example

Lymphocyte Separation Module

Figure 44:
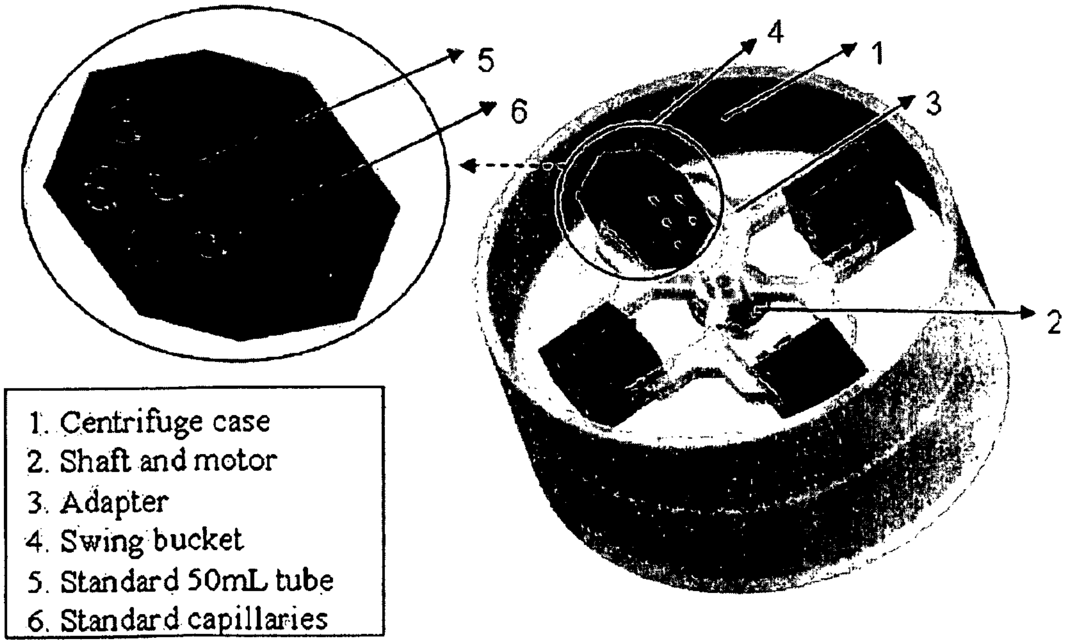
FIG. 44 illustrates a design model of a centrifuge adapted for use with an embodiment of the invention.

Separation of the lymphocytes from whole blood is done by centrifugation. An extensive review of existing centrifuges, rotors and buckets was conducted, and the design requirements were set. A computer-aided-design (CAD) model of both buckets and rotor of an existing centrifuge, used for the experiments was developed using PRO/Engineer™ as illustrated in FIG. 44. In this embodiment, the centrifuge is a Sorvall Legend T which has four buckets, each containing seven modified 50 ml tubes, with 24 capillaries each (a total of up to 672 capillaries). The bottom chamber of the centrifuge contains the motor, control equipment and interface panels.

Design requirements of electromagnetic clutches and brakes were recognized; a review of existing electromagnetic braking systems was also performed. A preliminary analysis of centrifuge unloading was performed and several design concepts of robotic grippers for the capillaries, bucket and rotor were also considered. Custom-made designs of both single capillary and batch capillary grippers were compared.

The expected centrifugation time for the capillaries represents the throughput limit for our system. Several centrifugation experiments resulted in an estimate of centrifugation time of 10 minutes ±5 minutes. The centrifuge will have an adjustable angular velocity, and will be capable of delivering centrifugal accelerations up to 2000 g.

Figure 45:
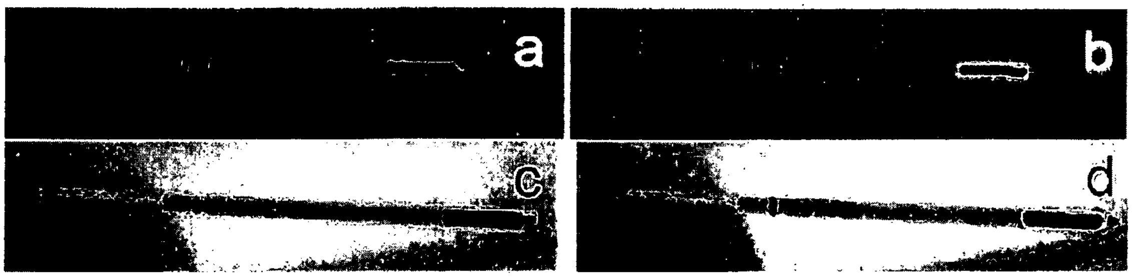
FIG. 45 illustrates image segmentation of a capillary accomplished using an embodiment of the invention.

In some embodiments, after centrifugation, the lymphocytes form a thin layer above the compacted red blood cells (RBCs) and separation medium. The samples will be imaged for lymphocyte band recognition. To this end, simulations for automatic segmentation of lymphocyte band on digitized images of actual centrifuged capillaries were performed using an image recognition software package (MATLAB). FIGS. 45*a* and 45*c* depict the input color images acquired by a digital camera. These images are based on centrifugation results with glass hematocrit capillaries.

Similar investigations will be conducted on centrifuged plastic hematocrit capillaries in the future. Various methods, including a gradient based approach, morphological image processing and color based region segmentation, were investigated to isolate the boundary of the RBCs that need to be discarded. Among these, morphological methods on grayscale images produced the best results. This automatic segmentation program outputs grayscale images with RBC boundary detection, as shown in FIGS. 45*b* and 45*d*. Based on these observations, very-high quality color images would be required for color based manipulation and segmentation, while grayscale image manipulation produces reliable and repeatable results. In order to increase the computational speed, some embodiments use a compiled language (C++).

After centrifugation, lymphocytes contained in each capillary have to be identified and counted for pre-screening purposes. To this end, a review of principles and methods of light scattering for cell identification and counting was conducted.

Upon completion of the lymphocyte identification and quantification, the lymphocytes have to be transferred from the plastic capillary tube to a well plate by a robot for further analysis. More specifically, the lymphocytes need to be extracted from each capillary and poured into the wells of the well plate. Three alternative extractions methods have been identified: traditional mechanical cutting, punctuation and non-contact laser cutting. In one embodiment, laser cutting minimizes the possibility of cross-contamination of the samples. One of the challenges is to reduce the heat-affected zone so as to decrease the influence of heat transfer, associated with the cutting, on the blood samples. To this end, some embodiments use an integrated laser-cutting/marking system (based on the use of existing devices from Control Systemation Inc.), capable of cutting capillaries filled with blood samples and of producing a reduced heat-affected zone.

Example

Lymphocyte Incubation

The incubation module and liquid handling systems should be capable of processing both the pre-mitotic and the micronucleus assays. The processing time for the pre-mitotic assay is expected to be between 1 and 3 hours. Processing time for the micronucleus assay is expected to be 2.5-3 days. During this process, various reagents need to be added to or drained from the wells. Given the system requirements, the typical number of plates that will be simultaneously inside the automatic incubator is 200-300 for all contemplated embodiments.

Several design concepts have been analyzed for the implementation of the incubation module. The use of off-the-shelf automatic incubators, modified incubators and custom-made incubators was considered. Existing automatic incubators feature up to 1000 positions. However, the single-position (i.e., one microplate at a time) of existing automatic trays strongly hampers the throughput of these systems. In order to increase the throughput, design modifications (such as the addition of i) an internal robot manipulator, ii) one/two linear conveyors, iii) input/output temperature/humidity/CO2 control buffers and/or two side-mounted gantry robots) to existing incubators were considered. To further increase the throughput, concepts for custom-made robotic incubators, featuring an internal conveyor along with internal vacuum-to-waste modules were considered.

With reference to the liquid handling system, several existing robotic liquid/plate handlers were investigated. Existing robotic liquid/plate handlers usually consist of a gantry robot and an end effector for adding reagents to standard 96 well plates. The volume range of reagent that can be added per well is typically 1-200 μl, 20-300 μl or 40-1000 μl. For the micronucleus assay (see Table below), the most suitable volume range for the dimensioning of the pipette tips of the robotic liquid/plate handler is 20-300 μl. However, two operations, OP4 and OP10 (see Table below), might not be performed accurately because the volume of reagent to be added is equal or below 20 μl. Additionally, robotic liquid/plate handlers (independently from the pipette tip volume range) lack crucial built-in automatic functionalities, such as agitation and draining (negative pressure) and therefore operations OP2a, OP5, OP6 (partially), OP7, OP8 (partially), and OP11 are not supported. In order to automate the operations of the table below that existing robotic liquid/plate handlers do not perform, the use of multiple vacuum-to-waste units and orbital shakers is contemplated.

Some existing robotic liquid/plate handlers can support the gamma-H2AX protocol, being capable of automating cell fragmentation, selective extraction, and affinity purification. The challenge here is to make the robotic liquid/plate handler compatible for both protocols (micronuclei and pre-mitotic). While the end-effector is typically equipped with a 96-well plate gripper, these systems generally lack online motion planning capabilities. If a faulty condition takes place within the workspace of the gantry robot (e.g., a plate falls from the tip of the gantry robot), the system is not capable of automatically recovering from this faulty condition. This applies also to the robotic liquid/plate handlers that use an optical sensor to recognize liquid stocks in the supply vessels, control accessories on the work surface, control the positioning of the dispensing, and check if pipette tips/labware match the requested protocol. Even if the system can detect the error, it is not capable of acting in order to recover from the faulty condition (e.g., the fallen plate lies in a position which is not parallel to the XY stage of the gantry robot). In this regard, the use of a dexterous and intelligent manipulator, which services the vacuum-to-waste stage, the robotic liquid/plate handler, the multi-position orbital shakers, and the incubator, is used.

TABLE

Current Micronuclei Assay for Lymphocytes-Phase 1 biodosimetry

| OP | Liquid/Plate Handling Operation | Volume Handled | Built-in Functionality of Existing Robotic Liquid/Plate Handlers |
|---|---|---|---|
| 1 | Pour lymphocytes + plasma into well. | 30-100 μl | Not available |
| 2a | Suck out liquid through filter | same as above | Not available |
| 2b | and fill with culture medium | 75% of well capacity (225 μl for phase 1) | Available |
| 3 | Incubate 37 C. humid air + 5% $CO_2$ | | Not available |
| 4 | After 44h add cytochalasin-B (6 μg/ml) | in 5-20 μl of saline | Available (limit: 20-300 μl) |
| 5 | After 28h, suck out medium through filter | 75% of well capacity | Not available |
| 6 | Add cold (4° C.) 0.075 M KCl and suck out medium through filter immediately. | 75% of well capacity | Partially available (only addition of cold (4° C.) 0.075 M KCl is available) |
| 7 | Re-suspend in fixative, agitate to prevent clumps and suck out medium through filter | 75% of well capacity | Not available (only fixative addition is available) |

TABLE-continued

| Current Micronuclei Assay for Lymphocytes-Phase 1 biodosimetry | | | |
|---|---|---|---|
| OP | Liquid/Plate Handling Operation | Volume Handled | Built-in Functionality of Existing Robotic Liquid/Plate Handlers |
| 8 | Wash cells with fixative (without formaldehyde) twice, i.e. fill wells and suck medium through filter. | 2 × 75% of well | Partially available (only fixative addition is available) |
| 9 | Add medium | 75% of well capacity | Available |
| 10 | Stain cells with 10% Giemsa in potassium phosphate buffer (pH 7.3) and acridine orange (10 μg/ml in phosphate buffered saline pH 6.9) | 5-20 μl of saline | Available (limit: 20-300 μl) |
| 11 | Aspirate medium through filter. | 75% of well capacity | Not available |

Example

Transfer of Samples to Permanent Substrate

The final step in preparation of the samples for viewing by the image analysis system is to transfer the filter bottoms of the multi-well plates to a supporting substrate. In some embodiments, a rewettable adhesive (poly-vinyl alcohol), similar to that used on postage stamps, can be applied to a solid substrate. The gluing is accomplished with residual moisture on the filter bottom after the last wash.

One embodiment obtains a bond by placing the liquid adhesive in the wells, drawing it through the filter under vacuum and then applying the wet plate to a porous substrate to dry. Moreover, a fully hydrogenated form of the adhesive was used, which is not re-wettable and therefore will form a more stable surface suitable for archival storage. Some embodiments will also include an anti-fade agent to further improve stability. The substrate is a non-fluorescent semi-rigid expanded plastic from Porex, Inc.

Another embodiment obtains a bond by using an adhesive film such as an ELISA plate sealer and a mechanical punch which transfers the filter bottoms, onto the film. The film is then sealed by lamination to prevent regions not containing a filter from remaining sticky.

Example

Imaging Module

Figure 47:
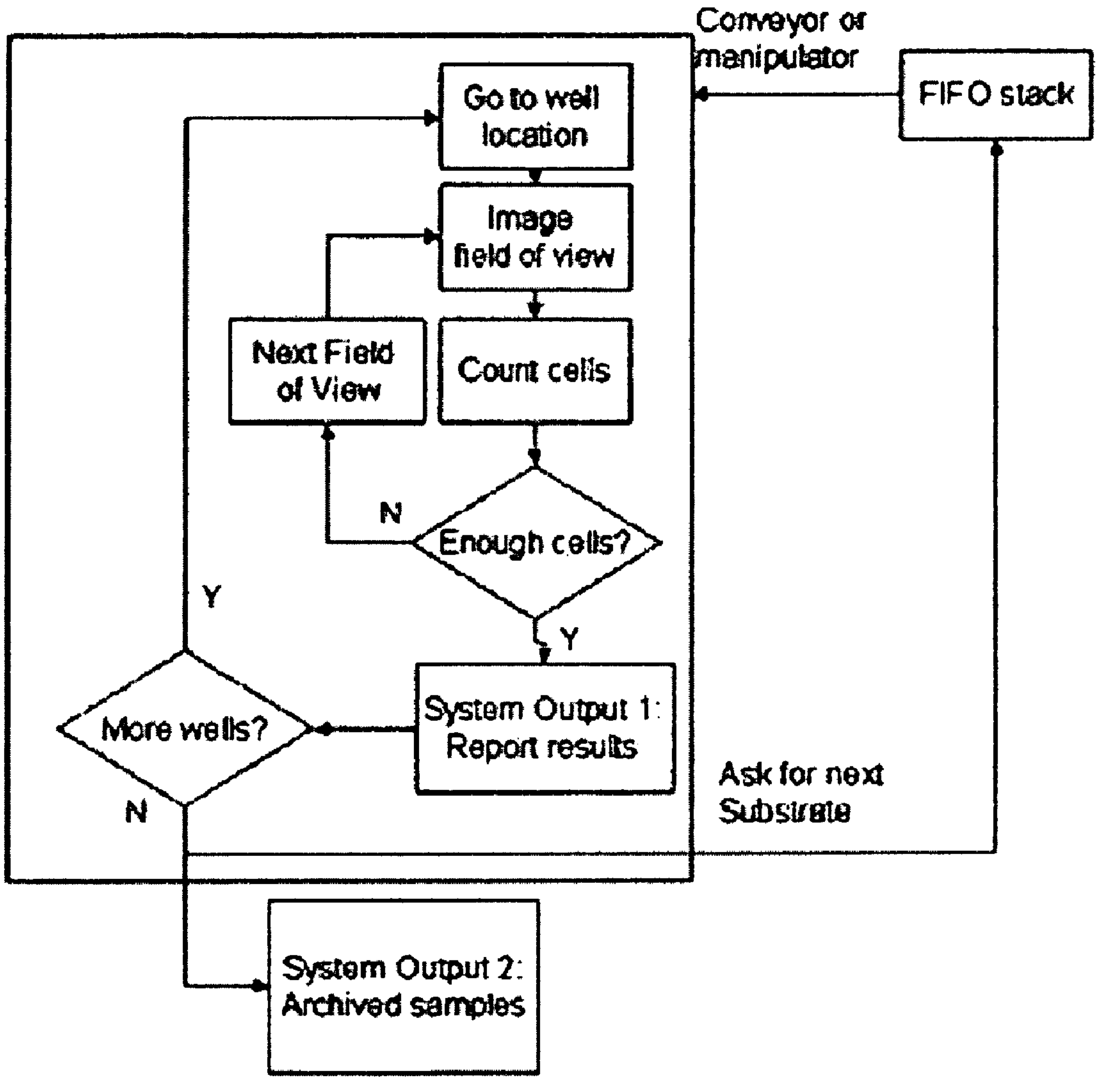
FIG. 47 depicts a flow diagram of an imaging process in accordance with an embodiment of the invention.

For the imaging, a modified version of the microscope used for the microbeam endstation (Randers-Pehrson G, Geard C R, Johnson G, Elliston C D, Brenner D J. The Columbia University single-ion microbeam. Radiat Res 2001; 156:210-4) is developed, connected to a high speed camera (150 fps, 1024×1024, CMOS camera) and frame grabber board. The flow diagram of the imaging system is shown in FIG. 47. The optical path is divided in two by a cold dichroic mirror (rather than a cube switcher), so that the image of small red-fluorescing beads is continuously reflected into the focusing channel, while the main image goes on undisturbed. The tube lens on the focus channel has an added weak cylinder lens. This allows a simple, one-step focusing routine; the aspect ratio of the bead will be proportional to the focus error, allowing fast automated corrections with a single picture. A fast piezo stage makes the corrections needed.

Figure 48:
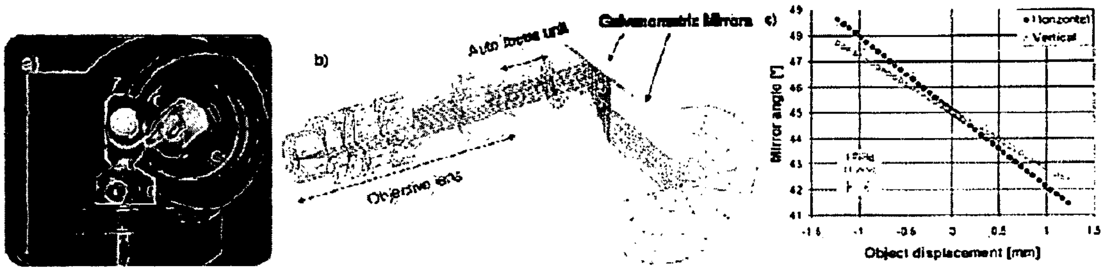
FIG. 48 illustrates a method and results of operating a microscope with a 2D scan head in accordance with an embodiment of the invention.

A preferred embodiment improves on standard microscope design by inserting a 2D scan head, illustrated in FIG. 48 just above the objective lens. This enables rapid switching between adjacent fields of view of the microscope, faster than can be done with a mechanical stage. Extensive simulations have been run to determine the required mirror size and scan angles. A large mirror is too slow to rotate and costs time in switching between fields of view. A small mirror does not collect light efficiently from external fields of view and require longer exposures in the camera. The optimal mirror size was found to be approximately 20 mm.

In these simulations the objective lens design was taken from Nikon, the auto focus module was replaced with a gap and the location of the mirrors was taken from the design drawings. FIG. 48*c* shows the required adjustments to the mirror to compensate for a movement of the object. As expected, it was observed that the mirrors are practically decoupled and each one compensates for deflections in an orthogonal axis.

In some embodiments, a control software using Visual C++, which has the flexibility needed for this work is used.

Example

Sample Identification and Tracking

A review of methods for capillary labeling and tracking was conducted and promising results were obtained with laser marking of hematocrit capillaries. Three main factors need to be considered while considering various technologies for sample identification: errors, time factor and cost. The workstation should be able to i) track samples through the complete process, ii) create sufficient redundancy levels and iii) maintain complete database of sample data. Bar-coding and radio-frequency identification (RFID), one a widely used technology and the other, an emerging technology, were analyzed in detail for applications to the workstation under development. Results of a comparative analysis among passive, active RFID and barcodes are summarized in the following table.

| | BARCODES | PASSIVE RFID | ACTIVE RFID |
|---|---|---|---|
| Modification of Data | Un-modifiable | Modifiable | Modifiable |
| Security | Minimal Security | From minimal to highly secure | Highly Secure |
| Amount of Data | Linear 8-30 Characters 20: 7200 Numbers | 64kB | Up to 8Mb |
| Cost | Low (<few cents) | Medium (>25 cents) | Very High (>10-100S) |
| Life Span | Short unless etched into metal | Indefinite | 3-5 Yr battery Life |
| Standards | Stable and agreed | Evolving to agreed standards | Evolving open standards |
| Reading Distance | Line of sight (3-5 ft) | No contact or line of sight (up to 50 ft) | No contact or line of sight (up to 100 m or more) |
| Potential Interference | Optical barriers e.g. Dirt and object between tag and reader | Environment or fields that affect transmission of RF | Limited barriers since broadcast signal from tag is strong |
| Multiplicity | 1 at a time | Hundreds of tags nearly simultaneously | |

Example

Dimensioning of Robotic Systems

At the design level, a series of potential robotic systems in charge of manipulation and transportation operations of capillaries and well-plates have been identified. Both hardware and software specifications and attributes of robotic systems, conveyors, robot manipulators (modular, gantry, serial, parallel), linear robots and rotary actuators, are being analyzed.

Several off-the-shelf robotic systems are under testing in a CAD environment. CAD models of both modules and workstation layout have been generated in order to perform "reach and interference" analyses between robot manipulators and the rest of the workstation components (incubator, centrifuge, liquid handling system, etc.). To automate the capillary and plate handling operations, two robotic systems are used: a robot manipulator, responsible for capillary/tube/bucket handling-related operations, and a second, plate-handling, robotic system in charge of the plate handling-related operations.

Both the capillary handling robotic system and the plate handling robotic system are capable of performing online motion planning, based on encoder, vision, force and proximity sensor readouts. This allows the system to quickly recover from potential faulty conditions (e.g., accidental falls of capillary/plate from the gripper). To this end, an analysis of specifications and attributes of different types of intelligent serial robot manipulators has been conducted. The use of different types of robot manipulators, such as selective compliant assembly robot arms (SCARAs), five and/or six-degrees-of freedom robots, is currently under analysis. SCARAs are very suitable for pick and place operations.

Example

Optimization of Lymphocyte Separation Protocol

Both assays require separation of lymphocytes from whole blood. Accordingly, the optimal methodology for extracting lymphocytes from whole blood has been explored. Tests have been run using glass capillary tubes (QBC diagnostic AccuTube) to optimize the lymphocyte separation protocol by centrifugation. The capillaries can hold up to 100 μl of solution and are internally coated with sodium heparin (10 μg) and K2EDTA (0.33 mg). The anticoagulant mixture is optimized for the 100 μl of blood.

Figure 49:
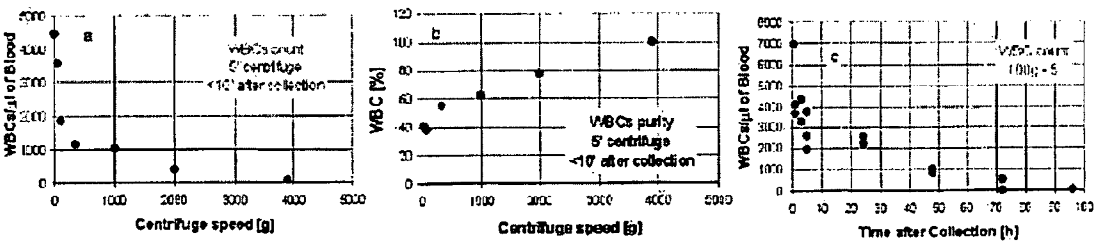
FIG. 49 illustrates the effect of centrifuge speed and elapsed time from blood collection on sample quality.

The centrifugation parameters (speed and time) have also been optimized, as this has a large impact on the design of the whole system. FIG. 49*a* shows the number of lymphocytes counted per μl of blood as a function of the centrifuge speed (5 min centrifugation time). In order to facilitate the lymphocytes erythrocytes separation, 50 μl of histopak (1.077 g/ml) has been added to the capillaries Although as many as 80% of the lymphocytes present in the blood sample can be collected, at low centrifugation speeds the lymphocyte solution is still contaminated by some erythrocytes FIG. 49*b*.

The number of lymphocytes retrieved as a function of elapsed time from blood collection has been investigated. As expected, the number of lymphocytes retrieved decreases linearly down to about 15% after 2 days FIG. 49*c*. This limit is the time allowed between the blood collection and analysis.

Example

Optimization of Lymphocyte Incubation in 96-Well Plates

Another important and novel aspect of our design is the incubation of lymphocytes in filter-based multiwell plates. This is done to facilitate medium exchange and the addition/removal of reagents without needing to pellet the lymphocytes each time.

In a first embodiment of the device the lymphocytes are incubated in 96 well plates (Multiscreen plates from Millipore), while in a second embodiment of the device they will be incubated in custom designed 384 well plates.

The filter used for this application must be carefully selected: it must be non-fluorescent, to allow imaging of the lymphocytes, it must be easily detachable, and the pore size must be optimal.

In order to test the effect of pore size, whole blood was used and red blood cells were selectively lysed using 0.85% ammonium chloride. 0.45 μm pores tend to get clogged by the lysed red blood cells, resulting in a very slow removal of liquid from the wells, though this is not a problem for centrifuge-separated lymphocytes. On the other hand, 1.2 μm pores were sufficiently wide to allow the lymphocytes to enter and become lodged in the pores, and thus could not be extracted for imaging. Accordingly, 0.65 μm pore-size plates were selected.

In one embodiment, the lymphocytes within each capillary after centrifugation are separated from the red blood cell ("RBC") pellet and dropped within the microwell. Cultures are set up in each well with complete medium containing 15% heat inactivated FBS, PHA (M-form), L-glutamine and antibiotics. After incubation at 37° C. for 44 hours cytochalasin B (in DMSO) was added in order to block cytokinesis. After 28 hours with the cytochalasin B at 37° C., cells are treated with hypo and fixed in a fixative such as, for example, Carnoy's fixative. The liquid already present within each well is drained out by the application of a positive pressure before the addition of any fresh reagents. Finally, the cells are allowed to dry and stained with an agent or combination of agents such as Acridine Orange and DAPI and viewed under a fluorescent microscope.

Example

Automated Cytogenetic Imaging

MetaSystems has automated cytogenetic imaging platforms, such as the Metafer system (Hande M P, Azizova T V, Geard C R, Burak L E, Mitchell C R, Khokhryakov V F, et al. Past exposure to densely ionizing radiation leaves a unique permanent signature in the genome. Am J Hum Genet. 2003; 72:1162-70; Mitchell C R, Azizova T V, Hande M P, Burak L E, Tsakok J M, Khokhryakov V F, et al. Stable intrachromosomal biomarkers of past exposure to densely ionizing radiation in several chromosomes of exposed individuals. Radiat Res 2004; 162:257-63). Briefly described herein is experience with this platform (Schunck C, Johannes T, Varga D, Lorch T, Plesch A. New developments in automated cytogenetic imaging: unattended scoring of dicentric chromosomes, micronuclei, single cell gel electrophoresis, and fluorescence signals. Cytogenet Genome Res 2004; 104:383-9), which provides cytogenetic-based automated imaging. The Metafer platform features motorized x, y and z motion, autofocusing, automatic exposure control, CCD-based image acquisition hardware, and an 80 slide scanning stage.

This system has been previously used for automated scoring of micronuclei (Varga D, Johannes T, Jainta S, Schuster S, Schwarz-Boeger U, Kiechle M, et al. An automated scoring procedure for the micronucleus test by image analysis. Mutagenesis 2004; 19:391-7), dicentric chromosome aberrations (Schunck C, Johannes T, Varga D, Lorch T, Plesch A. New developments in automated cytogenetic imaging: unattended scoring of dicentric chromosomes, micronuclei, single cell gel electrophoresis, and fluorescence signals. Cytogenet Genome Res 2004; 104:383-9), and analysis of single-cell gel electrophoresis (Schunck C, Johannes T, Varga D, Lorch T, Plesch A. New developments in automated cytogenetic imaging: unattended scoring of dicentric chromosomes, micronuclei, single cell gel electrophoresis, and fluorescence signals. Cytogenet Genome Res 2004; 104:383-9).

The Metafer system has also been used for high-throughput scoring of chromosome aberrations (translocations, dicentrics and inversions) of highly exposed radiation workers, as well as micronuclei and γ-H2AX foci (Hande M P, Azizova T V, Geard C R, Burak L E, Mitchell C R, Khokhryakov V F, et al. Past exposure to densely ionizing radiation leaves a unique permanent signature in the genome. Am J Hum Genet. 2003; 72: 1162-70; Mitchell C R, Azizova T V, Hande M P, Burak L E, Tsakok J M, Khokhryakov V F, et al. Stable intrachromosomal biomarkers of past exposure to densely ionizing radiation in several chromosomes of exposed individuals. Radiat Res 2004; 162:257-63; Balajee A S, Geard C R. Replication protein A and gamma-H2AX foci assembly is triggered by cellular response to DNA double-strand breaks. Exp Cell Res 2004; 300:320-34.

Figure 50:
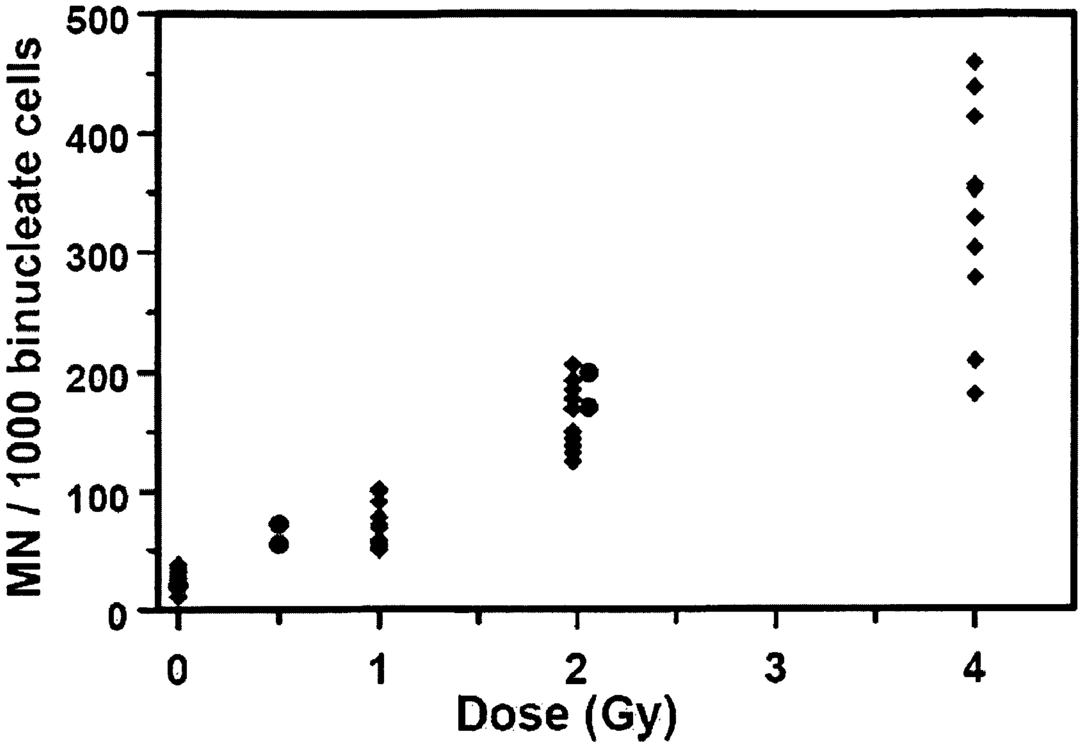
FIG. 50 shows a composite of radiation-induced micronucleus yields (in human lymphocytes irradiated ex vivo) obtained with the Metafer automated scanning system.

FIG. 50 shows a composite of radiation-induced micronucleus yields (in human lymphocytes irradiated ex vivo) obtained with the Metafer automated scanning system, from the MetaSystems group (Varga D, Johannes T, Jainta S, Schuster S, Schwarz-Boeger U, Kiechle M, et al. An automated scoring procedure for the micronucleus test by image analysis. Mutagenesis 2004; 19:391-7) (diamonds) and yields obtained using the system and methods described herein (circles). At a given dose, each data point corresponds to a different individual, indicating the significance of interpersonal variation, particularly at high doses (Thierens H, Vral A, de Ridder L. Biological dosimetry using the micronucleus assay for lymphocytes: interindividual differences in dose response. Health Phys 1991; 61:623-30).

Example

High-speed Imaging with the Amersham IN Cell 3000 Machine

Studies were performed using the state-of-the-art Amersham (GE Healthcare) IN Cell Analyzer 3000. This machine is a line scanning, confocal imaging system, based on standard 96- or 384-well microplates, which was developed specifically for performing high-throughput cellular assay screening very rapidly and at high resolution. It is believed to be currently the fastest such machine on the market. Some key features of the machine are: two laser line-scanning light sources (krypton: 647 nm, and argon: 364 and 488 nm), high speed, dynamic infrared laser autofocus, imaging performed by three high-speed, cooled, 12-bit CCD cameras, field of view using 40× objective is 0.75×0.75 mm with a spatial resolution of 1.2 μm, standard image size is 1250×1250 pixels, so up to 30 individual fields can be imaged per well on a 96 well microplate, well scan time for a single 0.75×0.75 mm field per well, is 2 min at 2.4 μm resolution, and robotically-based microplate handling.

The IN Cell 3000 has dedicated image analysis modules which perform rapid imaging and quantitative analysis of sub-cellular components, as well as a "Developer" module allowing users to "teach" the system to recognize particular structures, such as, binucleated cells and micronuclei.

While the IN Cell 3000 has generally performed well within its limitations, its throughput is limited for the current high throughput purposes by the fact that it does not have the capability to "intelligently" scan. Instead it scans the entire area of interest at high resolution, rather than doing a preliminary scan at low resolution, and then doing high resolution scanning only in areas where there are potentially interesting objects. A second feature that limits its throughput is its use of CCD rather than CMOS technology.

Example

γ-H2AX in Human Peripheral Human Lymphocytes

To date, no information has been published on γ-H2AX foci after irradiation of human lymphocytes. Accordingly, the dose-response and the inter-person variability of radiation induced γ-H2AX foci in peripheral blood lymphocytes was studied. Briefly, blood samples were taken from healthy human volunteers through the NIH Department of Transfusion Medicine, and irradiated ex-vivo within a few minutes of being drawn.

Figure 51:
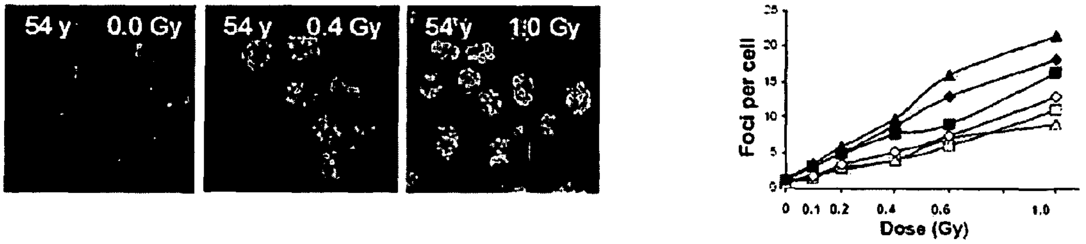
FIG. 51 shows the results of the dose-response and the inter-person variability of radiation induced γ-H2AX foci in peripheral blood lymphocytes.

Blood cells were separated both by fractionation on ficoll-hypaque-metrizoate gradients and using FACS. We Magnetic separation of lymphocyte subpopulations using antigen specificity was also explored. Because the blood used in each experiment was from a different individual, variability between independent experiments from age-defined donors (<30 y, vs. >50 yrs) was examined. Each day blood was obtained from one younger and one older donor, and processed. The experiment was twice repeated with blood from different donors. The results are shown in FIG. 51, together with some in-situ images of the γ-H2AX foci (green) in lymphocytes.

It should be noted that, in these experiments, assays were performed 2 hours after radiation exposure. Based on the published data from Banath J P, Macphail S H, Olive P L. Radiation sensitivity, H2AX phosphorylation, and kinetics of repair of DNA strand breaks in irradiated cervical cancer cell lines. Cancer Res 2004; 64:7144-9, significant increases over controls at 24 h after a 2 Gy exposure were expected.

Example

Robotics

The Manufacturing Research Laboratory (MRL) provides the foundation advanced laser-based manufacturing technologies and industrial manipulators (robots). Published work from the MRL includes work on robotic dynamics (Yao Y L. Transient lateral motion of robots in cylindrical part mating. Robotics and Computer Integrated Manufacturing 1991; 8:103-11; Yao Y L, Korayem M H, Basu A. Maximum allowable load of flexible manipulators for a given dynamic trajectory. Robotics and Computer-Integrated Manufacturing 1993; 10:301-9; Yao Y L, Cheng W. Model based motion planning of robot assembly of non-cylindrical parts. International Journal of Advanced Manufacturing Technology 1999; 15:683-91), precision (Yao Y L, Wu S M. Recursive calibration of industrial manipulators by adaptive filtering. Journal of Engineering for Industry-Transactions of the ASME 1995; 117:406-11), and kinematics (Huang Z, Yao Y L. A new closed-form kinematics of the generalized 3-DOF spherical parallel manipulator. Robotica 1999; 17:475-85; Abdul Majid M Z, Huang Z, Yao Y L. Workspace analysis of a six-DOF, three-PPSR parallel manipulator. International Journal of Advanced Manufacturing Technology 2000; 17:441-9).

Figure 52:
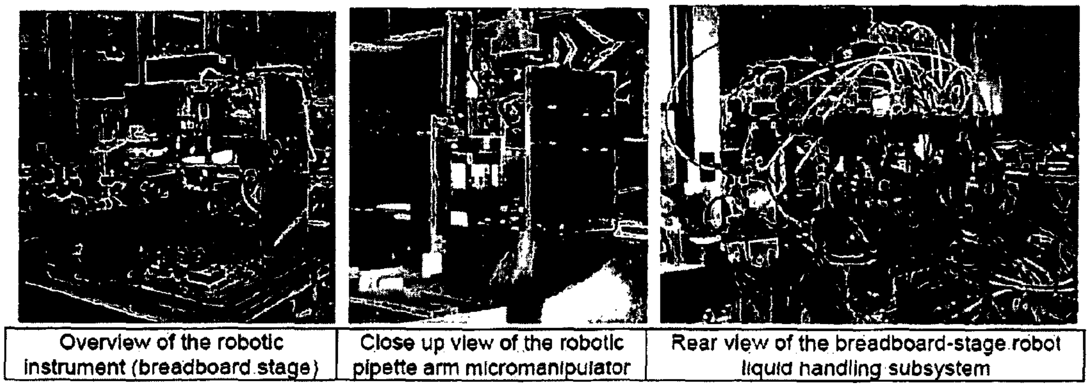
FIG. 52 shows an overview of a robotic instrument at the breadboard stage, a close up view of a robotic pipette arm micromanipulator and a rear view of a breadboard-stage robot liquid handling subsystem.

The MRL is examining studying robotic preparation of cDNA from single cells to develop an instrument that couples the power of robotics with that of DNA array technology. As shown in FIG. 52, the breadboard-stage instrument developed (as described below) incorporates an inverted research microscope capable of wide-field deconvolution microscopy as well as a robotic system for manipulation of cells and reagents. Cells are handled by a robotic pipette arm micromanipulator capable of changing pipette tips, xyz-positioning and nanoliter scale liquid handling. The system incorporates pipetting of several different types of fluids. Pipetting accuracy has been evaluated to validate that the system achieved sufficient linearity and accuracy.

Example

High-Speed In-Situ Cellular Image Analysis

Imaging and Control Program for High Throughput Single-Cell Identification: At Columbia University's Radiological Research Accelerator Facility (RARAF), single-cell single particle irradiation experiments rely on a purpose-built fast cell imaging analysis approach to recognize the specific cell targets for irradiation (Randers-Pehrson G, Geard C R, Johnson G, Elliston C D, Brenner D J. The Columbia University single-ion microbeam. Radiat Res 2001; 156:210-4). In the basic system, an integrated program written under the Windows NT operating system controls the video analysis system and the motion of the stepping motor driven microscope stage. For each culture dish, the approximate locations of the attached cells are established using a low-magnification lens, so that time is not wasted afterwards imaging empty regions of the dish at high magnification. This preliminary scan consists of 10 overlapping images arranged to cover the entire active area of the dish. The area of objects that are brighter than a set threshold is used to identify and locate cells. These locations are then translated into defined fields of view for the high-magnification (40×) objective. Then, each field of view found during the preliminary scan to contain at least one cell is moved into position, and a high-magnification video image is grabbed and analyzed.

This two stage imaging process results in an order of magnitude increase in throughput. The entire imaging process for a dish of 2,000 cells takes 4 minutes; 3 minutes are for the mechanical stage motion time and 1 minute is for reading the CCD. In the current invention, this same two-stage approach is used for imaging, though the system is made much faster by using fast optical scanning mirrors instead of a mechanical stage to switch between the low- and high-magnification fields of view and by using CMOS imaging sensors that have a faster read out than conventional CCD cameras.

Image Analysis Algorithms: To carry out assays on large numbers of cells, techniques for high throughput automatic identification and localization of individual cells have been developed, based on advanced machine learning techniques (Long X, Cleveland W L, Yao Y L. Effective automatic recognition of cultured cells in bright field images using Fisher's linear discriminant preprocessing. In Proceedings of IMECE04: 2004 ASME International Mechanical Engineering Congress. Anaheim, Calif.; 2004; Long X, Cleveland W L, Yao Y L. Automatic detection of unstained viable cells in bright field images using a support vector machine with an improved training procedure. Computers in Biology and Medicine 2004:accepted; Long X, Cleveland W L, Yao Y L. A new preprocessing approach for cell recognition. IEEE Transactions on Information Technology in Biomedicine 2004:accepted). The techniques are highly relevant to the image analysis needs of the current invention, and are used as described in greater detail below.

The learning approach uses a feed-forward Artificial Neural Network in conjunction with an effective preprocessing technique, Fisher Linear Discriminant (FLD) (Long X, Cleveland W L, Yao Y L. A new preprocessing approach for cell recognition. IEEE Transactions on Information Technology in Biomedicine 2004:accepted). In addition, a more sophisticated variation to the Support Vector Machine (SVM) approach has been developed, known as Compensatory Iterative Sample Selection (CISS), to not only identify cells but to further distinguish viable cells from non-viable cells and other non-cell objects (Long X, Cleveland W L, Yao Y L. Automatic detection of unstained viable cells in bright field images using a support vector machine with an improved training procedure. Computers in Biology and Medicine 2004:accepted). An important feature of these algorithms is that they permit supervised learning. Essentially, the system is taught to distinguish between cells and non-cells (or viable-cells and other objects) using images that have been pre-classified by a human expert or other means. Differences in object appearances and image variations such as focus, illumination, size and noise are simply accommodated by training.

Example

Optimization of γ-H2AX Foci Staining Protocol

The need to detect DNA damage by radiation requires specific markers that can be easily seen and quantified, and γ-H2AX foci formation is one such event that can be used in this scenario. It has been shown that H2AX phosphorylation is specific to sites of DNA damage and is also indicative of the amount of DNA damage. However, in order to use γ-H2AX as a quick screening tool, it must be optimized for sensitivity and rapidity, which is what we are aiming to achieve.

The first aspect addressed is the image quality of foci in cells. Several parameters were tested to optimize the image quality. For example, light intensity ratios of foci can be optimized through antibody concentrations during chemiluminescence. The goal was to achieve the sharpest image possible and also to record the relationship between radiation level and foci counts. For the first experiments, to characterize the γH2AX induction, MEF cells in culture were used. In these cells, an increase of foci number with increasing x-ray dose was seen (FIG. 51).

Antibody concentrations were also optimized based on the contrast between the cell background and fluorescence signal given by the γ-H2AX foci. Cells that exhibited the largest intensity ratio were deemed the best for viewing, having the most distinction between foci and cellular background. Images of cells treated with various concentrations of both the primary and secondary antibodies were compared. It was found that the 1:100 dilution for the primary antibody and 1:500 for the secondary antibody yielded the best intensity ratios. A comparison was also done using different kinds of blocking agents, and it was found that even though Superblock (Pierce Biochemicals) yielded faster results, NFDM (Non fat dried milk) provided clearer foci images.

Following these experiments in MEF cells, similar experiments were performed in human lymphocytes. It was found that the primary antibody dilution of 1:50 with a secondary antibody dilution of 1:250 yielded the best brightness of foci. DAPI concentration of 1.5 μg/ml and 250 ng/ml in mounting medium with anti-fade were compared and it was found that 250 ng/ml yielded the best contrast between the foci irradiated with 2 Gy γ-rays and fixed 30 and nuclear membrane.

What is claimed is:

1. A method for high speed image scanning, comprising:

adjusting an object using a positioning element;

directing a portion of an image of the object toward a sensor by positioning a first mirror relative to the object, wherein the first mirror directs the portion of the image of the object in a first direction, and by positioning a second mirror relative to the object and the first mirror, wherein the second mirror directs the portion of the image of the object in a second direction;

controlling the positioning element, the position of the first mirror and the position of the second mirror using a processor; and detecting the portion of the image of the object using the sensor positioned relative to the first mirror and the second mirror, wherein the sensor is at least one of a CMOS sensor and a charge coupled device.

2. The method of claim 1, wherein the first mirror and the second mirror are galvanometric mirrors.

3. The method of claim 1, wherein the positioning element is a linear actuator.

4. The method of claim 1, wherein the positioning element is a stepper motor.

5. The method of claim 1, wherein the object is a biological sample.

6. The method of claim 5, further comprising:

adding microspheres having a predetermined diameter to the biological sample;

illuminating the microspheres such that they emit a wavelength different than a wavelength emitted by the biological sample;

imaging the microspheres; and adjusting the position of the imaging element to bring the biological sample into focus.

7. The method of claim 6, wherein the microspheres are detected using a CMOS sensor.

8. The method of claim 6, wherein the microspheres are detected using a charge coupled device.

9. A method for high speed image scanning, comprising:

adjusting an object using a positioning element;

directing a portion of an image of the object toward a sensor by positioning a first mirror relative to the object, wherein the first mirror directs the portion of the image of the object in a first direction, and by positioning a second mirror relative to the object and the first mirror, wherein the second mirror directs the portion of the image of the object in a second direction;

controlling the positioning element, the position of the first mirror and the position of the second mirror using a processor; and detecting the portion of the image of the object using the sensor positioned relative to the first mirror and the second mirror, wherein the first mirror and the second mirror are located between an objective lens and a tube lens.

10. A method for high speed image scanning, comprising:

adjusting an object using a positioning element;

directing a portion of an image of the object toward a sensor by positioning a first mirror relative to the object, wherein the first mirror directs the portion of the image of the object in a first direction, and by positioning a second mirror relative to the object and the first mirror, wherein the second mirror directs the portion of the image of the object in a second direction;

controlling the positioning element, the position of the first mirror and the position of the second mirror using a processor;

detecting the portion of the image of the object using the sensor positioned relative to the first mirror and the second mirror; and dividing the object into a plurality of fields of view.

11. The method of claim 10, further comprising dividing each of the plurality of fields of view into a plurality of high magnification views.

12. A method for high speed image scanning, comprising:

adjusting an object using a positioning element;

directing a portion of an image of the object toward a sensor by positioning a first mirror relative to the object, wherein the first mirror directs the portion of the image of the object in a first direction, and by positioning a second mirror relative to the object and the first mirror, wherein the second mirror directs the portion of the image of the object in a second direction;

controlling the positioning element, the position of the first mirror and the position of the second mirror using a processor; and detecting the portion of the image of the object using the sensor positioned relative to the first mirror and the second mirror, wherein the object is at least one of glued onto a substrate and laminated onto a substrate.

13. A method for high speed image scanning, comprising:

adjusting an object using a positioning element, wherein the object is a biological sample;

directing a portion of an image of the object toward a sensor by positioning a first mirror relative to the object, wherein the first mirror directs the portion of the image of the object in a first direction, and by positioning a second mirror relative to the object and the first mirror, wherein the second mirror directs the portion of the image of the object in a second direction;

controlling the positioning element, the position of the first mirror and the position of the second mirror using a processor;

detecting the portion of the image of the object using the sensor positioned relative to the first mirror and the second mirror;

adding microspheres having a predetermined diameter to the biological sample;

illuminating the microspheres such that they emit a wavelength different than a wavelength emitted by the biological sample;

imaging the microspheres; and adjusting the position of an imaging element to bring the biological sample into focus, wherein the microspheres have a diameter greater than at least one of about 0.6 micrometers and the diameter of a filter substrate located adjacent to the biological sample.

14. The method of claim 13, wherein the microspheres have a diameter of about 10 micrometers.

15. The method of claim 13, wherein the microspheres are fluorescent and wherein the fluorescence of the microspheres is different than the fluorescence used to image the sample.

16. The method of claim 15, wherein the color of the microspheres have an excitation wavelength of about 625 nm and an emission spectrum of about 645 nm.

17. The method of claim 13, wherein the microspheres are illuminated using a lamp.

18. The method of claim 13, wherein the microspheres are illuminated using a laser.

19. The method of claim 13, further comprising positioning a dichroic mirror in the path of the image of the sample to allow focusing on the microspheres or imaging of the sample.

20. The method of claim 13, wherein the microspheres are fluorescent.

21. A method for high speed image scanning, comprising:

adjusting an object using a positioning element;

directing a portion of an image of the object toward a sensor by positioning a first mirror relative to the object, wherein the first mirror directs the portion of the image of the object in a first direction, and by positioning a second mirror relative to the object and the first mirror, wherein the second mirror directs the portion of the image of the object in a second direction;

controlling the positioning element, the position of the first mirror and the position of the second mirror using a processor;

detecting the portion of the image of the object using the sensor positioned relative to the first mirror and the second mirror; and positioning at least a portion of an imaging element using a piezo nano-positioner.

22. The method of claim 21, wherein the imaging element is a magnifying objective lens.

23. The method of claim 21, wherein the imaging element is a magnifying objective lens and a tube lens.

24. A method for high speed image scanning, comprising:

adjusting an object using a positioning element;

directing a portion of an image of the object toward a sensor by positioning a first mirror relative to the object, wherein the first mirror directs the portion of the image of the object in a first direction, and by positioning a second mirror relative to the object and the first mirror, wherein the second mirror directs the portion of the image of the object in a second direction;

controlling the positioning element, the position of the first mirror and the position of the second mirror using a processor; and detecting the portion of the image of the object using the sensor positioned relative to the first mirror and the second mirror, wherein the sensor is a first sensor and further comprising directing the image of the object toward at least one of the first sensor and a second sensor.

25. The method of claim 24, wherein the image of the object is directed along a first optical path to the first sensor and along a second optical path to the second sensor.

26. The method of claim 25, further comprising magnifying a first image along the first optical path to a first level of magnification and magnifying a second image along the second optical path to a second level of magnification.

27. The method of claim 24, wherein the image of the object is directed toward at least one of the first sensor and the second sensor using a dichroic mirror.

28. The method of claim 24, further comprising directing a plurality of images of the object to the first sensor.

29. The method of claim 28, further comprising analyzing the plurality of images.

30. The method of claim 29, wherein at least one of the plurality of images is analyzed using cluster analysis.

31. The method of claim 30, further comprising:

analyzing the results of the cluster analysis;

comparing the results of the cluster analysis to a threshold; and directing an image of the object to the second sensor when the results of the cluster analysis exceed the threshold.

32. The method of claim 24, wherein the second sensor is a 3 CMOS color sensor array.

33. The method of claim 24, further comprising illuminating the object using a light source.

34. The method of claim 33, wherein the light source is an argon ion laser.

35. The method of claim 33, wherein the light source is an LED.

36. The method of claim 33, wherein the light source is a lamp.

37. The method of claim 24, further comprising illuminating the object for a first instance using a first light source and illuminating the object for a second instance using a second light source.

38. The method of claim 37, wherein the first light source is an LED and the second light source is an argon ion laser.

39. An apparatus for high speed image scanning, comprising:

an imaging element;

a positioning element controllable in an x direction and in a y direction, coupled to an object, wherein the positioning element adjusts the position of the object;

a first mirror positioned relative to the object;

a second mirror positioned relative to the object and the first mirror, wherein the first mirror directs at least one image of the object in the x direction toward the second mirror and wherein the second mirror directs the at least one image of the object in the y direction toward a sensor; and a processor coupled to the positioning element, the first mirror and the second mirror, wherein the processor controls the positioning element, the position of the first mirror and the position of the second mirror, wherein the sensor is at least one of a CMOS sensor and a charge coupled device.

40. The apparatus of claim 39, wherein the first mirror and the second mirror are galvanometric mirrors.

41. The apparatus of claim 39, wherein the positioning element is a linear actuator.

42. The apparatus of claim 39, wherein the positioning element is a stepper motor.

43. The apparatus of claim 39, wherein the first mirror and the second mirror are adjusted to provide images of the object from a plurality of fields of view.

44. The apparatus of claim 43, wherein the first mirror and the second mirror are adjusted to provide a plurality of high magnification images of the object from each of the plurality of fields of view.

45. The apparatus of claim 39, wherein the object is a sample in a well in an array.

46. The apparatus of claim 45, further comprising:

a plurality of microspheres having a predetermined diameter; wherein the microspheres are added to the sample;

a light source, wherein the light source illuminates the microspheres such that the microspheres emit a wavelength different than a wavelength emitted by the sample; and wherein the sensor detects images of the microspheres and the positioning element adjusts the position of the imaging element to bring the sample into focus.

47. The apparatus of claim 45, wherein the imaging element is a magnifying objective lens.

48. The apparatus of claim 45, further comprising a dichroic mirror, wherein the dichroic mirror is positioned in a path of the image of the sample to allow imaging of the sample.

49. An apparatus for high speed image scanning, comprising:

an imaging element;

a positioning element controllable in an x direction and in a y direction, coupled to an object, wherein the positioning element adjusts the position of the object;

a first mirror positioned relative to the object;

a second mirror positioned relative to the object and the first mirror, wherein the first mirror directs at least one image of the object in the x direction toward the second mirror and wherein the second mirror directs the at least one image of the object in the y direction toward a sensor;

a processor coupled to the positioning element, the first mirror and the second mirror, wherein the processor controls the positioning element, the position of the first mirror and the position of the second mirror; and an objective lens and a tube lens, wherein the first mirror and the second mirror are located between the objective lens and the tube lens.

50. An apparatus for high speed image scanning, comprising:

an imaging element;

a positioning element controllable in an x direction and in a y direction, coupled to an object, wherein the positioning element adjusts the position of the object;

a first mirror positioned relative to the object;

a second mirror positioned relative to the object and the first mirror, wherein the first mirror directs at least one image of the object in the x direction toward the second mirror and wherein the second mirror directs the at least one image of the object in the y direction toward a sensor; and a processor coupled to the positioning element, the first mirror and the second mirror, wherein the processor controls the positioning element, the position of the first mirror and the position of the second mirror, wherein a portion of the imaging element is a magnifying objective lens.

51. An apparatus for high speed image scanning, comprising:

an imaging element;

a positioning element controllable in an x direction and in a y direction, coupled to an object, wherein the positioning element adjusts the position of the object, wherein the object is a sample in a well in an array, and wherein the positioning element adjusts the position of the imaging element to bring the sample into focus;

a first mirror positioned relative to the object;

a second mirror positioned relative to the object and the first mirror, wherein the first mirror directs at least one image of the object in the x direction toward the second mirror and wherein the second mirror directs the at least one image of the object in the y direction toward a sensor;

a processor coupled to the positioning element, the first mirror and the second mirror, wherein the processor controls the positioning element, the position of the first mirror and the position of the second mirror;

a plurality of microspheres having a predetermined diameter, wherein the microspheres are added to the sample; and a light source configured to illuminate the microspheres such that the microspheres emit a wavelength different than a wavelength emitted by the sample, wherein the sensor detects images of the microspheres and wherein the microspheres have a diameter greater than at least one of about 0.6 micrometers and the diameter of a filter substrate included in the well.

52. The apparatus of claim 51, wherein the microspheres have a diameter of about 10 micrometers.

53. The apparatus of claim 51, wherein the microspheres further have a fluorescence and wherein the fluorescence is different than the fluorescent used to image the sample.

54. The apparatus of claim 53, wherein the microspheres further have an excitation wavelength of about 625 nm and an emission spectrum of about 645 nm.

55. The apparatus of claim 51, wherein the microspheres are illuminated using a lamp.

56. The apparatus of claim 51, wherein the microspheres are illuminated using a laser.

57. The apparatus of claim 51, wherein the microspheres are illuminated using a diode.

58. The apparatus of claim 51, further comprising a dichroic mirror positioned in a path of the image of the sample to allow focusing on the microspheres.

59. An apparatus for high speed image scanning, comprising:

an imaging element;

a positioning element controllable in an x direction and in a y direction, coupled to an object, wherein the positioning element adjusts the position of the object, wherein the object is a sample in a well in an array, and wherein the positioning element adjusts the position of the imaging element to bring the sample into focus;

a first mirror positioned relative to the object;

a second mirror positioned relative to the object and the first mirror, wherein the first mirror directs at least one image of the object in the x direction toward the second mirror and wherein the second mirror directs the at least one image of the object in the y direction toward a sensor;

a processor coupled to the positioning element, the first mirror and the second mirror, wherein the processor controls the positioning element, the position of the first mirror and the position of the second mirror;

a plurality of microspheres having a predetermined diameter, wherein the microspheres are added to the sample; and a light source configured to illuminate the microspheres such that the microspheres emit a wavelength different than a wavelength emitted by the sample, wherein the sensor detects images of the microspheres and wherein the microspheres have a diameter similar to the diameter of the object to be imaged.

60. An apparatus for high speed image scanning, comprising:

an imaging element;

a positioning element controllable in an x direction and in a y direction, coupled to an object, wherein the positioning element adjusts the position of the object, wherein the object is a sample in a well in an array, and wherein the positioning element adjusts the position of the imaging element to bring the sample into focus;

a first mirror positioned relative to the object;

a second mirror positioned relative to the object and the first mirror, wherein the first mirror directs at least one image of the object in the x direction toward the second mirror and wherein the second mirror directs the at least one image of the object in the y direction toward a sensor;

a processor coupled to the positioning element, the first mirror and the second mirror, wherein the processor controls the positioning element, the position of the first mirror and the position of the second mirror;

a plurality of microspheres having a predetermined diameter, wherein the microspheres are added to the sample; and a light source configured to illuminate the microspheres such that the microspheres emit a wavelength different than a wavelength emitted by the sample, wherein the sensor detects images of the microspheres and wherein the microspheres are detected using at least one of a CMOS sensor and a charge coupled device.

61. An apparatus for high speed image scanning, comprising:

an imaging element;

a positioning element controllable in an x direction and in a y direction, coupled to an object, wherein the positioning element adjusts the position of the object and wherein the object is a sample in a well in an array;

a first mirror positioned relative to the object;

a second mirror positioned relative to the object and the first mirror, wherein the first mirror directs at least one image of the object in the x direction toward the second mirror and wherein the second mirror directs the at least one image of the object in the y direction toward a sensor; and a processor coupled to the positioning element, the first mirror and the second mirror, wherein the processor controls the positioning element, the position of the first mirror and the position of the second mirror, wherein the position of at least a portion of the imaging element is adjusted using a piezo nano-positioner.

62. An apparatus for high speed image scanning, comprising:

an imaging element;

a positioning element controllable in an x direction and in a y direction, coupled to an object, wherein the positioning element adjusts the position of the object;

a first mirror positioned relative to the object;

a second mirror positioned relative to the object and the first mirror, wherein the first mirror directs at least one image of the object in the x direction toward the second mirror and wherein the second mirror directs the at least one image of the object in the y direction toward a first sensor;

a second sensor, wherein the first mirror directs an image in the x direction toward the second mirror and wherein the second mirror directs the image in the y direction toward at least one of the first sensor and the second sensor; and a processor coupled to the positioning element, the first mirror and the second mirror, wherein the processor controls the positioning element, the position of the first mirror and the position of the second mirror.

63. The apparatus of claim 62, wherein the first sensor is positioned along a first optical path and the second sensor is positioned along a second optical path.

64. The apparatus of claim 63, wherein the first optical path includes a first level of magnification and the second optical path includes a second level of magnification.

65. The apparatus of claim 62, wherein at least one of a plurality of images is directed to the first sensor.

66. The apparatus of claim 65, further comprising a software program for analyzing the plurality of images.

67. The apparatus of claim 66, wherein the at least one of the plurality of images is analyzed using cluster analysis.

68. The apparatus of claim 67, wherein the results of the cluster analysis are compared to a threshold, and wherein when the results of the cluster analysis exceed the threshold an image of the object is directed to the second sensor.

69. The apparatus of claim 62, wherein the second sensor is a 3 CMOS color sensor array.

70. The apparatus of claim 62, further comprising a light source, wherein the light source illuminates the object.

71. The apparatus of claim 70, wherein the light source is an argon ion laser.

72. The apparatus of claim 70, wherein the light source is an LED.

73. The apparatus of claim 70, wherein the light source is a lamp.

74. The apparatus of claim 62, further comprising a first light source and a second light source.

75. The apparatus of claim 74, wherein the first light source is an LED and the second light source is an argon ion laser.

* * * * *

UNITED STATES PATENT AND TRADEMARK OFFICE

CERTIFICATE OF CORRECTION

PATENT NO. : 7,826,977 B2
APPLICATION NO. : 11/895470
DATED : November 2, 2010
INVENTOR(S) : Guy Garty et al.

It is certified that error appears in the above-identified patent and that said Letters Patent is hereby corrected as shown below:

Column 1, lines 17-20, Government Support Paragraph, should read:

-- This invention was made with Government support under Grant AI067773 awarded by the Department of Health and Human Services. The Government has certain rights in the invention. --

Signed and Sealed this
First Day of January, 2013

David J. Kappos
*Director of the United States Patent and Trademark Office*

UNITED STATES PATENT AND TRADEMARK OFFICE

CERTIFICATE OF CORRECTION

PATENT NO. : 7,826,977 B2
APPLICATION NO. : 11/895470
DATED : November 2, 2010
INVENTOR(S) : Guy Garty et al.

It is certified that error appears in the above-identified patent and that said Letters Patent is hereby corrected as shown below:

In the Specification

Column 1, lines 17-20 Government Support Paragraph should read as follows:

[0002] This invention was made with Government support under Grant AI067773 awarded by the Department of Health and Human Services of the National Institutes of Health. The Government has certain rights in the invention.

Signed and Sealed this
Tenth Day of February, 2015

Michelle K. Lee

Michelle K. Lee
*Deputy Director of the United States Patent and Trademark Office*